United States Patent
Kufer et al.

(10) Patent No.: US 7,635,472 B2
(45) Date of Patent: Dec. 22, 2009

(54) PHARMACEUTICAL COMPOSITIONS COMPRISING BISPECIFIC ANTI-CD3, ANTI-CD19 ANTIBODY CONSTRUCTS FOR THE TREATMENT OF B-CELL RELATED DISORDERS

(75) Inventors: Peter Kufer, Moosburg (DE); Ralf Lutterbuse, Munich (DE); Birgit Kohleisen, Munich (DE); Steven Zeman, Munich (DE); Patrick Bauerle, Gauting (DE)

(73) Assignee: Micromet AG, Munchen (DE)

( * ) Notice: Subject to any disclaimer, the term of this patent is extended or adjusted under 35 U.S.C. 154(b) by 332 days.

(21) Appl. No.: 10/554,852

(22) PCT Filed: May 26, 2004

(86) PCT No.: PCT/EP2004/005685

§ 371 (c)(1),
(2), (4) Date: Apr. 4, 2006

(87) PCT Pub. No.: WO2004/106381

PCT Pub. Date: Dec. 9, 2004

(65) Prior Publication Data

US 2007/0123479 A1  May 31, 2007

(30) Foreign Application Priority Data

May 31, 2003 (EP) .................................. 03012136

(51) Int. Cl.
A61K 39/395 (2006.01)
C07K 16/00 (2006.01)

(52) U.S. Cl. .................................. 424/130.1; 530/387.1

(58) Field of Classification Search ........................ None
See application file for complete search history.

(56) References Cited

U.S. PATENT DOCUMENTS

| | | | |
|---|---|---|---|
| 5,239,062 A | 8/1993 | Blattlick et al. | |
| 6,132,992 A * | 10/2000 | Ledbetter et al. | 435/69.7 |
| 7,112,324 B1 | 9/2006 | Dorken et al. | |
| 2006/0193852 A1 | 8/2006 | Dorken et al. | |

FOREIGN PATENT DOCUMENTS

| | | |
|---|---|---|
| DE | 195 31 348 A1 | 2/1997 |
| EP | 0 505 908 A1 | 9/1992 |
| EP | 1293514 A1 | 3/2003 |
| WO | WO 91/09968 A1 | 7/1991 |
| WO | WO 95/11922 A1 | 5/1995 |
| WO | WO 96/36360 A1 | 11/1996 |
| WO | WO 99/54440 A1 | 10/1999 |
| WO | WO 02/16414 | 2/2002 |

OTHER PUBLICATIONS

ATCC entry for OKT3, 2009, 2 pages.*

Peter M. Anderson et al., G19.4(αCD3)×R43(αCD19) Monuclonal Antibody Heteroconjugate Triggers CD19 Antigen-Specific Lysis of t(4;11) Acute Lymphoblastic Leukemia Cells by Activated CD3 Antigen-Positive Cytotoxic T Cells, *Blood*, vol. 80. No. 11 Dec. 1, 1992: pp. 2826-2834.

Heribert Bohlen et al., "Lysis of Malignant B Cells From Patients With B-Chronic Lymphocytic Leukemia by Autologous T Cells Activated With CD3×CD19 Bispecific Antibodies in Combination With Bivalent CD28 Antibodies," *Blood* vol. 82. No. 6 Sep. 15, 1993: pp. 1803-1812.

Heribert Bohlen et al., "Cytolysis of Leukemic B-Cells by T-Cells Activated via Two Bispecific Antibodies," *Cancer Research* 53. 4310-4314, Sep. 15, 1993.

Heribert Bohlen et al., "Prevention of Epstein-Barr Virus-induced Human B-Cell Lymphoma in Severe Combined Immunodeficient Mice Treated with CD3×CD19 Bispeciffc Antibodies, CD28 Monospecific Antibodies, and Autologous T Cells," *Cancer Research*, 57: 1704-1709, May 1, 1997.

M. Cóska et al., "Activation of T cell cytotoxicity against autologous common acute lymphoblastic leukemia (cALL) blasts by CD3×CD19 bispecific antibody," *Leukemia* (1996) 10, 1765-1772.

Jan De Jonge et al., "Bispecific antibody treatment of murine B cell lymphoma," *Cancer Immunol Immunother* (1997) 45:162-165.

Torsten Dreier et al., "Extremely Potent, Rapid And Costimulation-Independent Cytotoxic T-Cell Response Against Lymphoma Cells Catalyzed By A Single-Chain Bispecific Antibody," *Int. J. Cancer*. 100, 000-000 (2002).

Inez-Anne Haagen et al., "Killing of human leukaemia/lymphoma B cells by activated cytotoxic T lymphocytes in the presence of a bispeciiic monoclonal antibody (αCD3/αCD19)," *Clin. Exp. Immunol.*, (1992) 90, 368-375.

Inez-Anne Haagen et al., "Killing of Autologous B-Lineage Malignancy Using CD3×CD19 Bispecific Monoclonal Antibody in End Stage Leukemia and Lymphoma," *Blood*, vol. 84. No. 2 Jul. 15, 1994: pp. 556-563.

Inez-Anne Haagen et al., "Unprimed $CD4^+$ and $CD8^+$ T cells can be rapidly activated by a CD3×CD19 bispecific antibody to proliferate and become cytotoxic," *Cancer Immunol Immunother* (1994) 39: 391-396.

Inez-Anne Haagen et al., "The Efficacy of CD3×CD19 Bispecific Monoclonal Antibody (BsAb) in a Clonogenic Assay: The Effect of Repeated Addition of BsAb and Interleukin-2," *Blood*, vol. 85, No. 11 Jun. 1, 1995: pp. 3208-3212.

P. Kufer et al., "Construction and biological activity of a recombinant bispecific single-chain antibody designed for therapy of minimal residual colorectal cancer," *Cancer Immunol Immunother* (1997) 45: 193-197.

(Continued)

Primary Examiner—Ilia Ouspenski
(74) Attorney, Agent, or Firm—Foley & Lardner LLP

(57) ABSTRACT

The present invention relates to a pharmaceutical composition comprising a bispecific single chain antibody construct comprising binding domains specific for human CD3 and human CD19, wherein the corresponding variable heavy chain regions ($V_H$) and the corresponding variable light chain regions ($V_L$) regions are arranged, from N-terminus to C-terminus, in the order $V_H$(CD19)-$V_L$(CD19)-$V_H$(CD3)-$V_L$(CD3) or $V_H$(CD3)-$V_L$-(CD3)-$V_H$(CD19)-$V_L$ (CD19). Processes for the production of the pharmaceutical compositions and medical/pharmaceutical uses for the specific bispecific single chain antibody molecules bearing specificities for the human CD3 antigen and the human CD19 antigen are also disclosed.

8 Claims, 14 Drawing Sheets

OTHER PUBLICATIONS

Figure 2:
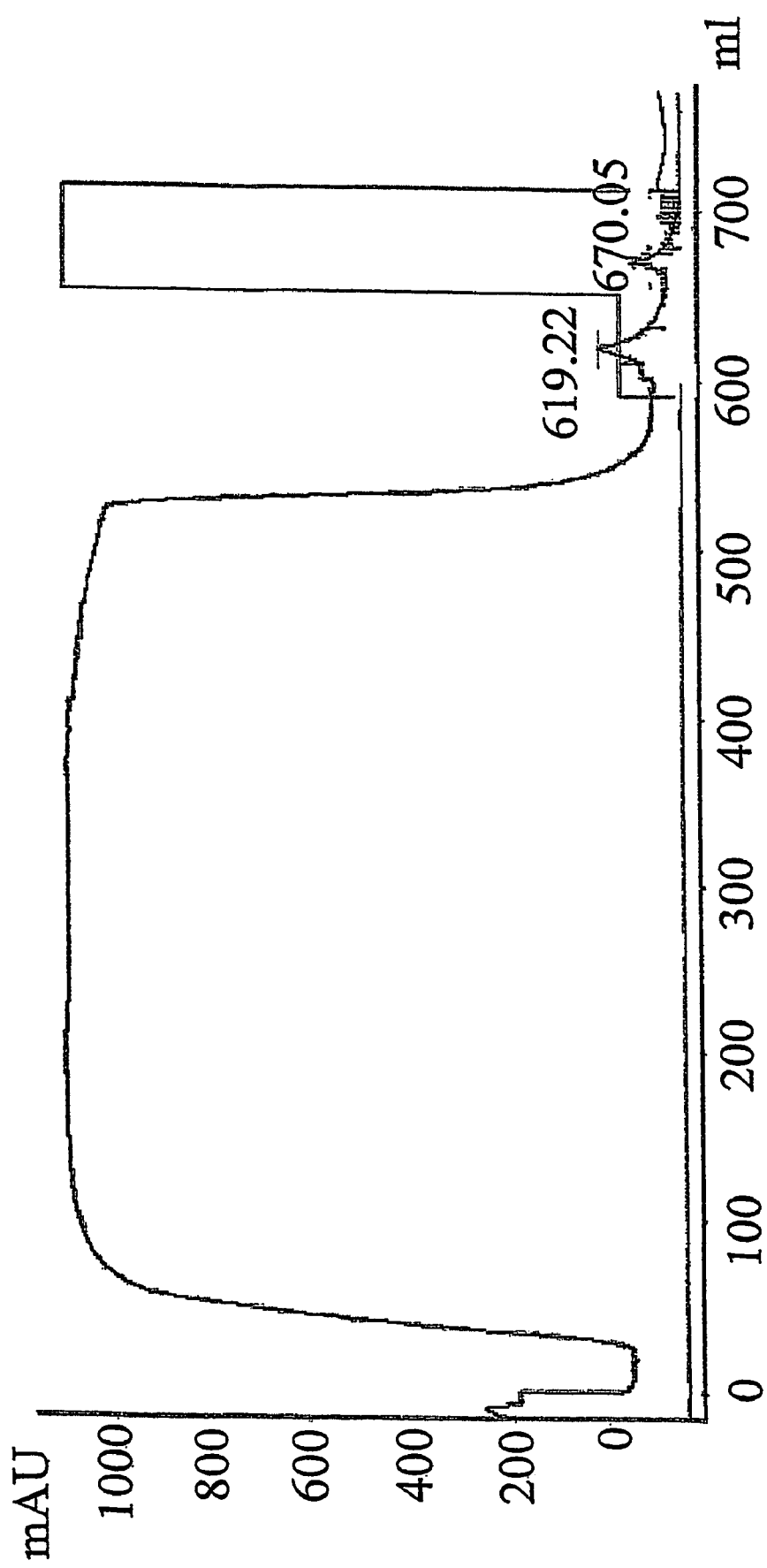

Peter Kufer et al., "Minimal costimulatory requirements for T cell priming and TH1 differentiation: Activation of naive human T lymphocytes by tumor cells armed with bifunctional antibody constructs," *Cancer Immunity* 1:10 (2001).

Anja Löffler et al., "A recombinant bispecific single-chain antibody, CD19×CD3, induces rapid and high lymphoma-directed cytotoxicity by unstimulated T lymphocytes," *Blood*, Mar. 15, 2000, vol. 95, No. 6.

Anja Löffler et al., "Efficient elimination of chronic lymphocytic leukaemia B cells by autologous T cells with a bispecific anti-CD19/anti-CD3 single-chain antibody construct," *Leukemia* (2003) 17, 900-909.

Matthias Mack et al., "A small bispecific antibody construct expressed as a functional single-chain molecule with high tumor cell cytotoxicity," *Proc. Natl. Acad. Sci. USA*, vol. 92, pp. 7021-7025, Jul. 1995.

Matthias Mack et al., "Biologic Properties of a Bispecific Single-Chain Antibody Directed Against 17-1A (EpCAM) and CD3, Tumor Cell-Dependent T Cell Stimulation and Cytotoxic Activity," *The Journal of Immunology*, 1997, 158: 3965-3970.

George J. Weiner et al., "Bispecific Monoclonal Antibody Therapy of B-Cell Malignancy," *Leukemia and Lymphoma*, vol. 16, pp. 199-207, 1995.

Dreier et al., "T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct," The Journal of Immunology, Apr. 15, 2003, vol. 170, No. 8, pp. 4397-4402.

Kipriyanov et al., "Bispecific CD3×CD19 diabody for T cell-mediated lysis of malignant human B cells," International Journal of Cancer, Aug. 31, 1998, vol. 77, No. 4, pp. 763-771.

Kipriyanov et al., "Bispecific Tandem Diabody for Tumor Therapy with Improved Antigen Binding and Pharmacokinetics," J. Mol. Biol., 1999, vol. 293, pp. 41-56.

Kipriyanov et al., "Effect of Domain Order on the Activity of Bacterially Produced Bispecific Single-chain Fv Antibodies," J. Mol. Biol., Jun. 27, 2003, vol. 330, pp. 99-111.

Loeffler et al., "A recombinant bispecific single-chain antibody, CD19×CD3, induces rapid and high lymphoma-directed cytotoxicity by unstimulated T lymphocytes," Blood, Mar. 15, 2000, vol. 95, No. 6, pp. 2098-2103.

Loeffler et al., "Efficient elimination of chronic lymphocytic leukaemia B cells by autologous T cells with a bispecific anti-CD19/anti-CD3 single-chain antibody construct," Leukemia, May 2003, vol. 17, pp. 900-909.

Haagen, I., "Performance of CD3×CD19 Bispecific Monoclonal Antibodies in B Cell Malignancy," *Leukemia and Lymphoma*, vol. 19, 1995, pp. 381-393.

Hayden, M.S., et al., "Single-chain Mono- and Bispecific Antibody Derivatives with Novel Biological Properties and Antitumour Activity from a COS Cell Transient Expression System," *Therapeutic Immunology*, vol. 1, 1994, pp. 3-15.

Holliger, P., et al., "Diabodies: Small Bispecific Antibody Fragments," *Cancer Immunol. Immunother*, vol. 45, 1997, pp. 128-130.

Kipriyanov, S.M., et al. "Rapid Detection of Recombinant Antibody Fragments Directed Against Cell-surface Antigens by Flow Cytometry," *J. of Immunological Methods*, vol. 196, 1996, pp. 51-62.

Kipriyanov, S. M., et al., "Bispecific diabody for lysis of human B-lineage leukemia cells," The Fourteenth International Conf. on Adv. In the Application of Monoclonal Antibodies in Clinical Oncology, May 5-7, 1997, Thira Santorini, Greece, p. 29.

Kostelny, S.A., "Formation of a Bispecific Antibody by the Use of Leucine Zippers," *J. of Immunology*, vol. 148, No. 5, 1992, pp. 1547-1553.

Kumar, P., et al., *Clinical Medicine*, 3rd Edition, pp. 369-370, Bailliere Tindall, (Exhibit 3).

"National Cancer Institute Sponsored Study of Classifications of Non-Hodgkin's Lymphomas, Summary and Description of a Working Formulation for Clinical Usage," *Cancer*, vol. 49, 1982, pp. 2112-2135, (Exhibit 1).

Olsen et al., *Hybridoma and Hybridomics*, 22:65, 2003.

Pezzutto, A., et al., "CD19 Monoclonal Antibody HD37 Inhibits Anti-Immunoglobulin-induced B Cell Activation and Proliferation," *J. of Immunology*, vol. 138, No. 9, 1997, pp. 2793-2799.

Reusch, U., et al., "Effect of Tetravalent Bispecific CD19×CD3 Recombinant Antibody Construct and CD28 Costimulation of Lysis of Malignant B Cells from Patients with Chronic Lymphocytic Leukemia by Autologous T Cells," *Int. J. Cancer*, vol. 112, 2004, pp. 509-518.

Rudikoff, et al., *PNAS*, 79:1979, 1982.

Schroder, A., et al., "A Recombinant Bispecific Single Chain Antibody CD19×CD3 Induced Rapid B Cell Lymphoma-Directed Cytotoxicity of Unstimulated Human T Cells," 40th Annual Meeting Of The American Society Of Hematology Miami Beach, Florida, Dec. 4-8, 1998, XP-002115457, abstract.

Sompuram, et al., *The Journal of Immunology*, 156:1071-81, 1996.

Stein, H., et al., "Die neue WHO-Klassifikation der malignen Lymphome," *Deutsches Arzteblatt*, vol. 96, Dec. 1999, pp. C-2302-C-2309, including English language summary, (Exhibit 2).

Traunecker, A., et al. "JANUSIN: New Molecular Design for Bispecific Reagents," *Int. J. Cancer. Suppl.* 7, 1992, pp. 51-52.

Weiner, G.J., et al., "The Role of T Cell Activation in Anti-CD3×Antitumor Bispecific Antibody Therapy," *J. of Immunology*, vol. 152, 1994, pp. 2385-2392.

Bohlen, H., et al., "Treatment of EB-Virus Induced B-Cell LCL in SCID-HU Mice Using CD3×CD19 Bispecific and CD28 antibodies," Proceedings of the American Association for Cancer Research, vol. 35, Mar. 1994, p. 510, XP-002076122, abstract.

Davis, B.M., et al., "Current Progress in the Gene Therapy of Cancer," *Current Opinion in Oncology*, vol. 8, 1996, pp. 499-508.

De Gast, G. C., et al., "Clinical Experience with CD3×CD19 Bispecific antibodies in Patients with B Cell Malignancies," *J. Hema.*, vol. 4, 1995, pp. 433-437.

De Jonge, J., et al., "Production and Characterization of Bispecific Single-Chain Antibody Fragments," *Molecular Immunology*, vol. 32, No. 17/18, 1995, pp. 1405-1412, (Exhibit 4).

De Jonge, J., et al., "In Vivo Retargeting of T Cell Effector Function by Recombinant Bispecific Single Chain Fv (Anti-CD3×Anti-Idiotype) Induces Long-Term Survival in the Murine BCL1 Lymphoma Model1," *The Journal of Immunology*, vol. 161, 1998, pp. 1454-1461, (Exhibit 5).

Edelstein, M.L., et al., "Gene Therapy Clinical Trials Worldwide: 1989-2004—An Overview," *J. Gene Med.*, vol. 6, 2004, pp. 597-605.

Gruber, M., et al., "Efficient Tumor Cell Lysis Mediated by a Bispecific Single Chain Antibody Expressed in *Escherichia coli*," *J. of Immunology*, vol. 152, 1994, pp. 5368-5374.

Kumar, P., et al., *Clinical Medicine*, 3rd Edition, pp. 369-370, Bailliere Tindall, (Exhibit 3), (1994).

* cited by examiner

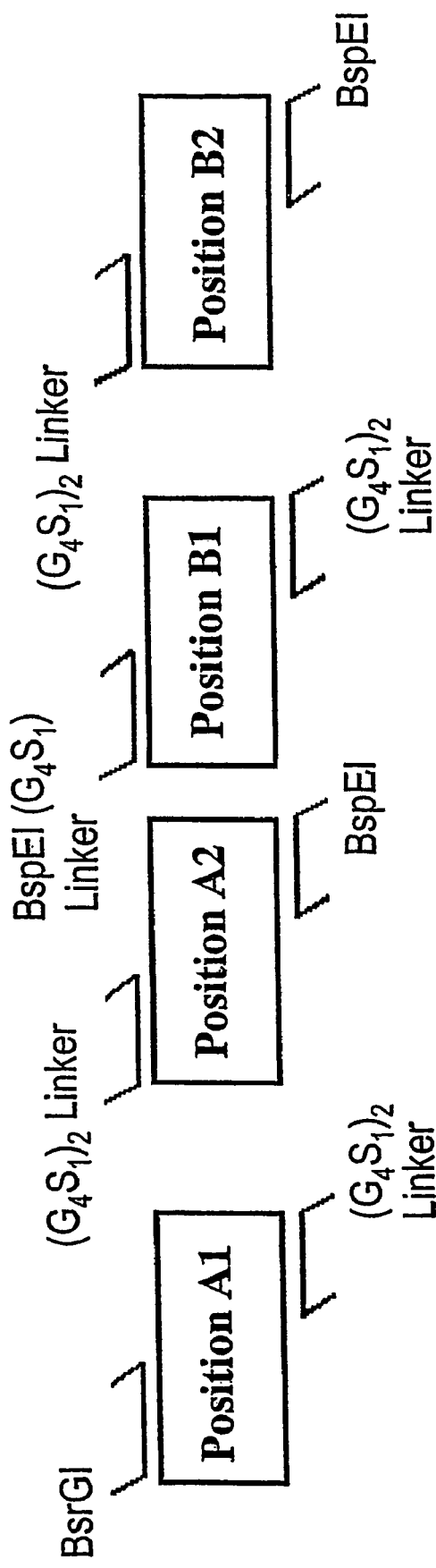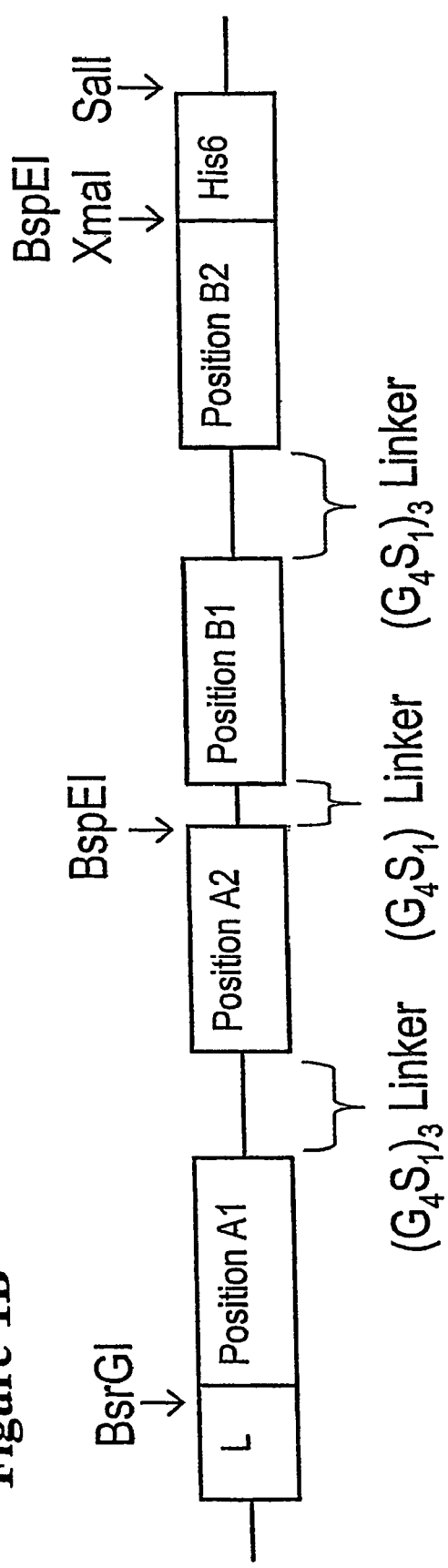
Figure 1A
Figure 1B

SEQUENCE LISTING

```
<160> NUMBER OF SEQ ID NOS: 83

<210> SEQ ID NO 1
<211> LENGTH: 1533
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
tgtacactcc caggtgcagc tgcagcagtc tggggctgag ctggtgaggc ctgggtcctc      60
agtgaagatt tcctgcaagg cttctggcta tgcattcagt agctactgga tgaactgggt     120
gaagcagagg cctggacagg gtcttgagtg gattggacag atttggcctg agatggtga     180 tactaactac aatggaaagt tcaagggtaa agccactctg actgcagacg aatcctccag     240
cacagcctac atgcaactca gcagcctagc atctgaggac tctgcggtct atttctgtgc     300
aagacgggag actacgacgg taggccgtta ttactatgct atggactact ggggccaagg     360
```

-continued

```
gaccacggtc accgtctcct ccggtggtgg tggttctggc ggcggcggct ccggtggtgg    420
tggttctgat atccagctga cccagtctcc agcttctttg gctgtgtctc tagggcagag    480
ggccaccatc tcctgcaagg ccagccaaag tgttgattat gatggtgata gttatttgaa    540
ctggtaccaa cagattccag acagccacc caaactcctc atctatgatg catccaatct    600
agtttctggg atcccaccca ggtttagtgg cagtgggtct gggacagact tcaccctcaa    660
catccatcct gtggagaagg tggatgctgc aacctatcac tgtcagcaaa gtactgagga    720
tccgtggacg ttcggtggag ggaccaagct cgagatcaaa tccggaggtg gtggatccga    780
tatcaaactg cagcagtcag gggctgaact ggcaagacct ggggcctcag tgaagatgtc    840
ctgcaagact tctggctaca cctttactag gtacacgatg cactgggtaa acagaggcc    900 tggacagggt ctggaatgga ttggatacat taatcctagc cgtggttata ctaattacaa    960
tcagaagttc aaggacaagg ccacattgac tacagacaaa tcctccagca cagcctacat    1020
gcaactgagc agcctgacat ctgaggactc tgcagtctat tactgtgcaa gatattatga    1080
tgatcattac tgccttgact actggggcca aggcaccact ctcacagtct cctcagtcga    1140
aggtggaagt ggaggttctg gtggaagtgg aggttcaggt ggagtcgacg acattcagct    1200
gacccagtct ccagcaatca tgtctgcatc tccaggggag aaggtcacca tgacctgcag    1260
agccagttca gtgtaagtt acatgaactg gtaccagcag aagtcaggca ctcccccaa    1320 aagatggatt tatgacacat ccaaagtggc ttctggagtc ccttatcgct tcagtggcag    1380
tgggtctggg acctcatact ctctcacaat cagcagcatg gaggctgaag atgctgccac    1440
ttattactgc caacagtgga gtagtaaccc gctcacgttc ggtgctggga ccaagctgga    1500
gctgaaacat catcaccatc atcattagtc gac                                 1533
```

<210> SEQ ID NO 2
<211> LENGTH: 505
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ala Ser Leu Ala Val Ser Leu Gly Gln Arg Ala Thr Ile
```

```
                145                 150                 155                 160
Ser Cys Lys Ala Ser Gln Ser Val Asp Tyr Asp Gly Asp Ser Tyr Leu
                165                 170                 175

Asn Trp Tyr Gln Gln Ile Pro Gly Gln Pro Lys Leu Leu Ile Tyr
            180                 185                 190

Asp Ala Ser Asn Leu Val Ser Gly Ile Pro Pro Arg Phe Ser Gly Ser
        195                 200                 205

Gly Ser Gly Thr Asp Phe Thr Leu Asn Ile His Pro Val Glu Lys Val
        210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys Ser Gly Gly Gly Ser
                245                 250                 255

Asp Ile Lys Leu Gln Gln Ser Gly Ala Glu Leu Ala Arg Pro Gly Ala
                260                 265                 270

Ser Val Lys Met Ser Cys Lys Thr Ser Gly Tyr Thr Phe Thr Arg Tyr
                275                 280                 285

Thr Met His Trp Val Lys Gln Arg Pro Gly Gln Gly Leu Glu Trp Ile
            290                 295                 300

Gly Tyr Ile Asn Pro Ser Arg Gly Tyr Thr Asn Tyr Asn Gln Lys Phe
305                 310                 315                 320

Lys Asp Lys Ala Thr Leu Thr Thr Asp Lys Ser Ser Ser Thr Ala Tyr
                325                 330                 335

Met Gln Leu Ser Ser Leu Thr Ser Glu Asp Ser Ala Val Tyr Tyr Cys
                340                 345                 350

Ala Arg Tyr Tyr Asp Asp His Tyr Cys Leu Asp Tyr Trp Gly Gln Gly
                355                 360                 365

Thr Thr Leu Thr Val Ser Ser Val Glu Gly Gly Ser Gly Gly Ser Gly
            370                 375                 380

Gly Ser Gly Gly Ser Gly Val Asp Asp Ile Gln Leu Thr Gln Ser
385                 390                 395                 400

Pro Ala Ile Met Ser Ala Ser Pro Gly Glu Lys Val Thr Met Thr Cys
                405                 410                 415

Arg Ala Ser Ser Ser Val Ser Tyr Met Asn Trp Tyr Gln Gln Lys Ser
                420                 425                 430

Gly Thr Ser Pro Lys Arg Trp Ile Tyr Asp Thr Ser Lys Val Ala Ser
            435                 440                 445

Gly Val Pro Tyr Arg Phe Ser Gly Ser Gly Ser Gly Thr Ser Tyr Ser
        450                 455                 460

Leu Thr Ile Ser Ser Met Glu Ala Glu Asp Ala Ala Thr Tyr Tyr Cys
465                 470                 475                 480

Gln Gln Trp Ser Ser Asn Pro Leu Thr Phe Gly Ala Gly Thr Lys Leu
                485                 490                 495

Glu Leu Lys His His His His His His
                500                 505

<210> SEQ ID NO 3
<211> LENGTH: 1525
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
```

-continued

```
tgtacactcc gatatccagc tgacccagtc tccagcttct ttggctgtgt ctctagggca      60
gagggccacc atctcctgca aggccagcca agtgttgat tatgatggtg atagttattt     120
gaactggtac caacagattc caggacagcc acccaaactc ctcatctatg atgcatccaa    180
tctagtttct gggatcccac ccaggtttag tggcagtggg tctgggacag acttcaccct    240
caacatccat cctgtggaga aggtggatgc tgcaacctat cactgtcagc aaagtactga    300
ggatccgtgg acgttcggtg gagggaccaa gctcgagatc aaaggtggtg gtggttctgg    360
cggcggcggc tccggtggtg gtggttctca ggtgcagctg cagcagtctg ggctgagct     420 ggtgaggcct gggtcctcag tgaagatttc ctgcaaggct tctggctatg cattcagtag    480
ctactggatg aactgggtga agcagaggcc tggacagggt cttgagtgga ttggacagat    540
ttggcctgga gatggtgata ctaactacaa tggaaagttc aagggtaaag ccactctgac    600
tgcagacgaa tcctccagca cagcctacat gcaactcagc agcctagcat ctgaggactc    660
tgcggtctat ttctgtgcaa gacgggagac tacgacggta ggccgttatt actatgctat    720
ggactactgg ggccaaggga ccacggtcac cgtctcctcc ggaggtggtg gatccgacat    780
tcagctgacc cagtctccag caatcatgtc tgcatctcca ggggagaagg tcaccatgac    840
ctgcagagcc agttcaagtg taagttacat gaactggtac cagcagaagt caggcacctc    900
ccccaaaaga tggatttatg acacatccaa agtggcttct ggagtccctt atcgcttcag    960
tggcagtggg tctgggacct catactctct cacaatcagc agcatggagg ctgaagatgc   1020
tgccacttat tactgccaac agtggagtag taacccgctc acgttcggtg ctgggaccaa   1080
gctggagctg aaaggtggtg gtggttctgg cggcggcggc tccggtggtg gtggttctga   1140
tatcaaactg cagcagtcag gggctgaact ggcaagacct ggggcctcag tgaagatgtc   1200
ctgcaagact tctggctaca cctttactag gtacacgatg cactgggtaa acagaggcc    1260 tggacagggt ctggaatgga ttggatacat taatcctagc cgtggttata ctaattacaa   1320
tcagaagttc aaggacaagg ccacattgac tacagacaaa tcctccagca cagcctacat   1380
gcaactgagc agcctgacat ctgaggactc tgcagtctat tactgtgcaa gatattatga   1440
tgatcattac tgccttgact actggggcca aggcaccact ctcacagtct cctccgggca   1500
tcatcaccat catcattgag tcgac                                          1525
```

<210> SEQ ID NO 4
<211> LENGTH: 502
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
```

-continued

```
                85                  90                  95
Glu Asp Pro Trp Thr Phe Gly Gly Gly Thr Lys Leu Glu Ile Lys Gly
                100                 105                 110

Gly Gly Gly Ser Gly Gly Gly Ser Gly Gly Gly Ser Gln Val
            115                 120                 125

Gln Leu Gln Gln Ser Gly Ala Glu Leu Val Arg Pro Gly Ser Ser Val
            130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
            210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Gln Leu Thr Gln Ser Pro Ala Ile Met Ser Ala Ser Pro Gly Glu
                260                 265                 270

Lys Val Thr Met Thr Cys Arg Ala Ser Ser Ser Val Ser Tyr Met Asn
                275                 280                 285

Trp Tyr Gln Gln Lys Ser Gly Thr Ser Pro Lys Arg Trp Ile Tyr Asp
            290                 295                 300

Thr Ser Lys Val Ala Ser Gly Val Pro Tyr Arg Phe Ser Gly Ser Gly
305                 310                 315                 320

Ser Gly Thr Ser Tyr Ser Leu Thr Ile Ser Ser Met Glu Ala Glu Asp
                325                 330                 335

Ala Ala Thr Tyr Tyr Cys Gln Gln Trp Ser Ser Asn Pro Leu Thr Phe
                340                 345                 350

Gly Ala Gly Thr Lys Leu Glu Leu Lys Gly Gly Gly Ser Gly Gly
            355                 360                 365

Gly Gly Ser Gly Gly Gly Ser Asp Ile Lys Leu Gln Gln Ser Gly
            370                 375                 380

Ala Glu Leu Ala Arg Pro Gly Ala Ser Val Lys Met Ser Cys Lys Thr
385                 390                 395                 400

Ser Gly Tyr Thr Phe Thr Arg Tyr Thr Met His Trp Val Lys Gln Arg
                405                 410                 415

Pro Gly Gln Gly Leu Glu Trp Ile Gly Tyr Ile Asn Pro Ser Arg Gly
                420                 425                 430

Tyr Thr Asn Tyr Asn Gln Lys Phe Lys Asp Lys Ala Thr Leu Thr Thr
            435                 440                 445

Asp Lys Ser Ser Ser Thr Ala Tyr Met Gln Leu Ser Ser Leu Thr Ser
450                 455                 460

Glu Asp Ser Ala Val Tyr Tyr Cys Ala Arg Tyr Tyr Asp Asp His Tyr
465                 470                 475                 480

Cys Leu Asp Tyr Trp Gly Gln Gly Thr Thr Leu Thr Val Ser Ser Gly
                485                 490                 495

His His His His His His
            500
```

<210> SEQ ID NO 5
<211> LENGTH: 1528
<212> TYPE: DNA
<213> ORGANISM: Artificial Sequence
<220> FEATURE:
<223> OTHER INFORMATION: Description of Artificial Sequence: Synthetic construct

<400> SEQUENCE: 5

```
tgtacactcc caggtgcagc tgcagcagtc tggggctgag ctggtgaggc ctgggtcctc    60
agtgaagatt tcctgcaagg cttctggcta tgcattcagt agctactgga tgaactgggt   120
gaagcagagg cctggacagg gtcttgagtg gattggacag atttggcctg agatggtga    180
tactaactac aatggaaagt tcaagggtaa agccactctg actgcagacg aatcctccag   240
cacagcctac atgcaactca gcagcctagc atctgaggac tctgcggtct atttctgtgc   300
aagacgggag actacgacgg taggccgtta ttactatgct atggactact ggggccaagg   360
gaccacggtc accgtctcct ccggtggtgg tggttctggc ggcggcggct ccggtggtgg   420
tggttctgat atccagctga cccagtctcc agcttctttg ctgtgtctc tagggcagag   480
ggccaccatc tcctgcaagg ccagccaaag tgttgattat gatggtgata gttatttgaa   540
ctggtaccaa cagattccag acagccacc caaactcctc atctatgatg catccaatct   600
agtttctggg atcccaccca ggtttagtgg cagtgggtct gggacagact caccctcaa    660
catccatcct gtggagaagg tggatgctgc aacctatcac tgtcagcaaa gtactgagga   720
tccgtggacg ttcggtggag ggaccaagct cgagatcaaa tccgaggtg gtggatccga    780
cattcagctg acccagtctc cagcaatcat gtctgcatct ccaggggaga aggtcaccat   840
gacctgcaga gccagttcaa gtgtaagtta catgaactgg taccagcaga agtcaggcac   900
ctcccccaaa agatggattt atgacacatc caaagtggct tctggagtcc cttatcgctt   960
cagtggcagt gggtctggga cctcatactc tctcacaatc agcagcatgg aggctgaaga  1020
tgctgccact tattactgcc aacagtggag tagtaacccg ctcacgttcg gtgctgggac  1080
caagctggag ctgaaaggtg gtggtggttc tggcggcggc ggctccggtg tggtggttc   1140
tgatatcaaa ctgcagcagt caggggctga actggcaaga cctggggcct cagtgaagat  1200
gtcctgcaag acttctggct acacctttac taggtacacg atgcactggg taaaacagag  1260
gcctggacag ggtctggaat ggattggata cattaatcct agccgtggtt atactaatta  1320
caatcagaag ttcaaggaca aggccacatt gactacagac aaatcctcca gcacagccta  1380
catgcaactg agcagcctga catctgagga ctctgcagtc tattactgtg caagatatta  1440
tgatgatcat tactgccttg actactgggg ccaaggcacc actctcacag tctcctccgg  1500
gcatcatcac catcatcatt gagtcgac                                      1528
```

<210> SEQ ID NO 6
<211> LENGTH: 503
<212> TYPE: PRT
<213> ORGANISM: Artificial Sequence
<220> FEATURE:
<223> OTHER INFORMATION: Description of Artificial Sequence: Synthetic construct

<400> SEQUENCE: 6

```
Gln Val Gln Leu Gln Gln Ser Gly Ala Glu Leu Val Arg Pro Gly Ser
  1               5                  10                  15

Ser Val Lys Ile Ser Cys Lys Ala Ser Gly Tyr Ala Phe Ser Ser Tyr
```

-continued

```
                 20                  25                  30
Trp Met Asn Trp Val Lys Gln Arg Pro Gly Gln Gly Leu Glu Trp Ile
         35                  40                  45
Gly Gln Ile Trp Pro Gly Asp Gly Asp Thr Asn Tyr Asn Gly Lys Phe
     50                  55                  60
Lys Gly Lys Ala Thr Leu Thr Ala Asp Glu Ser Ser Ser Thr Ala Tyr
 65                  70                  75                  80
Met Gln Leu Ser Ser Leu Ala Ser Glu Asp Ser Ala Val Tyr Phe Cys
                 85                  90                  95
Ala Arg Arg Glu Thr Thr Thr Val Gly Arg Tyr Tyr Tyr Ala Met Asp
            100                 105                 110
Tyr Trp Gly Gln Gly Thr Thr Val Thr Val Ser Ser Gly Gly Gly Gly
        115                 120                 125
Ser Gly Gly Gly Gly Ser Gly Gly Gly Ser Asp Ile Gln Leu Thr
    130                 135                 140
Gln Ser Pro Ala Ser Leu Ala Val Ser Leu Gly Gln Arg Ala Thr Ile
145                 150                 155                 160
Ser Cys Lys Ala Ser Gln Ser Val Asp Tyr Asp Gly Asp Ser Tyr Leu
                165                 170                 175
Asn Trp Tyr Gln Gln Ile Pro Gly Gln Pro Pro Lys Leu Leu Ile Tyr
            180                 185                 190
Asp Ala Ser Asn Leu Val Ser Gly Ile Pro Pro Arg Phe Ser Gly Ser
        195                 200                 205
Gly Ser Gly Thr Asp Phe Thr Leu Asn Ile His Pro Val Glu Lys Val
    210                 215                 220
Asp Ala Ala Thr Tyr His Cys Gln Gln Ser Thr Glu Asp Pro Trp Thr
225                 230                 235                 240
Phe Gly Gly Gly Thr Lys Leu Glu Ile Lys Ser Gly Gly Gly Gly Ser
                245                 250                 255
Asp Ile Gln Leu Thr Gln Ser Pro Ala Ile Met Ser Ala Ser Pro Gly
            260                 265                 270
Glu Lys Val Thr Met Thr Cys Arg Ala Ser Ser Ser Val Ser Tyr Met
        275                 280                 285
Asn Trp Tyr Gln Gln Lys Ser Gly Thr Ser Pro Lys Arg Trp Ile Tyr
    290                 295                 300
Asp Thr Ser Lys Val Ala Ser Gly Val Pro Tyr Arg Phe Ser Gly Ser
305                 310                 315                 320
Gly Ser Gly Thr Ser Tyr Ser Leu Thr Ile Ser Ser Met Glu Ala Glu
                325                 330                 335
Asp Ala Ala Thr Tyr Tyr Cys Gln Gln Trp Ser Ser Asn Pro Leu Thr
            340                 345                 350
Phe Gly Ala Gly Thr Lys Leu Glu Leu Lys Gly Gly Gly Gly Ser Gly
        355                 360                 365
Gly Gly Gly Ser Gly Gly Gly Gly Ser Asp Ile Lys Leu Gln Gln Ser
    370                 375                 380
Gly Ala Glu Leu Ala Arg Pro Gly Ala Ser Val Lys Met Ser Cys Lys
385                 390                 395                 400
Thr Ser Gly Tyr Thr Phe Thr Arg Tyr Thr Met His Trp Val Lys Gln
                405                 410                 415
Arg Pro Gly Gln Gly Leu Glu Trp Ile Gly Tyr Ile Asn Pro Ser Arg
            420                 425                 430
Gly Tyr Thr Asn Tyr Asn Gln Lys Phe Lys Asp Lys Ala Thr Leu Thr
        435                 440                 445
```

Thr Asp Lys Ser Ser Ser Thr Ala Tyr Met Gln Leu Ser Ser Leu Thr
    450                 455                 460
Ser Glu Asp Ser Ala Val Tyr Tyr Cys Ala Arg Tyr Tyr Asp Asp His
465                 470                 475                 480
Tyr Cys Leu Asp Tyr Trp Gly Gln Gly Thr Thr Leu Thr Val Ser Ser
                485                 490                 495
Gly His His His His His
            500

<210> SEQ ID NO 7
<211> LENGTH: 1531
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
tgtacactcc gacattcagc tgacccagtc tccagcaatc atgtctgcat ctccagggga      60
gaaggtcacc atgacctgca gagccagttc aagtgtaagt tacatgaact ggtaccagca     120
gaagtcaggc acctccccca aaagatggat ttatgacaca tccaaagtgg cttctggagt     180
cccttatcgc ttcagtggca gtgggtctgg gacctcatac tctctcacaa tcagcagcat     240
ggaggctgaa gatgctgcca cttattactg ccaacagtgg agtagtaacc cgctcacgtt     300
cggtgctggg accaagctgg agctgaaagg tggtggtggt tctggcggcg cggctccgg      360
tggtggtggt tctgatatca aactgcagca gtcaggggct gaactggcaa gacctggggc     420
ctcagtgaag atgtcctgca agacttctgg ctacaccttt actaggtaca cgatgcactg     480
ggtaaaacag aggcctggac agggtctgga atggattgga tacattaatc ctagccgtgg     540
ttatactaat tacaatcaga agttcaagga caaggccaca ttgactacag acaaatcctc     600
cagcacagcc tacatgcaac tgagcagcct gacatctgag gactctgcag tctattactg     660
tgcaagatat tatgatgatc attactgcct tgactactgg ggccaaggca ccactctcac     720
agtctcctca tccggaggtg gtggatccca ggtgcagctg cagcagtctg gggctgagct     780
ggtgaggcct gggtcctcag tgaagatttc ctgcaaggct tctggctatg cattcagtag     840
ctactggatg aactgggtga agcagaggcc tggacagggt cttgagtgga ttggacagat     900
ttggcctgga gatggtgata ctaactacaa tggaaagttc aagggtaaag ccactctgac     960
tgcagacgaa tcctccagca cagcctacat gcaactcagc agcctagcat ctgaggactc    1020
tgcggtctat ttctgtgcaa gacgggagac tacgacggta ggccgttatt actatgctat    1080
ggactactgg ggccaaggga ccacggtcac cgtctcctcc ggtggtggtg ttctggcgg     1140
cggcggctcc ggtggtggtg ttctgatat ccagctgacc cagtctccag cttctttggc    1200
tgtgtctcta gggcagaggg ccaccatctc ctgcaaggcc agccaaagtg ttgattatga    1260
tggtgatagt tatttgaact ggtaccaaca gattccagga cagccaccca aactcctcat    1320
ctatgatgca tccaatctag tttctgggat cccacccagg tttagtggca gtgggtctgg    1380
gacagacttc accctcaaca tccatcctgt ggagaaggtg gatgctgcaa cctatcactg    1440
tcagcaaagt actgaggatc cgtggacgtt cggtggaggg accaagctcg agatcaaatc    1500
cgggcatcat caccatcatc attgagtcga c                                   1531

<210> SEQ ID NO 8
<211> LENGTH: 504

```
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Asp Ile Lys Leu Gln Gln Ser
        115                 120                 125

Gly Ala Glu Leu Ala Arg Pro Gly Ala Ser Val Lys Met Ser Cys Lys
130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240

Ser Gly Gly Gly Gly Ser Gln Val Gln Leu Gln Gln Ser Gly Ala Glu
                245                 250                 255

Leu Val Arg Pro Gly Ser Ser Val Lys Ile Ser Cys Lys Ala Ser Gly
            260                 265                 270

Tyr Ala Phe Ser Ser Tyr Trp Met Asn Trp Val Lys Gln Arg Pro Gly
        275                 280                 285

Gln Gly Leu Glu Trp Ile Gly Gln Ile Trp Pro Gly Asp Gly Asp Thr
    290                 295                 300

Asn Tyr Asn Gly Lys Phe Lys Gly Lys Ala Thr Leu Thr Ala Asp Glu
305                 310                 315                 320

Ser Ser Ser Thr Ala Tyr Met Gln Leu Ser Ser Leu Ala Ser Glu Asp
                325                 330                 335

Ser Ala Val Tyr Phe Cys Ala Arg Arg Glu Thr Thr Thr Val Gly Arg
            340                 345                 350

Tyr Tyr Tyr Ala Met Asp Tyr Trp Gly Gln Gly Thr Thr Val Thr Val
        355                 360                 365

Ser Ser Gly Gly Gly Gly Ser Gly Gly Gly Gly Ser Gly Gly Gly Gly
    370                 375                 380
```

```
Ser Asp Ile Gln Leu Thr Gln Ser Pro Ala Ser Leu Ala Val Ser Leu
385                 390                 395                 400

Gly Gln Arg Ala Thr Ile Ser Cys Lys Ala Ser Gln Ser Val Asp Tyr
            405                 410                 415

Asp Gly Asp Ser Tyr Leu Asn Trp Tyr Gln Gln Ile Pro Gly Gln Pro
            420                 425                 430

Pro Lys Leu Leu Ile Tyr Asp Ala Ser Asn Leu Val Ser Gly Ile Pro
            435                 440                 445

Pro Arg Phe Ser Gly Ser Gly Ser Gly Thr Asp Phe Thr Leu Asn Ile
    450                 455                 460

His Pro Val Glu Lys Val Asp Ala Ala Thr Tyr His Cys Gln Gln Ser
465                 470                 475                 480

Thr Glu Asp Pro Trp Thr Phe Gly Gly Gly Thr Lys Leu Glu Ile Lys
                485                 490                 495

Ser Gly His His His His His His
            500
```

<210> SEQ ID NO 9
<211> LENGTH: 1531
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9

```
tgtacactcc gatatcaaac tgcagcagtc aggggctgaa ctggcaagac ctggggcctc      60
agtgaagatg tcctgcaaga cttctggcta cacctttact aggtacacga tgcactgggt     120
aaaacagagg cctggacagg gtctggaatg gattggatac attaatccta gccgtggtta     180
tactaattac aatcagaagt tcaaggacaa ggccacattg actacagaca atcctccag      240
cacagcctac atgcaactga gcagcctgac atctgaggac tctgcagtct attactgtgc     300
aagatattat gatgatcatt actgccttga ctactgggc caaggcacca ctctcacagt      360
ctcctcaggt ggtggtggtt ctggcggcgg cggctccggt ggtggtggtt ctgacattca     420
gctgacccag tctccagcaa tcatgtctgc atctccaggg gagaaggtca ccatgacctg     480
cagagccagt tcaagtgtaa gttacatgaa ctggtaccag cagaagtcag gcacctcccc     540
caaaagatgg atttatgaca catccaaagt ggcttctgga gtcccttatc gcttcagtgg     600
cagtgggtct gggacctcat actctctcac aatcagcagc atggaggctg aagatgctgc     660
cacttattac tgccaacagt ggagtagtaa cccgctcacg ttcggtgctg gaccaagct      720
ggagctgaaa tccggaggtg gtggatccca ggtgcagctg cagcagtctg ggctgagct      780
ggtgaggcct gggtcctcag tgaagatttc ctgcaaggct tctggctatg cattcagtag     840
ctactggatg aactgggtga agcagaggcc tggacagggt cttgagtgga ttggacagat     900
ttggcctgga gatggtgata ctaactacaa tggaaagttc aagggtaaag ccactctgac     960
tgcagacgaa tcctccagca cagcctacat gcaactcagc agcctagcat ctgaggactc    1020
tgcggtctat ttctgtgcaa gacgggagac tacgacggta ggccgttatt actatgctat    1080
ggactactgg ggccaaggga ccacggtcac cgtctcctcc ggtggtggtg gttctggcgg    1140
cggcggctcc ggtggtggtg gttctgatat ccagctgacc cagtctccag cttctttggc    1200
tgtgtctcta gggcagaggg ccaccatctc ctgcaaggcc agccaaagtg ttgattatga    1260
tggtgatagt tatttgaact ggtaccaaca gattccagga cagccaccca aactcctcat    1320
```

```
ctatgatgca tccaatctag tttctgggat cccacccagg tttagtggca gtgggtctgg    1380
gacagacttc accctcaaca tccatcctgt ggagaaggtg gatgctgcaa cctatcactg    1440
tcagcaaagt actgaggatc cgtggacgtt cggtggaggg accaagctcg agatcaaatc    1500
cgggcatcat caccatcatc attgagtcga c                                   1531
```

<210> SEQ ID NO 10
<211> LENGTH: 504
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Gln Val Gln Leu Gln Gln Ser Gly Ala Glu
                245                 250                 255

Leu Val Arg Pro Gly Ser Ser Val Lys Ile Ser Cys Lys Ala Ser Gly
            260                 265                 270

Tyr Ala Phe Ser Ser Tyr Trp Met Asn Trp Val Lys Gln Arg Pro Gly
        275                 280                 285

Gln Gly Leu Glu Trp Ile Gly Gln Ile Trp Pro Gly Asp Gly Asp Thr
    290                 295                 300

Asn Tyr Asn Gly Lys Phe Lys Gly Lys Ala Thr Leu Thr Ala Asp Glu
305                 310                 315                 320
```

```
Ser Ser Ser Thr Ala Tyr Met Gln Leu Ser Ser Leu Ala Ser Glu Asp
            325                 330                 335

Ser Ala Val Tyr Phe Cys Ala Arg Arg Glu Thr Thr Thr Val Gly Arg
        340                 345                 350

Tyr Tyr Tyr Ala Met Asp Tyr Trp Gly Gln Gly Thr Thr Val Thr Val
            355                 360                 365

Ser Ser Gly Gly Gly Gly Ser Gly Gly Gly Gly Ser Gly Gly Gly Gly
        370                 375                 380

Ser Asp Ile Gln Leu Thr Gln Ser Pro Ala Ser Leu Ala Val Ser Leu
385                 390                 395                 400

Gly Gln Arg Ala Thr Ile Ser Cys Lys Ala Ser Gln Ser Val Asp Tyr
                405                 410                 415

Asp Gly Asp Ser Tyr Leu Asn Trp Tyr Gln Gln Ile Pro Gly Gln Pro
            420                 425                 430

Pro Lys Leu Leu Ile Tyr Asp Ala Ser Asn Leu Val Ser Gly Ile Pro
        435                 440                 445

Pro Arg Phe Ser Gly Ser Gly Ser Gly Thr Asp Phe Thr Leu Asn Ile
    450                 455                 460

His Pro Val Glu Lys Val Asp Ala Ala Thr Tyr His Cys Gln Gln Ser
465                 470                 475                 480

Thr Glu Asp Pro Trp Thr Phe Gly Gly Gly Thr Lys Leu Glu Ile Lys
                485                 490                 495

Ser Gly His His His His His His
            500

<210> SEQ ID NO 11
<211> LENGTH: 1528
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11
tgtacactcc gacattcagc tgacccagtc tccagcaatc atgtctgcat ctccagggga      60
gaaggtcacc atgacctgca gagccagttc aagtgtaagt tacatgaact ggtaccagca     120
gaagtcaggc acctccccca aaagatggat ttatgacaca tccaaagtgg cttctggagt     180
cccttatcgc ttcagtggca gtgggtctgg gacctcatac tctctcacaa tcagcagcat     240
ggaggctgaa gatgctgcca cttattactg ccaacagtgg agtagtaacc cgctcacgtt     300
cggtgctggg accaagctgg agctgaaagg tggtggtggt tctggcggcg gcggctccgg     360
tggtggtggt tctgatatca aactgcagca gtcaggggct gaactggcaa gacctggggc     420
ctcagtgaag atgtcctgca agacttctgg ctacaccttt actaggtaca cgatgcactg     480
ggtaaaacag aggcctggac agggtctgga atggattgga tacattaatc ctagccgtgg     540
ttatactaat tacaatcaga gttcaagga caaggccaca ttgactacag acaaatcctc     600
cagcacagcc tacatgcaac tgagcagcct gacatctgag gactctgcag tctattactg     660
tgcaagatat tatgatgatc attactgcct tgactactgg ggccaaggca ccactctcac     720
agtctcctca tccggaggtg gtggatccga tatccagctg acccagtctc agcttctttt     780
ggctgtgtct ctagggcaga gggccaccat ctcctgcaag gccagccaaa gtgttgatta     840
tgatggtgat agttatttga actggtacca acagattcca ggacagccac ccaaactcct     900
catctatgat gcatccaatc tagtttctgg gatcccaccc aggtttagtg gcagtgggtc     960
```

```
tgggacagac ttcaccctca acatccatcc tgtggagaag gtggatgctg caacctatca    1020
ctgtcagcaa agtactgagg atccgtggac gttcggtgga gggaccaagc tcgagatcaa    1080
aggtggtggt ggttctggcg gcggcggctc cggtggtggt ggttctcagg tgcagctgca    1140
gcagtctggg gctgagctgg tgaggcctgg gtcctcagtg aagatttcct gcaaggcttc    1200
tggctatgca ttcagtagct actggatgaa ctgggtgaag cagaggcctg acagggtct     1260 tgagtggatt ggacagattt ggcctggaga tggtgatact aactacaatg aaagttcaa     1320 gggtaaagcc actctgactg cagacgaatc ctccagcaca gcctacatgc aactcagcag    1380
cctagcatct gaggactctg cggtctattt ctgtgcaaga cgggagacta cgacggtagg    1440
ccgttattac tatgctatgg actactgggg ccaagggacc acggtcaccg tctcctccgg    1500
gcatcatcac catcatcatt gagtcgac                                       1528
```

<210> SEQ ID NO 12
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Asp Ile Lys Leu Gln Gln Ser
        115                 120                 125

Gly Ala Glu Leu Ala Arg Pro Gly Ala Ser Val Lys Met Ser Cys Lys
    130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240

Ser Gly Gly Gly Gly Ser Asp Ile Gln Leu Thr Gln Ser Pro Ala Ser
                245                 250                 255
```

Leu Ala Val Ser Leu Gly Gln Arg Ala Thr Ile Ser Cys Lys Ala Ser
            260                 265                 270

Gln Ser Val Asp Tyr Asp Gly Asp Ser Tyr Leu Asn Trp Tyr Gln Gln
        275                 280                 285

Ile Pro Gly Gln Pro Lys Leu Leu Ile Tyr Asp Ala Ser Asn Leu
    290                 295                 300

Val Ser Gly Ile Pro Pro Arg Phe Ser Gly Ser Gly Ser Gly Thr Asp
305                 310                 315                 320

Phe Thr Leu Asn Ile His Pro Val Glu Lys Val Asp Ala Ala Thr Tyr
                325                 330                 335

His Cys Gln Gln Ser Thr Glu Asp Pro Trp Thr Phe Gly Gly Gly Thr
            340                 345                 350

Lys Leu Glu Ile Lys Gly Gly Gly Ser Gly Gly Gly Gly Ser Gly
        355                 360                 365

Gly Gly Gly Ser Gln Val Gln Leu Gln Gln Ser Gly Ala Glu Leu Val
    370                 375                 380

Arg Pro Gly Ser Ser Val Lys Ile Ser Cys Lys Ala Ser Gly Tyr Ala
385                 390                 395                 400

Phe Ser Ser Tyr Trp Met Asn Trp Val Lys Gln Arg Pro Gly Gln Gly
                405                 410                 415

Leu Glu Trp Ile Gly Gln Ile Trp Pro Gly Asp Gly Asp Thr Asn Tyr
            420                 425                 430

Asn Gly Lys Phe Lys Gly Lys Ala Thr Leu Thr Ala Asp Glu Ser Ser
        435                 440                 445

Ser Thr Ala Tyr Met Gln Leu Ser Ser Leu Ala Ser Glu Asp Ser Ala
    450                 455                 460

Val Tyr Phe Cys Ala Arg Arg Glu Thr Thr Thr Val Gly Arg Tyr Tyr
465                 470                 475                 480

Tyr Ala Met Asp Tyr Trp Gly Gln Gly Thr Thr Val Thr Val Ser Ser
                485                 490                 495

Gly His His His His His His
            500

<210> SEQ ID NO 13
<211> LENGTH: 1528
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13
tgtacactcc gatatcaaac tgcagcagtc aggggctgaa ctggcaagac ctggggcctc    60
agtgaagatg tcctgcaaga cttctggcta cacctttact aggtacacga tgcactgggt   120
aaaacagagg cctggacagg gtctggaatg gattggatac attaatccta gccgtggtta   180
tactaattac aatcagaagt tcaaggacaa ggccacattg actacagaca atcctccag    240 cacagcctac atgcaactga gcagcctgac atctgaggac tctgcagtct attactgtgc   300
aagatattat gatgatcatt actgccttga ctactgggc caaggcacca ctctcacagt    360
ctcctcaggt ggtggtggtt ctggcggcgg cggctccggt ggtggtggtt ctgacattca   420
gctgacccag tctccagcaa tcatgtctgc atctccaggg gagaaggtca ccatgacctg   480
cagagccagt tcaagtgtaa gttacatgaa ctggtaccag cagaagtcag gcacctcccc   540
caaaagatgg atttatgaca catccaaagt ggcttctgga gtcccttatc gcttcagtgg   600

```
cagtgggtct gggacctcat actctctcac aatcagcagc atggaggctg aagatgctgc    660
cacttattac tgccaacagt ggagtagtaa cccgctcacg ttcggtgctg ggaccaagct    720
ggagctgaaa tccggaggtg gtggatccga tatccagctg acccagtctc cagcttcttt    780
ggctgtgtct ctagggcaga gggccaccat ctcctgcaag gccagccaaa gtgttgatta    840
tgatggtgat agttatttga actggtacca acagattcca ggacagccac ccaaactcct    900
catctatgat gcatccaatc tagtttctgg gatcccaccc aggtttagtg gcagtgggtc    960
tgggacagac ttcacccctca acatccatcc tgtggagaag gtggatgctg caacctatca   1020
ctgtcagcaa agtactgagg atccgtggac gttcggtgga gggaccaagc tcgagatcaa   1080
aggtggtggt ggttctggcg gcggcggctc cggtggtggt ggttctcagg tgcagctgca   1140
gcagtctggg gctgagctgg tgaggcctgg gtcctcagtg aagatttcct gcaaggcttc   1200
tggctatgca ttcagtagct actggatgaa ctgggtgaag cagaggcctg gacagggtct   1260
tgagtggatt ggacagattt ggcctggaga tggtgatact aactacaatg gaaagttcaa   1320
gggtaaagcc actctgactg cagacgaatc ctccagcaca gcctacatgc aactcagcag   1380
cctagcatct gaggactctg cggtctattt ctgtgcaaga cgggagacta cgacggtagg   1440
ccgttattac tatgctatgg actactgggg ccaagggacc acggtcaccg tctcctccgg   1500
gcatcatcac catcatcatt gagtcgac                                       1528
```

<210> SEQ ID NO 14
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190
```

Tyr Arg Phe Ser Gly Ser Gly Ser Gly Thr Ser Tyr Ser Leu Thr Ile
            195                 200                 205

Ser Ser Met Glu Ala Glu Asp Ala Ala Thr Tyr Tyr Cys Gln Gln Trp
        210                 215                 220

Ser Ser Asn Pro Leu Thr Phe Gly Ala Gly Thr Lys Leu Glu Leu Lys
225                 230                 235                 240

Ser Gly Gly Gly Ser Asp Ile Gln Leu Thr Gln Ser Pro Ala Ser
                245                 250                 255

Leu Ala Val Ser Leu Gly Gln Arg Ala Thr Ile Ser Cys Lys Ala Ser
            260                 265                 270

Gln Ser Val Asp Tyr Asp Gly Asp Ser Tyr Leu Asn Trp Tyr Gln Gln
        275                 280                 285

Ile Pro Gly Gln Pro Pro Lys Leu Leu Ile Tyr Asp Ala Ser Asn Leu
    290                 295                 300

Val Ser Gly Ile Pro Pro Arg Phe Ser Gly Ser Gly Ser Gly Thr Asp
305                 310                 315                 320

Phe Thr Leu Asn Ile His Pro Val Glu Lys Val Asp Ala Ala Thr Tyr
                325                 330                 335

His Cys Gln Gln Ser Thr Glu Asp Pro Trp Thr Phe Gly Gly Gly Thr
            340                 345                 350

Lys Leu Glu Ile Lys Gly Gly Gly Gly Ser Gly Gly Gly Gly Ser Gly
        355                 360                 365

Gly Gly Gly Ser Gln Val Gln Leu Gln Gln Ser Gly Ala Glu Leu Val
    370                 375                 380

Arg Pro Gly Ser Ser Val Lys Ile Ser Cys Lys Ala Ser Gly Tyr Ala
385                 390                 395                 400

Phe Ser Ser Tyr Trp Met Asn Trp Val Lys Gln Arg Pro Gly Gln Gly
                405                 410                 415

Leu Glu Trp Ile Gly Gln Ile Trp Pro Gly Asp Gly Asp Thr Asn Tyr
            420                 425                 430

Asn Gly Lys Phe Lys Gly Lys Ala Thr Leu Thr Ala Asp Glu Ser Ser
        435                 440                 445

Ser Thr Ala Tyr Met Gln Leu Ser Ser Leu Ala Ser Glu Asp Ser Ala
    450                 455                 460

Val Tyr Phe Cys Ala Arg Arg Glu Thr Thr Thr Val Gly Arg Tyr Tyr
465                 470                 475                 480

Tyr Ala Met Asp Tyr Trp Gly Gln Gly Thr Thr Val Thr Val Ser Ser
                485                 490                 495

Gly His His His His His
            500

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cttccggagg tggtggatcc gacattcagc tgacccag                            38

<210> SEQ ID NO 16
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 16
cctccggagg agactgtgag agtgg                                          25

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cttccggagg tggtggatcc caggtgcagc tgcagcag                            38

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cctccggatt tgatctcgag cttgg                                          25

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttccggagg tggtggatcc gatatccagc tgacc                               35

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aggtgtacac tccgatatca aactgcagca g                                   31

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggagccgccg ccgccagaac caccaccacc tgaggagact gtgagagtgg               50

<210> SEQ ID NO 22
<211> LENGTH: 53
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 22
ggcggcggcg gctccggtgg tggtggttct gacattcagc tgacccagtc tcc         53

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aatccggatt tcagctccag cttgg                                         25

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aggtgtacac tcccaggtgc agctgcagca g                                  31

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggagccgccg ccgccagaac caccaccacc ggaggagacg gtgaccgtgg              50

<210> SEQ ID NO 26
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggcggcggcg gctccggtgg tggtggttct gatatccagc tgacccagtc tcc          53

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aatccggatt tgatctcgag cttgg                                         25

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
aatccggagg agacggtgac cgtggtccct tggccccag          39

<210> SEQ ID NO 29
<211> LENGTH: 1587
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 29
gaattccacc atgggatgga gctgtatcat cctcttcttg gtagcaacag ctacaggtgt     60
acactccgat atccagctga cccagtctcc agcttctttg gctgtgtctc tagggcagag   120
ggccaccatc tcctgcaagg ccagccaaag tgttgattat gatggtgata gttatttgaa   180
ctggtaccaa cagattccag acagccacc caaactcctc atctatgatg catccaatct   240
agtttctggg atcccaccca ggtttagtgg cagtgggtct gggacagact tcaccctcaa   300
catccatcct gtggagaagg tggatgctgc aacctatcac tgtcagcaaa gtactgagga   360
tccgtggacg ttcggtggag ggaccaagct cgagatcaaa ggtggtggtg ttctggcgg   420
cggcggctcc ggtggtggtg ttctcaggt gcagctgcag cagtctgggg ctgagctggt   480
gaggcctggg tcctcagtga agatttcctg caaggcttct ggctatgcat tcagtagcta   540
ctggatgaac tgggtgaagc agaggcctgg acagggtctt gagtggattg acagatttg   600
gcctggagat ggtgatacta actacaatgg aaagttcaag ggtaaagcca ctctgactgc   660
agacgaatcc tccagcacag cctacatgca actcagcagc ctagcatctg aggactctgc   720
ggtctatttc tgtgcaagac gggagactac gacggtaggc cgttattact atgctatgga   780
ctactggggc caaggaccac cggtcaccgt ctcctccgga ggtggtggat ccgatatcaa   840
actgcagcag tcaggggctg aactggcaag acctggggcc tcagtgaaga tgtcctgcaa   900
gacttctggc tacacctta ctaggtacac gatgcactgg gtaaaacaga ggcctggaca   960
gggtctggaa tggattggat acattaatcc tagccgtggt tatactaatt acaatcagaa  1020
gttcaaggac aaggccacat tgactacaga caaatcctcc agcacagcct acatgcaact  1080
gagcagcctg acatctgagg actctgcagt ctattactgt gcaagatatt atgatgatca  1140
ttactgcctt gactactggg gccaaggcac cactctcaca gtctcctcag tcgaaggtgg  1200
aagtggaggt tctggtggaa gtggaggttc aggtggagtc gacgacattc agctgaccca  1260
gtctccagca atcatgtctg catctccagg ggagaaggtc accatgacct gcagagccag  1320
ttcaagtgta agttacatga actggtacca gcagaagtca ggcacctccc ccaaaagatg  1380
gatttatgac acatccaaag tggcttctgg agtcccttat cgcttcagtg gcagtgggtc  1440
tgggacctca tactctctca caatcagcag catggaggct gaagatgctg ccacttatta  1500
ctgccaacag tggagtagta acccgctcac gttcggtgct gggaccaagc tggagctgaa  1560
acatcatcac catcatcatt agtcgac                                      1587

<210> SEQ ID NO 30
<211> LENGTH: 504
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
    195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
    275                 280                 285

Met His Trp Val Lys Gln Arg Pro Gly Gln Gly Leu Glu Trp Ile Gly
290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
    355                 360                 365

Thr Leu Thr Val Ser Ser Val Glu Gly Gly Ser Gly Gly Ser Gly Gly
370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
```

-continued

```
             405                 410                 415
Ala Ser Ser Val Ser Tyr Met Asn Trp Tyr Gln Gln Lys Ser Gly
        420                 425                 430

Thr Ser Pro Lys Arg Trp Ile Tyr Asp Thr Ser Lys Val Ala Ser Gly
            435                 440                 445

Val Pro Tyr Arg Phe Ser Gly Ser Gly Ser Gly Thr Ser Tyr Ser Leu
        450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys His His His His His His
            500

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aggtgtacac tccgacattc agctgaccca gtctc                              35

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagccgccg ccgccagaac caccaccacc tttcagctcc agcttggtcc              50

<210> SEQ ID NO 33
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggcggcggcg gctccggtgg tggtggttct gatatcaaac tgcagcagtc agg          53

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aatccggatg aggagactgt gagagtggtg                                    30

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 35
cctccggagg agacggtgac cgtgg                                           25

<210> SEQ ID NO 36
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tctagaattc ttcgaatccg gaggtggtgg atccgatatc cccgggcatc atcaccatca    60
tcattgagtc gac                                                        73

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaagcacgcg tagatatckt gmtsacccaa wctcca                               36

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaagatggat ccagcggccg cagcatcagc                                      30

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cagccggcca tggcgcaggt scagctgcag sag                                  33

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
accaggggcc agtggataga caagcttggg tgtcgtttt                            39

<210> SEQ ID NO 41
<211> LENGTH: 37
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 41
aggtgtacac tccgatatcc agctgaccca gtctcca                              37

<210> SEQ ID NO 42
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggagccgccg ccgccagaac caccaccacc tttgatctcg agcttggtcc c              51

<210> SEQ ID NO 43
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggcggcggcg gctccggtgg tggtggttct caggtsmarc tgcagsagtc wgg            53

<210> SEQ ID NO 44
<211> LENGTH: 750
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 44
caggtgcagc tgcagcagtc tggggctgag ctggtgaggc ctgggtcctc agtgaagatt     60
tcctgcaagg cttctggcta tgcattcagt agctactgga tgaactgggt gaagcagagg    120
cctggacagg gtcttgagtg gattggacag atttggcctg agatggtgta ctaactac      180 aatggaaagt tcaagggtaa agccactctg actgcagacg aatcctccag cacagcctac    240
atgcaactca gcagcctagc atctgaggac tctgcggtct atttctgtgc aagacgggag    300
actacgacgg taggccgtta ttactatgct atggactact ggggccaagg gaccacggtc    360
accgtctcct ccggtggtgg tggttctggc ggcggcggct ccggtggtgg tggttctgat    420
atccagctga cccagtctcc agcttctttg gctgtgtctc tagggcagag ggccaccatc    480
tcctgcaagg ccagccaaag tgttgattat gatggtgata gttatttgaa ctggtaccaa    540
cagattccag acagccacc caaactcctc atctatgatg catccaatct agtttctggg    600
atcccaccca ggtttagtgg cagtgggtct gggacagact caccctcaa catccatcct     660 gtggagaagg tggatgctgc aacctatcac tgtcagcaaa gtactgagga tccgtggacg    720
ttcggtggag ggaccaagct cgagatcaaa                                     750

<210> SEQ ID NO 45
<211> LENGTH: 250
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 45

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ala Ser Leu Ala Val Ser Leu Gly Gln Arg Ala Thr Ile
145                 150                 155                 160

Ser Cys Lys Ala Ser Gln Ser Val Asp Tyr Asp Gly Asp Ser Tyr Leu
                165                 170                 175

Asn Trp Tyr Gln Gln Ile Pro Gly Gln Pro Pro Lys Leu Leu Ile Tyr
            180                 185                 190

Asp Ala Ser Asn Leu Val Ser Gly Ile Pro Pro Arg Phe Ser Gly Ser
        195                 200                 205

Gly Ser Gly Thr Asp Phe Thr Leu Asn Ile His Pro Val Glu Lys Val
    210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys
                245                 250

<210> SEQ ID NO 46
<211> LENGTH: 729
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 46
gatatcaaac tgcagcagtc aggggctgaa ctggcaagac tggggcctc agtgaagatg      60 tcctgcaaga cttctggcta cacctttact aggtacacga tgcactgggt aaaacagagg     120
cctggacagg gtctggaatg gattggatac attaatccta gccgtggtta tactaattac     180
aatcagaagt tcaaggacaa ggccacattg actacagaca atcctccag cacagcctac     240 atgcaactga gcagcctgac atctgaggac tctgcagtct attactgtgc aagatattat     300
gatgatcatt actgccttga ctactggggc caaggcacca ctctcacagt ctcctcagtc     360
gaaggtggaa gtggaggttc tggtggaagt ggaggttcag gtggagtcga cgacattcag     420
ctgacccagt ctccagcaat catgtctgca tctccagggg agaaggtcac catgacctgc     480
agagccagtt caagtgtaag ttacatgaac tggtaccagc agaagtcagg cacctcccc     540

```
aaaagatgga tttatgacac atccaaagtg gcttctggag tcccttatcg cttcagtggc    600
agtgggtctg ggacctcata ctctctcaca atcagcagca tggaggctga agatgctgcc    660
acttattact gccaacagtg gagtagtaac ccgctcacgt tcggtgctgg gaccaagctg    720
gagctgaaa                                                            729
```

<210> SEQ ID NO 47
<211> LENGTH: 243
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 47

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys
```

<210> SEQ ID NO 48
<211> LENGTH: 750
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 48

```
gatatccagc tgacccagtc tccagcttct ttggctgtgt ctctagggca gagggccacc    60
```

```
atctcctgca aggccagcca aagtgttgat tatgatggtg atagttattt gaactggtac      120
caacagattc caggacagcc acccaaactc ctcatctatg atgcatccaa tctagtttct      180
gggatcccac ccaggtttag tggcagtggg tctgggacag acttcaccct caacatccat      240
cctgtggaga aggtggatgc tgcaacctat cactgtcagc aaagtactga ggatccgtgg      300
acgttcggtg gagggaccaa gctcgagatc aaaggtggtg gtggttctgg cggcggcggc      360
tccggtggtg gtggttctca ggtgcagctg cagcagtctg ggctgagct ggtgaggcct       420 gggtcctcag tgaagatttc ctgcaaggct tctggctatg cattcagtag ctactggatg      480
aactgggtga agcagaggcc tggacagggt cttgagtgga ttggacagat ttggcctgga      540
gatggtgata ctaactacaa tggaaagttc aagggtaaag ccactctgac tgcagacgaa      600
tcctccagca cagcctacat gcaactcagc agcctagcat ctgaggactc tgcggtctat      660
ttctgtgcaa gacgggagac tacgacggta ggccgttatt actatgctat ggactactgg      720
ggccaaggga ccacggtcac cgtctcctcc                                       750

<210> SEQ ID NO 49
<211> LENGTH: 250
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240
```

```
Gly Gln Gly Thr Thr Val Thr Val Ser Ser
                245                 250
```

<210> SEQ ID NO 50
<211> LENGTH: 720
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 50

```
gacattcagc tgacccagtc tccagcaatc atgtctgcat ctccagggga gaaggtcacc      60
atgacctgca gagccagttc aagtgtaagt tacatgaact ggtaccagca gaagtcaggc     120
acctccccca aaagatggat ttatgacaca tccaaagtgg cttctggagt cccttatcgc     180
ttcagtggca gtgggtctgg gacctcatac tctctcacaa tcagcagcat ggaggctgaa     240
gatgctgcca cttattactg ccaacagtgg agtagtaacc cgctcacgtt cggtgctggg     300
accaagctgg agctgaaagg tggtggtggt tctggcggcg gcggctccgg tggtggtggt     360
tctgatatca aactgcagca gtcaggggct gaactggcaa gacctggggc tcagtgaag     420
atgtcctgca gacttctgg ctacacctttt actaggtaca cgatgcactg gtaaaacag     480
aggcctggac agggtctgga atggattgga tacattaatc ctagccgtgg ttatactaat     540
tacaatcaga gttcaagga caaggccaca ttgactacag acaaatcctc cagcacagcc     600
tacatgcaac tgagcagcct gacatctgag gactctgcag tctattactg tgcaagatat     660
tatgatgatc attactgcct tgactactgg ggccaaggca ccactctcac agtctcctca     720
```

<210> SEQ ID NO 51
<211> LENGTH: 240
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 51

```
Asp Ile Gln Leu Thr Gln Ser Pro Ala Ile Met Ser Ala Ser Pro Gly
1               5                   10                  15
Glu Lys Val Thr Met Thr Cys Arg Ala Ser Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Thr Ser Lys Val Ala Ser Gly Val Pro Tyr Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Ser Asn Pro Leu Thr
                85                  90                  95
Phe Gly Ala Gly Thr Lys Leu Glu Leu Lys Gly Gly Gly Gly Ser Gly
            100                 105                 110
Gly Gly Gly Ser Gly Gly Gly Gly Ser Asp Ile Lys Leu Gln Gln Ser
        115                 120                 125
Gly Ala Glu Leu Ala Arg Pro Gly Ala Ser Val Lys Met Ser Cys Lys
    130                 135                 140
Thr Ser Gly Tyr Thr Phe Thr Arg Tyr Thr Met His Trp Val Lys Gln
145                 150                 155                 160
```

-continued

```
Arg Pro Gly Gln Gly Leu Glu Trp Ile Gly Tyr Ile Asn Pro Ser Arg
            165                 170                 175

Gly Tyr Thr Asn Tyr Asn Gln Lys Phe Lys Asp Lys Ala Thr Leu Thr
        180                 185                 190

Thr Asp Lys Ser Ser Thr Ala Tyr Met Gln Leu Ser Ser Leu Thr
    195                 200                 205

Ser Glu Asp Ser Ala Val Tyr Tyr Cys Ala Arg Tyr Tyr Asp His
    210                 215                 220

Tyr Cys Leu Asp Tyr Trp Gly Gln Gly Thr Thr Leu Thr Val Ser Ser
225                 230                 235                 240

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Tyr Thr Phe Thr Arg Tyr Thr Met His
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Ile Asn Pro Ser Arg Gly Tyr Thr Asn Tyr Asn Gln Lys Val Lys
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Tyr Asp Asp His Tyr Cys Leu Asp Tyr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ala Ser Ser Ser Val Ser Tyr Met Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 56

Asp Thr Ser Lys Val Ala Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Trp Ser Ser Asn Pro Leu Thr
1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Tyr Ala Phe Ser Ser Tyr Trp Met Asn
1               5                   10

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ile Trp Pro Gly Asp Gly Asp Thr Asn Tyr Asn Gly Lys Phe Lys
1               5                   10                  15
        Gly

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Glu Thr Thr Thr Val Gly Arg Tyr Tyr Tyr Ala Met Asp Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Ala Ser Gln Ser Val Asp Tyr Asp Gly Asp Ser Tyr Leu Asn
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Asp Ala Ser Asn Leu Val Ser
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Gln Gln Ser Thr Glu Asp Pro Trp Thr
1               5

<210> SEQ ID NO 64
<211> LENGTH: 372
<212> TYPE: DNA
<213> ORGANISM: Artificial Sequence
<220> FEATURE:
<223> OTHER INFORMATION: Description of Artificial Sequence: Synthetic construct

<400> SEQUENCE: 64
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg agatggtgaa tactaactac     180
aatggaaagt tcaagggtaa agccactctg actgcagacg aatcctccag cacagcctac     240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                         372

<210> SEQ ID NO 65
<211> LENGTH: 124
<212> TYPE: PRT
<213> ORGANISM: Artificial Sequence
<220> FEATURE:
<223> OTHER INFORMATION: Description of Artificial Sequence: Synthetic construct

<400> SEQUENCE: 65

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys

```
                    85                  90                  95
Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 66
<211> LENGTH: 333
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 66

```
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaa                                   333
```

<210> SEQ ID NO 67
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 67

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110
```

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

```
ggtggtggtg gttctggcgg cggcggctcc ggtggtggtg gttct                      45
```

<210> SEQ ID NO 69
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Gly Ser Gly Gly Gly Gly Ser Gly Gly Gly Gly Ser
      1               5                   10                  15

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggaggtggtg gatcc                                                       15

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Gly Gly Ser
      1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ala Ser Ser Ser Val Ser Tyr Met Asn
      1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Thr Ser Lys Leu Ala Ser
      1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Trp Ser Ser Asn Pro Phe Thr
      1               5
```

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Gly Tyr Lys Phe Ser Ser Ser Val Met His
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Tyr Ile Asn Pro Tyr Asn Asp Val Thr Lys Tyr Thr Glu Lys Phe Lys
1               5                   10                  15
Gly

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Ser Pro Tyr Tyr Asp Tyr Asp Gly Phe Ala Tyr
1               5                   10

<210> SEQ ID NO 78
<211> LENGTH: 393
<212> TYPE: DNA
<213> ORGANISM: Artificial Sequence
<220> FEATURE:
<223> OTHER INFORMATION: Description of Artificial Sequence: Synthetic construct

<400> SEQUENCE: 78
atgggatgga gctgtatcat cctcttcttg gtagcaacag ctacaggtgt acactccgat      60
ggtaatgaag aaatgggtgg tattacacag acaccatata agtctccat ctctggaacc     120 acagtaatat tgacatgccc tcagtatcct ggatctgaaa tactatggca acacaatgat    180
aaaaacatag gcggtgatga ggatgataaa aacataggca gtgatgagga tcacctgtca    240
ctgaaggaat tttcagaatt ggagcaaagt ggttattatg tctgctaccc cagaggaagc    300
aaaccagaag atgcgaactt ttatctctac ctgagggcaa gagtgtgtga gaactgcatg    360
gagatggatt ccgggcatca tcaccatcat cat                                 393

<210> SEQ ID NO 79
<211> LENGTH: 131
<212> TYPE: PRT
<213> ORGANISM: Artificial Sequence
<220> FEATURE:
<223> OTHER INFORMATION: Description of Artificial Sequence: Synthetic construct

<400> SEQUENCE: 79

```
Met Gly Trp Ser Cys Ile Ile Leu Phe Leu Val Ala Thr Ala Thr Gly
1               5                   10                  15
Val His Ser Asp Gly Asn Glu Glu Met Gly Gly Ile Thr Gln Thr Pro
            20                  25                  30
Tyr Lys Val Ser Ile Ser Gly Thr Thr Val Ile Leu Thr Cys Pro Gln
        35                  40                  45
Tyr Pro Gly Ser Glu Ile Leu Trp Gln His Asn Asp Lys Asn Ile Gly
    50                  55                  60
Gly Asp Glu Asp Asp Lys Asn Ile Gly Ser Asp Glu Asp His Leu Ser
65                  70                  75                  80
Leu Lys Glu Phe Ser Glu Leu Glu Gln Ser Gly Tyr Tyr Val Cys Tyr
                85                  90                  95
Pro Arg Gly Ser Lys Pro Glu Asp Ala Asn Phe Tyr Leu Tyr Leu Arg
            100                 105                 110
Ala Arg Val Cys Glu Asn Cys Met Glu Met Asp Ser Gly His His His
            115                 120                 125
His His His
        130
```

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
aggtgtacac tccgatggta atgaagaaat gggtgg                                36

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
cgatccggaa tccatctcca tgcagttctc acacactctt gc                        42

<210> SEQ ID NO 82
<211> LENGTH: 146
<212> TYPE: DNA
<213> ORGANISM: Artificial Sequence
<220> FEATURE:
<223> OTHER INFORMATION: Description of Artificial Sequence: Synthetic construct

<400> SEQUENCE: 82
gaattcacca tgggatggag ctgtatcatc ctcttcttgg tagcaacagc tacaggtgta     60
cactccgata tcaagcttcc ggacgctccc gactcaagcg cccgtgccac acagccgcaa    120
gatctggcgc cgtgtggtca gtcgac                                         146

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

```
Gly Gly Gly Gly Ser Gly Gly Gly Gly Ser
1               5                   10
```

PHARMACEUTICAL COMPOSITIONS COMPRISING BISPECIFIC ANTI-CD3, ANTI-CD19 ANTIBODY CONSTRUCTS FOR THE TREATMENT OF B-CELL RELATED DISORDERS

This application is a National Stage application of PCT/EP2004/005685 filed May 26, 2004, which claims priority from European patent application EP 03012136.2, filed May 31, 2003. The entire contents of each of the aforementioned applications are incorporated herein by reference.

The present invention relates to a pharmaceutical composition comprising a bispecific single chain antibody construct, said bispecific single chain antibody construct comprising binding domains specific for human CD3 and human CD19, wherein the corresponding variable heavy chain regions ($V_H$) and the corresponding variable light chain regions ($V_L$) are arranged, from N-terminus to C-terminus, in the order, $V_H(CD19)$-$V_L(CD19)$-$V_H(CD3)$-$V_L(CD3)$, $V_H(CD3)$-$V_L(CD3)$-$V_H(CD19)$-$V_L(CD19)$ or $V_H(CD3)$-$V_L(CD3)$-$V_L(CD19)$-$V_H(CD19)$. Furthermore, processes for the production of said pharmaceutical compositions as well as medical/pharmaceutical uses for the specific bispecific single chain antibody molecules bearing specificities for the human CD3 antigen and the human CD19 antigen are disclosed.

Despite the medical importance, research in B-cell mediated diseases such as non-Hodgkin lymphoma has produced only a small number of clinically usable data and conventional approaches to cure such diseases remain tedious and unpleasant and/or have a high risk of relapse. For example, although high dose chemotherapy as a primary treatment for high grade non-Hodgkin lymphoma may improve overall survival, about 50% of the patients still die of this disease (Gianni, N Engl. J. Med. 336 (1997), 1290-7; Urba, J. Natl. Cancer Inst. Monogr. (1990), 29-37; Fisher, Cancer (1994)). Moreover, low-grade non-Hodgkin lymphoma-like chronic lymphatic leukemia and mantle cell lymphoma are still incurable. This has stimulated the search for alternative strategies such as immunotherapy. Antibodies directed against cell surface molecules defined by CD antigens represent a unique opportunity for the development of therapeutic reagents. The expression of certain CD antigens is highly restricted to specific lineage lymphohematopoietic cells and over the past several years, antibodies directed against lymphoid-specific antigens have been used to develop treatments that were effective either in vitro or in vivo animal models (Bohlen, Blood 82 (1993), 1803-121; Bohlen, Cancer Res 53 (1993), 18: 4310-4; Bohlen, Cancer Res 57 (1997), 1704-9; Haagen, Clin Exp Immunol 90 (1992), 368-75; Haagen, Cancer Immunol Immunother. 39 (1994), 391-6; Haagen, Blood 84 (1994), 556-63; Haagen, Blood 85 (1995), 3208-12; Weiner, Leuk Lymphoma 16 (1995), 199-207; Csoka, Leukemia 10 (1996), 1765-72.). In this respect CD19 has proved to be a very useful target. CD19 is expressed in the whole B lineage from the pro B cell to the mature B cell, it is not shed, is uniformly expressed on all lymphoma cells, and is absent from stem cells (Haagen, Clin Exp Immunol 90 (1992), 368-75; Uckun, Proc. Natl. Acad. Sci. USA 85 (1988), 8603-7). An interesting modality is the application of a bispecific antibody with one specificity for CD19 and the other for the CD3 antigen on T cells. However, bispecific antibodies thus far available suffer from low T-cell cytotoxicity and the need of costimulatory agents in order to display satisfactory biological activity. The CD3 complex denotes an antigen that is expressed on T-cells as part of the multimolecular T-cell receptor complex. It consists of several different chains for instance γ, δ, ε, ζ or/and η chains. Clustering of CD3 on T cells, e.g., by immobilized anti-CD3-antibodies, leads to T cell activation similar to the engagement of the T cell receptor but independent from its clone typical specificity. Actually, most anti-CD3-antibodies recognize the CD3ε-chain.

Prior art has exemplified T cell activation events employing antibody molecules. For example, U.S. Pat. No. 4,361,549 proposes a hybrid cell line for the production of monoclonal antibody to an antigen found on normal human T cells and cutaneous T lymphoma cells and defines the antibody produced as "OKT3". In U.S. Pat. No. 5,885,573 the murine OKT3 (described in U.S. Pat. No. 4,361,549) has been transferred into a human antibody framework in order to reduce its immunogenicity. Furthermore, U.S. Pat. No. 5,885,573 discloses specific mutations in the Fc receptor ("FcR")-binding segment of OKT-3 which leads to a Glu at position 235, a Phe at position 234 or a Leu at position 234, i.e. to specific mutations in the CH2 region which are supposed to result in modified binding affinities for human FcR. In proliferation assays or in assays relating to the release of cytokines, the mutated OKT-3 antibodies disclosed in U.S. Pat. No. 5,885,573 appear to result in comparable cell proliferations to that observed with PBMC stimulated with the original murine OKT3 and to similar amounts of cytokines produced. Merely the mutated Glu-235 mAb induced smaller quantities of TNF-α and GM-CSF and no IFN-γ. No T cell proliferation was induced by Glu-235 monoclonal antibody ("mab") using PBMC from three different donors at mab concentrations up to 10 μg/ml, suggesting that the alteration of the FcR binding region of this mab had impaired its mitogenic properties. T cell activation by Glu-235 mab also resulted in lower levels of expression of surface markers Leu23 and IL-2 receptor. U.S. Pat. No. 5,929,212 discloses a recombinant antibody molecule in which the binding regions have been derived from the heavy and/or light chain variable regions of a murine anti-CD3 antibody, e.g. OKT3, and have been grafted into a human framework. WO 98/52975 discloses a mutated variant of the murine anti-CD3 antibody OKT3. The mutated OKT3 antibody is produced using a recombinant expression system and WO 98/52975 proposes that the mutated anti-CD3 antibody is more stable than the parental OKT3 protein during extended storage periods. U.S. Pat. No. 5,955,358 discloses a method of shuffling, at the DNA level, multiple complementarity determining ("CDR") domains, either from the same or different antibodies, meaning that their order within antibody variable domains is altered to yield new combinations of binding regions.

OKT3 has been used as potent immunosuppressive agent in clinical transplantation to treat allograft rejection (Thistlethwaite 1984, Transplantation 38, 695-701; Woodle 1991, Transplantation 51, 1207-1212; Choi 2001, Eur. J. Immunol. 31(1), 94-106). Major drawbacks of this therapy are T cell activation manifested in cytokine release due to cross-linking between T cells and FcγR-bearing cells and the human anti-mouse antibody (HAMA) response. Several publications have described alterations such as humanization of OKT3 to reduce these side effects: U.S. Pat. No. 5,929,212; U.S. Pat. No. 5,885,573 and others. On the other hand, OKT3 or other anti-CD3-antibodies can be used as immunopotentiating agents to stimulate T cell activation and proliferation (U.S. Pat. No. 6,406,696 Bluestone; U.S. Pat. No. 6,143,297 Bluestone; U.S. Pat. No. 6,113,901 Bluestone; Yannelly 1990, J. Immunol. Meth. 1, 91-100). Anti-CD3-antibodies have also been described as agents used in combination with anti-CD28-antibodies to induce T cell proliferation (U.S. Pat. No. 6,352,694). OKT3 has further been used by itself or as a component of a bispecific antibody to target cytotoxic T cells to tumor cells or virus infected cells (Nitta 1990, Lancet 335, 368-376; Sanna 1995, Bio/Technology 13, 1221-1224; WO 99/54440).

Approaches up to now using antibodies as agents for recruiting T-cells have been hampered by several findings. First, natural or engineered antibodies having a high binding affinity to T-cells often do not activate the T-cells to which they are bound. Second, natural or engineered antibodies having a low binding affinity to T-cells are also often ineffective with respect to their ability to trigger T-cell mediated cell lysis.

Bispecific antibodies comprising specificities for human CD19 and human CD3 which are not of the single-chain format and which retarget T-cell cytotoxicity to lymphoma cells in an MHC-independent manner have already been shown to be effective in vivo in animal models (Bohlen, Cancer Res 57 (1997), 1704-9; Demanet, Int J Cancer Suppl 7 (1992), 67-8) as well as in some pilot clinical trials. So far these antibodies were constructed by hybrid-hybridoma techniques, by covalently linking the monoclonal antibodies (Anderson, Blood 80 (1992), 2826-34) or by a diabody approach (Kipriyanov, Int. J. Cancer 77 (1998), 763-772). More extensive clinical studies have been hampered by the fact that these antibodies have low biological activity such that high dosages have to be administered and that application of the antibodies alone did not provide for a beneficial therapeutic effect. Furthermore, the availability of clinical grade material was limited. The prior art has exemplified bispecific single chain antibodies comprising specificities for both human CD3 and human CD19 antigens (Loffler, Blood 95 (2000), 2098-103; WO 99/54440; Dreier, Int. J. Cancer. 100 (2002), 690-7). WO 99/54440 documents the successful clinical use of a construct in the format $V_L$(CD19)-$V_H$(CD19)-$V_H$(CD3)-$V_L$(CD3) and stresses that the order of variable domains within the construct is not decisive.

Yet, in particular for distinct clinical and pharmaceutical uses, constructs have to be provided which can be produced in large amounts by reasonably high levels of expression of the recombinant constructs and by adequate purification methods after expression. In the event that extremely low amounts of pure protein are obtained, it becomes prohibitively cumbersome and/or costly to generate therapeutically relevant amounts of such constructs. In the special case of proteinaceous medicaments intended for parental administration, these medicaments should be highly active and potent, even in low concentrations, in order to avoid adverse side-effects due to excessive protein concentrations or voluminous infusion/injection solutions. Disadvantages of highly-dosed proteinaceous medicaments or highly-dosed medicaments based on nucleic acids comprise, inter alia, the promotion of hypersensitivities and inflammatory events, in particular at the site of administration. Thus, the technical problem of the present invention is the provision of means and methods for the generation of well tolerated and convenient medicaments for the treatment and or amelioration of B-cell related or B-cell mediated disorders.

Accordingly, the present invention relates to a pharmaceutical composition comprising a bispecific single chain antibody construct, said bispecific single chain antibody construct comprising binding domains specific for human CD3 and human CD19, wherein the corresponding variable heavy chain regions ($V_H$) and the corresponding variable light chain regions ($V_L$) are arranged, from N-terminus to C-terminus, in the order, $V_H$(CD19)-$V_L$(CD19)-$V_H$(CD3)-$V_L$(CD3),
$V_H$(CD3)-$V_L$(CD3)-$V_H$(CD19)-$V_L$(CD19) or
$V_H$(CD3)-$V_L$(CD3)-$V_L$(CD19)-$V_H$(CD 19).

Accordingly, "$V_L$" and "$V_H$" means the variable domain of the light and heavy chain of specific anti-CD19 (CD19) and anti-CD3 (CD3) antibodies.

In accordance with this invention, the term "pharmaceutical composition" relates to a composition for administration to a patient, preferably a human patient. In a preferred embodiment, the pharmaceutical composition comprises a composition for parenteral, transdermal, intraluminal, intraarterial, intrathecal administration or by direct injection into tissue. It is in particular envisaged that said pharmaceutical composition is administered to a patient via infusion or injection. Administration of the suitable compositions may be effected by different ways, e.g., by intravenous, intraperitoneal, subcutaneous, intramuscular, topical or intradermal administration. The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regiment will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. A preferred dosage for administration might be in the range of 0.24 µg to 48 mg, preferably 0.24 µg to 24 mg, more preferably 0.24 µg to 2.4 mg, even more preferably 0.24 µg to 1.2 mg and most preferably 0.24 µg to 240 µg units per kilogram of body weight per day. Particularly preferred dosages are recited herein below. Progress can be monitored by periodic assessment. Dosages will vary but a preferred dosage for intravenous administration of DNA is from approximately $10^6$ to $10^{12}$ copies of the nucleic acid molecule, preferably a DNA molecule. The pharmaceutical compositions of the invention comprising proteinaceous or nucleic acid compounds described herein may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the pharmaceutical composition of the present invention might comprise proteinaceous carriers, like, e.g., serum albumin or immunoglobulin, preferably of human origin. It is envisaged that the pharmaceutical composition of the invention might comprise, in addition to the proteinaceous bispecific single chain antibody constructs or nucleic acid molecules or vectors encoding the same (as described in this invention), further biologically active agents, depending on the intended use of the pharmaceutical composition. Such agents might be drugs acting on the gastrointestinal system, drugs acting as cytostatica, drugs preventing hyperurikemia, drugs inhibiting immunoreactions (e.g. corticosteroids), drugs acting on the circulatory system and/or agents such as T-cell co-stimulatory molecules or cytokines known in the art.

The term "bispecific single chain antibody construct" relates to a construct comprising one domain consisting of variable regions (or parts thereof) as defined above, capable of specifically interacting with/binding to human CD3 and comprising a second domain consisting of variable regions (or parts thereof as defined above, capable of specifically interacting with/binding to human CD19.

Said binding/interaction is also understood to define a "specific recognition". The term "specifically recognizing" means in accordance with this invention that the antibody molecule is capable of specifically interacting with and/or binding to at least two amino acids of each of the human target molecule as defined herein. Said term relates to the specificity of the antibody molecule, i.e. to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Further, said binding may be exemplified by the specificity of a "key-lock-principle". Thus, specific motifs in the amino acid sequence of the antigen-interaction-site and the antigen bind to each other as a result of their primary, secondary or tertiary structure as well as the result of secondary modifications of said structure. The specific interaction of the antigen-interaction-site with its specific antigen may result as well in a simple binding of said site to the antigen.

The term "specific interaction" as used in accordance with the present invention means that the bispecific single chain construct does not or essentially does not cross-react with (poly)peptides of similar structures. Cross-reactivity of a panel of bispecific single chain construct under investigation may be tested, for example, by assessing binding of said panel of bispecific single chain construct under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999) to the (poly)peptide of interest as well as to a number of more or less (structurally and/or functionally) closely related (poly)peptides. Only those antibodies that bind to the (poly)peptide/protein of interest but do not or do not essentially bind to any of the other (poly)peptides are considered specific for the (poly)peptide/protein of interest.

Examples for the specific interaction of an antigen-interaction-site with a specific antigen comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens like antigens of the selectin family, integrins and of the family of growth factors like EGF. An other example for said interaction, which is also particularly comprised by said definition, is the interaction of an antigenic determinant (epitope) with the antigenic binding site of an antibody.

The term "binding to/interacting with" may also relate to a conformational epitope, a structural epitope or a discontinuous epitope consisting of two regions of the human target molecules or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Laver, (1990) Cell 61, 553-6).

The term "discontinuous epitope" means in context of the invention non-linear epitopes that are assembled from residues from distant portions of the polypeptide chain. These residues come together on the surface of the molecule when the polypeptide chain folds into a three-dimensional structure to constitute a conformational/structural epitope.

According to the present invention the term "variable region" used in the context with Ig-derived antigen-interaction comprises fragments and derivatives of (poly)peptides which at least comprise one CDR derived from an antibody, antibody fragment or derivative thereof. It is envisaged by the invention, that said at least one CDR is preferably a CDR3, more preferably the CDR3 of the heavy chain of an antibody (CDR-H3). However, other antibody derived CDRs are also particularly comprised by the term "variable region"

The "specific binding" of an antibody is characterized primarily by two parameters: a qualitative parameter (the binding epitope, or where the antibody binds) and a quantitative parameter (the binding affinity, or how strongly it binds where it does). Which epitope is bound by an antibody can advantageously be determined by e.g. known FACS methodology, peptide-spot epitope mapping, mass spectroscopy. The strength of antibody binding to a particular epitope may be advantageously be determined by e.g. known BIAcore and/or ELISA methodologies. A combination of such techniques allows the calculation of a signal:noise ratio as a representative measure of binding specificity. In such a signal:noise ratio, the signal represents the strength of antibody binding to the epitope of interest, whereas the noise represents the strength of antibody binding to other, non-related epitopes differing from the epitope of interest. In general, any time an antibody binds more frequently and/or strongly to one epitope than another epitope, such antibody may be said to bind the former epitope specifically. Preferably, a signal: noise ratio for an epitope of interest which is about 50-fold higher than for other epitopes different from the epitope of interest may be taken as an indication that the antibody evaluated binds the epitope of interest in a specific manner, i.e. is a "specific binder".

As will be detailed below, a part of a variable region may be at least one CDR ("Complementary determining region"), most preferably at least the CDR3 region. Said two domains/regions in the single chain antibody construct are preferably covalently connected to one another as a single chain. This connection can be effected either directly (domain1 directed against CD3—domain2 directed against CD 19 or domain1 directed against CD19—domain2 directed against CD3) or through an additional polypeptide linker sequence (domain1—linker sequence—domain2). In the event that a linker is used, this linker is preferably of a length and sequence sufficient to ensure that each of the first and second domains can, independently from one another, retain their differential binding specificities. Most preferably and as documented in the appended examples, the "bispecific single chain antibody construct" to be employed in the pharmaceutical composition of the invention is a bispecific single chain Fv (scFv). Bispecific single chain molecules are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-

197, Löffler, Blood, (2000), 95, 6, 2098-2103, Brühl, Immunol., (2001), 166, 2420-2426, Kipriyanov, J. Mol. Biol., (1999), 293, 41-56.

The term "single-chain" as used in accordance with the present invention means that said first and second domain of the bispecific single chain construct are covalently linked, preferably in the form of a co-linear amino acid sequence encodable by a single nucleic acid molecule.

As pointed out above, CD19 denotes an antigen that is expressed in the B lineage such as in the pro B cell and the mature B cell, it is not shed, is uniformly expressed on all lymphoma cells, and is absent from stem cells (Haagen (1992) loc.cit; Uckun (1988) PNAS 85, 8603-8607). CD3 denotes an antigen that is expressed on T-cells as part of the multimolecular T-cell receptor complex and that consists of at least three different chains CD3ε, CD3δ and CD3γ. Clustering of CD3 on T-cells, e.g., by immobilized anti-CD3-antibodies, leads to T-cell activation similar to the engagement of the T-cell receptor but independent from its clone typical specificity. Actually, most anti-CD3-antibodies recognize the CD3ε-chain.

Antibodies that specifically recognize CD19 or CD3 antigen are described in the prior art, e.g., in Dubel (1994), J. Immunol. Methods 175, 89-95; Traunecker (1991) EMBO J. 10, 3655-3699 or Kipriyanov, (1998), loc.cit. Further illustrative examples are listed below. Furthermore, antibodies directed against human CD3 and/or human CD19 can be generated by conventional methods known in the art.

Here it was surprisingly found that bispecific single chain constructs directed against human CD3 and human CD19 and comprising variable regions ($V_H$ (corresponds to $V_H$), $V_L$ (corresponds to $V_L$)) or parts thereof (e.g. CDRs) in the format $V_H$(CD19)-$V_L$(CD19)-$V_H$(CD3)-$V_L$(CD3), $V_H$(CD3)-$V_L$(CD3)-$V_H$(CD19)-$V_L$(CD19) or $V_H$(CD3)-$V_L$(CD3)-$V_L$(CD19)-$V_H$(CD19) are particularly useful as pharmaceutical compositions since these constructs are advantageous over constructs of similar formats, like $V_L$(CD3)-$V_H$(CD3)-$V_L$(CD19)-$V_H$(CD19), $V_L$(CD3)-$V_H$(CD3)-$V_H$(CD19)-$V_L$(CD19), $V_L$(CD19)-$V_H$(CD19)-$V_L$(CD3)-$V_H$(CD3) or $V_H$(CD19)-$V_L$(CD19)-$V_L$(CD3)-$V_H$(CD3). The latter four constructs/construct formats are characterized by less advantageous cytotoxic activity as reflected by $EC_{50}$ values and/or less efficient or complete purifications as shown in the appended examples. It was in particular surprising that the anti-CD3 part of the single chain constructs to be employed in accordance with the invention are highly bioactive in N- as well as C-terminal position, whereas arrangements in $V_H$(CD3)-$V_L$(CD3) are particularly preferred. The constructs to be employed in the pharmaceutical composition of the invention are characterized by advantageous production and purification properties as well as by their high bioactivity, i.e. their desired cytotoxic activity. The corresponding high bioactivity is reflected by low to very low $EC_{50}$ values as determined in cytotoxicity tests. The term "$EC_{50}$" corresponds, in context of this invention, to $EC_{50}$ values as determined according to the methods known in the art and as illustrated in the appended examples: a standard dose-response curve is defined by four parameters: the baseline response (Bottom), the maximum response (Top), the slope of dose-response increase, and the drug concentration that elicits a response halfway between baseline and maximum ($EC_{50}$). $EC_{50}$ is defined as the concentration of a drug or molecule that elicits a response halfway between the baseline (Bottom) and maximum response (Top). The percentage of cell lysis (i.e. cytotoxic activity) may be determined by, inter alia, release assays disclosed herein above, for example, $^{51}Cr$ release assays, LDH-release assays, calcein release assays and the like. Most preferably, in the context of this invention fluorochrome release assays are employed as illustrated in the appended examples. Here, strong cytotoxic activity against CD19-positive cells (experimentally for example NALM6 cells) of the bispecific single chain constructs described herein relates to a molecule comprising $EC_{50}$ values </- (less or equal to) 500 pg/ml, more preferably </-400 pg/ml, even more preferably </-300 pg/ml, even more preferably </-250 pg/ml, most preferably </-200 pg/ml. Here, it was surprisingly found that certain constructs having the formats $V_H$(CD19)-$V_L$(CD19)-$V_H$(CD3)-$V_L$(CD3) and $V_H$(CD3)-$V_L$(CD3)-$V_H$(CD19)-$V_L$(CD19) demonstrate advantageous properties in addition to high cytotoxic activity which make these constructs well-suited to inclusion in pharmaceutical compositions. In contrast, other constructs such as $V_H$(CD19)-$V_L$(CD19)-$V_L$(CD3)-$V_H$(CD3) are only very poorly producible/isolatable making, for example the latter construct very poorly suited to inclusion in pharmaceutical compositions.

In a preferred embodiment of the pharmaceutical composition of this invention, the VH and VL regions of said CD3 specific domain are derived from a CD3 specific antibody selected from the group consisting of X35-3, VIT3, BMA030 (BW264/56), CLB-T3/3, CRIS7, YTH12.5, F111-409, CLB-T3.4.2, WT31, WT32, SPv-T3b, 11D8, XIII-141, XIII-46, XIII-87, 12F6, T3/RW2-8C8, T3/RW2-4B6, OKT3D, M-T301, SMC2 and F101.01. These CD3-specific antibodies are well known in the art and, inter alia, described in Tunnacliffe (1989), Int. Immunol. 1, 546-550. In a more preferred embodiment, said VH and VL regions of said CD3 specific domain are derived from OKT-3 (as defined and described above) or TR-66. Even more preferred (and as illustrated in the appended examples) said VH and VL regions are or are derived from an antibody/antibody derivative specifically directed against CD3 described by Traunecker (1991), EMBO J. 10, 3655-3659. In accordance with this invention, said VH and VL regions are derived from antibodies/antibody derivatives and the like which are capable of specifically recognizing human CD3 epsilon in the context of other TCR subunits, e.g. in mouse T cells transgenic for human CD3 epsilon. These transgenic mouse cells express human CD3 epsilon in a native or near native conformation. Accordingly, the VH and VL regions derived from a CD3-epsilon-specific antibody are most preferred in accordance with this invention and said (parental) antibodies should be capable of specifically binding epitopes reflecting the native or near native structure or a conformational epitope of human CD3 presented in context of the TCR complex. Such antibodies have been classified by Tunnacliffe (1989) as "group II" antibodies. Further classifications in Tunnacliffe (1989) comprise the definition of "group I" and "group III" antibodies directed against CD3. "Group I" antibodies, like UCHT1, recognize CD3 epsilon both expressed as recombinant protein as well as part of the TCR on the cell surface. Therefore, "group I" antibodies are highly specific for CD3 epsilon. In contrast, the herein preferred "group II" antibodies recognize CD3 epsilon only in the native TCR complex in association with other TCR subunits. Without being bound by theory, it is speculated in context of this invention that in "group II" antibodies, the TCR context is required for recognition of CD3 epsilon. CD3 gamma and/or delta, being associated with epsilon, are also involved in binding of "group II" antibodies. All three subunits express immuno-tyrosine activation motifs (ITAMs) which can be tyrosine phosphorylated by protein tyrosine kinases. For this reason "group II" antibodies induce T cell signaling via CD3 epsilon, gamma and delta, leading to a stronger signal compared to "group I" antibodies selectively inducing T cell signaling via CD3 epsilon. Yet, since for therapeutic applications induction of a strong T cell signaling is desired, the VH (CD3)/VL (CD3)-regions (or parts thereof) to be employed in the bispecific single chain constructs comprised in the inventive pharmaceutical composition, are preferably derived from antibodies directed against human CD3 and classified as "group II" by Tunnacliffe (1989), loc.cit.

Antibodies/antibody molecules/antibody derivatives directed against human CD19 which provide for variable regions ($V_H$ and $V_L$) to be employed in the bispecific single chain construct(s) comprised in the inventive pharmaceutical composition are also well known in the art and illustrated in the appended examples. Preferred antibodies directed to human CD19 are: 4G7 (Meecker (1984) Hybridoma 3, 305-20); B4 (Freedman (1987) Blood 70, 418-27; B43 (Bejcek (1995) Cancer Res. 55, 2346-51); BU12 (Flavell (1995) Br. J. Cancer 72, 1373-9); CLB-CD19 (De Rie (1989) Cell. Immunol. 118, 368-81); Leu-12 (MacKenzie (1987), J. Immunol. 139, 24-8); SJ25-C1 (GenTrak, Plymouth Meeting, Pa.)

In a most preferred embodiment of the invention said $V_H$(CD19) and $V_L$(CD19) regions (or parts, like CDRs, thereof) are derived from the antibody provided by the HD37 hybridoma (Pezzutto (1997), J. Immunol. 138, 2793-9).

As is well known, Fv, the minimum antibody fragment which contains a complete antigen recognition and binding site, consists of a dimer of one heavy and one light chain variable domain (VH and VL) in non-covalent association. In this configuration corresponding to the one found in native antibodies, the three CDRs of each variable domain interact to define an antigen binding site on the surface of the VH-VL dimer. Collectively, the six CDRs confer antigen binding specificity to the antibody. Frameworks (FRs) flanking the CDRs have a tertiary structure which is essentially conserved in native immunoglobulins of species as diverse as human and mouse. These FRs serve to hold the CDRs in their appropriate orientation. The constant domains are not required for binding function, but may aid in stabilizing VH-VL interaction.

It is also envisaged in context of the present invention that the bispecific antibody constructs provided in the pharmaceutical composition of the invention are further modified. In particular, it is envisaged that the bispecific single chain antibody construct in the format $V_H$(CD19)-$V_L$(CD19)-$V_H$(CD3)-$V_L$(CD3), $V_H$(CD3)-$V_L$(CD3)-$V_H$(CD19)-$V_L$(CD19) or $V_H$(CD3)-$V_L$(CD3)-$V_L$(CD19)-$V_H$(CD19) as defined herein are deimmunized. Most preferably, at least the CD3-binding portion is deimmunized. Deimmunization entails carrying out substitutions of amino acids within potential T cell epitopes.

It is envisaged and preferred that the pharmaceutical composition of the invention, comprises a bispecific single chain antibody construct in the format $V_H$(CD19)-$V_L$(CD19)-$V_H$(CD3)-$V_L$(CD3), $V_H$(CD3)-$V_L$(CD3)-$V_H$(CD19)-$V_L$(CD19) or $V_H$(CD3)-$V_L$(CD3)-$V_L$(CD19)-$V_H$(CD19) as defined above, wherein said $V_H$ region comprises at least one CDR3 region (CDR-H3 or CDR-3 of $V_H$) comprising the amino acid sequence: SEQ ID NO. 54 or 77.

The term "CDR-region" as used herein denotes the "complementary determining region" of an antibody molecule. Accordingly, the term "CDR-3 region", synonymous with the term "CDR3 region", relates to the "complementary determining region 3" of an antibody molecule/antibody construct. The same applies, mutatis mutandis, for corresponding CDR-2 and CDR-1 regions. It is envisaged and preferred that the bispecific single chain construct comprised in the pharmaceutical composition of the present invention does not only comprise CDR-3 regions, but also comprises CDR-1 or CDR-2 region(s) of variable regions/variable domains (VH/VL) of antibodies/antibody molecules directed against human CD3 and human CD19. Most preferably, the said molecule comprises at least one CDR-3 region of a VH and at least one CDR-3 region of an VL-domain of an antibody directed against CD3 as well as at least one CDR-3 region of an VH and at least one CDR-3 region of a VL-domain of an antibody directed against CD19. Most preferably, the bispecific single chain construct of the inventive pharmaceutical composition comprises in addition at least one further CDR-1 region and/or at least one further CDR-2 region in the VH and VL domains defined herein. Accordingly, the bispecific single chain construct defined herein may comprise CDR-1, CDR-2, CDR-3 region of VL as well as CDR-1, CDR-2, CDR-3 region of VH of an antibody/antibody molecule directed against human CD3, preferably human CD3 epsilon, and comprises, in addition, CDR-1, CDR-2, CDR-3 region of VL as well as CDR-1, CDR-2, CDR-3 region of VH of an antibody/antibody molecule directed against human CD19.

Preferably, said VH (CD3) region comprises at least one CDR2 region comprising the amino acid sequence: SEQ ID NO. 53 or 76. It is also envisaged that said VH (CD3) region comprises at least one CDR1 region comprising the amino acid sequence: SEQ ID NO. 52 or 75.

The VL (CD3) region comprises, preferably, at least one CDR3 region comprising the amino acid sequence: SEQ ID NO. 57 or 74. The VL (CD3) may comprise at least one CDR2 region comprising the amino acid sequence: SEQ ID NO. 56 or 73. The VL (CD3) may also comprise at least one CDR1 region comprising the amino acid sequence: SEQ ID NO. 55 or 72.

As mentioned herein above, the constructs comprised in the inventive pharmaceutical composition comprise at least one CDR-3 of a VH-region of an antibody directed against human CD3, at least one CDR-3 of a VL-region of an antibody directed against human CD3, at least one CDR-3 of a VH-region of an antibody directed against human CD19 and at least one CDR-3 of a VL-region of an antibody directed against human CD19. However, in a most preferred embodiment and as illustrated in the appended examples, the bispecific single chain constructs comprised in the inventive pharmaceutical composition comprise VH and VL regions which comprise not only CDR-3 but also CDR1 and/or CDR2 regions. In particular, CDR-regions, preferably CDR1 regions, more preferably CDR1 regions and CDR2 regions, most preferably CDR1 regions, CDR2 regions and CDR3 regions as defined herein may be employed to generate further bispecific single chain constructs defined herein. Most preferably the bispecific single chain constructs comprised in the inventive pharmaceutical composition are derived from the parental antibodies as disclosed herein and share, as disclosed above, the CDR-3 domain of the VH-region and the CDR-3 domain of the VL-region with said parental antibodies. Yet, it is also envisaged that the bispecific single chain constructs comprised in the inventive pharmaceutical composition also comprises modified CDR regions. It is, e.g. envisaged that in particular CDR2 and/or CDR1 regions (or frameworks or linkers between CDRs) are deimmunized.

In a preferred embodiment of the invention the bispecific single chain antibody construct comprised in the inventive pharmaceutical composition comprises an amino acid sequence selected from the group consisting of (a) an amino acid sequence as depicted in SEQ ID NOs 2, 10 or 14; (b) an amino acid sequence encoded by a nucleic acid sequence as shown in SEQ ID NOs 1, 9 or 13; (c) an amino acid sequence encoded by a nucleic acid sequence hybridizing under stringent conditions to the complementary nucleic acid sequence of (b); and (d) an amino acid sequence encoded by a nucleic acid sequence which is degenerate as a result of the genetic code to a nucleotide sequence of (b).

The term "hybridizing" as used herein refers to polynucleotides/nucleic acid sequences which are capable of hybridizing to the polynucleotides encoding bispecific single chain constructs as defined herein or parts thereof. Therefore, said polynucleotides may be useful as probes in Northern or Southern Blot analysis of RNA or DNA preparations, respectively, or can be used as oligonucleotide primers in PCR analysis dependent on their respective size. Preferably, said hybridizing polynucleotides comprise at least 10, more preferably at least 15 nucleotides in length while a hybridizing polynucleotide of the present invention to be used as a probe preferably comprises at least 100, more preferably at least 200, or most preferably at least 500 nucleotides in length.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Molecular Cloning A Laboratory Manual, Cold Spring Harbor Laboratory (2001) N.Y. Preferred in accordance with the present inventions are polynucleotides which are capable of hybridizing to the polynucleotides of the invention or parts thereof, under stringent hybridization conditions.

"Stringent hybridization conditions" refer, i.e. to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C. Also contemplated are nucleic acid molecules that hybridize to the polynucleotides of the invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH2po4; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As mentioned above, the said variable domains comprised in the herein described bispecific single chain constructs are connected by additional linker sequences. The term "peptide linker" defines in accordance with the present invention an amino acid sequence by which the amino acid sequences of the first domain and the second domain of the monomer of the trimeric polypeptide construct of the invention are linked with each other. An essential technical feature of such peptide linker is that said peptide linker does not comprise any polymerization activity. A particularly preferred peptide linker is characterized by the amino acid sequence Gly-Gly-Gly-Gly-Ser, i.e. Gly$_4$Ser, or polymers thereof, i.e. (Gly$_4$Ser)x, where x is an integer 1 or greater. The characteristics of said peptide linker, which comprise the absence of the promotion of secondary structures are known in the art and described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Also particularly preferred are peptide linkers which comprise fewer amino acid residues. An envisaged peptide linker with less than 5 amino acids comprises 4, 3, 2 or one amino acid(s) wherein Gly-rich linkers are preferred. A particularly preferred "single" amino acid in context of said "peptide linker" is Gly. Accordingly, said peptide linker may consist of the single amino acid Gly. Furthermore, peptide linkers which also do not promote any secondary structures are preferred. The linkage of said domains to each other can be provided by, e.g. genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, N.Y., 2001).

The present invention also provides for a pharmaceutical composition comprising a nucleic acid sequence encoding a bispecific single chain antibody construct as defined above, i.e. a bispecific construct in the format VH(CD19)-VL(CD19)-VH(CD3)-VL(CD3), VH(CD3)-VL(CD3)-VH(CD19)VL(CD19) or VH(CD3)-VL(CD3)-VL(CD19)-VH(CD19). Of these, nucleic acid sequences encoding bispecific constructs of the formats VH(CD19)-VL(CD19)-VH(CD3)-VL(CD3) and VH(CD3)-VL(CD3)-VH(CD19)-VL(CD19) are each especially advantageous for inclusion in such pharmaceutical compositions. In contrast, a nucleic acid sequence encoding a bispecific construct of, for example, the format VH(CD19)-VL(CD19)-VL(CD3)-VH(CD3) is very poorly suited for inclusion in pharmaceutical compositions, the latter being very poorly producible/isolatable.

Said nucleic acid molecule may be a naturally occurring nucleic acid molecule as well as a recombinant nucleic acid molecule. The nucleic acid molecule of the invention may, therefore, be of natural origin, synthetic or semi-synthetic. It may comprise DNA, RNA as well as PNA and it may be a hybrid thereof.

It is evident to the person skilled in the art that regulatory sequences may be added to the nucleic acid molecule of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecules may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that the polynucleotide of the invention can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

Said nucleic acid molecule(s) may be a recombinantly produced chimeric nucleic acid molecule comprising any of the aforementioned nucleic acid molecules either alone or in combination. Preferably, the nucleic acid molecule is part of a vector.

The present invention therefore also relates to a pharmaceutical composition comprising a vector comprising the nucleic acid molecule described in the present invention.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vector to be employed in the generation of the bispecific single chain constructs described herein or to be employed in a pharmaceutical composition of the present invention may, in addition to the nucleic acid sequences of the invention, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, said nucleic acid molecule is operatively linked to said expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous Sarcoma Virus), human elongation factor 1α-promoter, the glucocorticoid-inducible MMTV-promoter (Moloney Mouse Tumor Virus), metallothionein- or tetracyclin-inducible promoters, or enhancers, like CMV enhancer or SV40-enhancer. For expression in white blood cells, it is envisaged that specific promoters can be employed. Said promoters are known in the art and, inter alia, described or mentioned in Hendon (2002), Clin. Immunol. 103, 145-153; Chinnosamy (2000) Blood 96, 1309-1316; Zhang (2003) J. Acq. Immun. Def. Synd. 245-254; Kaiser (2003) Science 299, 495; Hacein-Bay (2002) Int. J. Hemat. 76, 295-298; Hacein-Bay (2002) New Eng. J. Med. 346, 1185-1193; Ainti (2002) Science 296, 2410-2413. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORT1 (GIBCO BRL), pX (Pagano (1992) Science 255, 1144-1147), yeast two-hybrid vectors, such as pEG202 and dpJG4-5 (Gyuris (1995) Cell 75, 791-803), or prokaryotic expression vectors, such as lambda gt11 or pGEX (Amersham-Pharmacia). Beside the nucleic acid molecules coding for the bispecific single chain constructs described herein, the vector may further comprise nucleic acid sequences encoding for secretion signals. Such sequences are well known to the person skilled in the art. Furthermore, depending on the expression system used, leader sequences capable of directing the peptides of the invention to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the bispecific single chain constructs described herein may follow. The invention also relates, accordingly, to hosts/host cells which comprise a vector as defined herein. Such hosts may be useful for in processes for obtaining bispecifc single chain constructs comprised in the pharmaceutical composition of the invention as well as directly in medical/pharmaceutical settings. Said host cells may also comprise transduced or transfected white blood cells, such as lymphocyte cells, preferably adult cells. Such host cells may be useful in transplantation therapies.

Furthermore, the vector as well as the nucleic acid molecule described herein may be employed in gene therapy approaches. Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. In particular, said vectors and/or gene delivery systems are also described in gene therapy approaches in blood, lymphocytes, bone marrow and corresponding stem cells; see, e.g. Hendon (2002), Clin. Immunol. 103, 145-153; Chinnosamy (2000) Blood 96, 1309-1316; Zhang (2003) J. Acq. Immun. Def. Synd. 245-254; Kaiser (2003) Science 299, 495; Hacein-Bay (2002) Int. J. Hemat. 76, 295-298; Hacein-Bay (2002) New Eng. J. Med. 346, 1185-1193; Ainti (2002) Science 296, 2410-2413. The nucleic acid molecules and vectors comprised in the pharmaceutical composition of the invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as a eukaryotic expression system in insect cells for the nucleic acid molecules of the invention. The introduction and gene therapeutic approach should, preferably, lead to the expression of a functional bispecific single chain construct as defined herein, whereby said expressed antibody molecule is particularly useful in the treatment, amelioration and/or prevention of B-cell related malignancies as defined herein. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the bispecific single chain constructs may follow; see, e.g., the appended examples.

Therefore, in further embodiments of the invention, a pharmaceutical composition is provided which comprising a vector encoding a bispecific single chain construct in the format $V_H(CD19)$-$V_L(CD19)$-$V_H(CD3)$-$V_L(CD3)$, $V_H(CD3)$-$V_L(CD3)$-$V_H(CD19)$-$V_L(CD19)$ or $V_H(CD3)$-$V_L(CD3)$-$V_L(CD19)$-$V_H(CD19)$ or a host transformed or transfected with said vector.

The pharmaceutical composition of the invention may also comprise a proteinaceous compound capable of providing an additional activation signal for immune effector cells. Such compounds may comprise, but are not limited to CD28 engagers, ICOS engagers, 4-1BB engagers, OX40 engagers, CD27 engagers, CD30 engagers, NKG2D engagers, IL2-R engagers or IL12-R engagers. In the light of the present invention, said "proteinaceous compounds" providing an activation signal for immune effector cells" may be, e.g. a further primary activation signal, or costimulatory (second) signal or any other accessory (third) activation signal. Examples are a TCR or TCR-like signal. Preferred formats of proteinaceous compounds comprise additional bispecific antibodies and fragments or derivatives thereof, e.g. bispecific scFv. Proteinaceous compounds can comprise, but are not limited to, scFv fragments specific for 4-1BB, OX 40, CD27, CD70 or the receptors for B7-RP 1, B7-H3 as well as scFv fragments specific for the T cell receptor or superantigens. Superantigens directly bind to certain subfamilies of T cell receptor variable regions in an MHC-independent manner thus mediating the primary T cell activation signal. The proteinaceous compound may also provide an activation signal for an immune effector cell which is a non-T cell. Examples for immune effector cells which are non-T cells comprise, inter alia, NK cells.

In a further embodiment of the present invention, a process for the production of a pharmaceutical composition of the invention is provided, said process comprises culturing a host defined above under conditions allowing the expression of the bispecific single chain antibody construct as defined herein and recovering the produced bispecific single chain antibody construct from the culture. The corresponding process is illustrated in the appended examples.

In a most preferred embodiment, the invention relates to the use of a bispecific single chain antibody construct, a nucleic acid sequence, a vector and/or a host as defined herein for the preparation of a pharmaceutical composition for the prevention, treatment or amelioration of a proliferative disease, a mimimal residual cancer, a tumorous disease, an inflammatory disease, an immunological disorder, an autoimmune disease, an infectious disease, a viral disease, allergic reactions, parasitic reactions, graft-versus-host diseases host-versus-graft diseases or B-cell malignancies, wherein said pharmaceutical composition optionally further comprises a proteinaceous compound capable of providing an activation signal for immune effector cells.

Accordingly, a method for the prevention, treatment or amelioration of a proliferative disease, a mimimal residual cancer, a tumorous disease, an inflammatory disease, an immunological disorder, an autoimmune disease, an infectious disease, viral disease, allergic reactions, parasitic reactions, graft-versus-host diseases, host-versus-graft diseases, or B-cell malignancies is provided, whereby said method comprises the step of administering to a subject in need of such a prevention, treatment or amelioration a pharmaceutical composition of the invention. Most preferably said subject is a human.

The tumorous disease to be treated with the pharmaceutical composition of the invention may be a minimal residual cancer, for example, a minimal residual lymphoma or leukemia.

The autoimmune disease to be treated with the pharmaceutical composition of the invention may be in inflammatory autoimmune disease, for example, rheumatoid arthritis.

In accordance with this invention, it is also envisaged that a bispecific single chain antibody construct, a nucleic acid sequence, a vector and/or a host as described herein is/are used for the preparation of a pharmaceutical composition for depletion of B-cells.

The B cell malignancy to be treated with the pharmaceutical composition of the invention is in a most preferred embodiment non-Hodgkin lymphoma, B-cell leukemias or Hodgkin lymphoma. Accordingly, the present invention provides for a method for the treatment of B-cell malignancies, B-cell mediated autoimmune diseases or the depletion of B-cells and/or for a method delaying a pathological condition which is caused by B-cell disorders comprising administering the pharmaceutical composition of the invention into a mammal, preferably a human, affected by said malignancies, disease and/or pathological condition.

Finally, the invention provides for a kit comprising a bispecific single chain antibody construct, a nucleic acid sequence, a vector and/or a host as defined above. Said kit is particularly useful in the preparation of the pharmaceutical composition of the present invention and may, inter alia, consist of a container useful for injections or infusions. Advantageously, the kit of the present invention further comprises, optionally (a) buffer(s), storage solutions and/or remaining reagents or materials required for the conduct of medical or scientific purposes. Furthermore, parts of the kit of the invention can be packaged individually in vials or bottles or in combination in containers or multicontainer units. The kit of the present invention may be advantageously used, inter alia, for carrying out the method of the invention and could be employed in a variety of applications referred herein, e.g., as research tools or medical tools. The manufacture of the kits preferably follows standard procedures which are known to the person skilled in the art.

These and other embodiments are disclosed and encompassed by the description and. Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com.

The figures show:

FIG. 1A: Schematic composition of VL/VH domain arrangements in anti-CD-19/ anti-CD3 single chain bispecific antibodies showing the binding sites of PCR primers. A1, A2, B1 and B2 denote the positions, from the N-terminus to the C-terminus of the various V-regions used in constructing the anti-CD19/anti-CD3 single chain bispecific antibodies. $(G_4S_1)$ and $(G_4S_1)_2$ linkers disclosed as SEQ ID NOS: 71 and 83, respectively.

FIG. 1B: Schematic composition of VL/VH domain arrangements in anti-CD19/anti-CD3 single chain bispecific antibodies showing the recognition site of restriction enzymes (L=Leader peptide). A1, A2, B1 and B2 denote the positions, from the N-terminus to the C-terminus of the various V-regions used in constructing the anti-CD19/anti-CD3 single chain bispecific antibodies. $(G_4S_1)$ and $(G_4S_1)_3$ linkers disclosed as SEQ ID NOS: 71 and 69, respectively.

FIG. 2: Bispecific single chain antibody elution pattern from a Zn-chelating Fractogel® column (IMAC) at 280 nm. The bottom line showing a first, minor step at 600 ml retention time and a second, major step at 700 ml indicates the theoretical gradient of elution buffer containing 0.5 M imidazole. High adsorption at 280 nm from 100-500 ml retention time was due to non-bound protein in the column flow through. Protein from the elution peak at 670.05 ml retention time was used for further purification.

Figure 3:
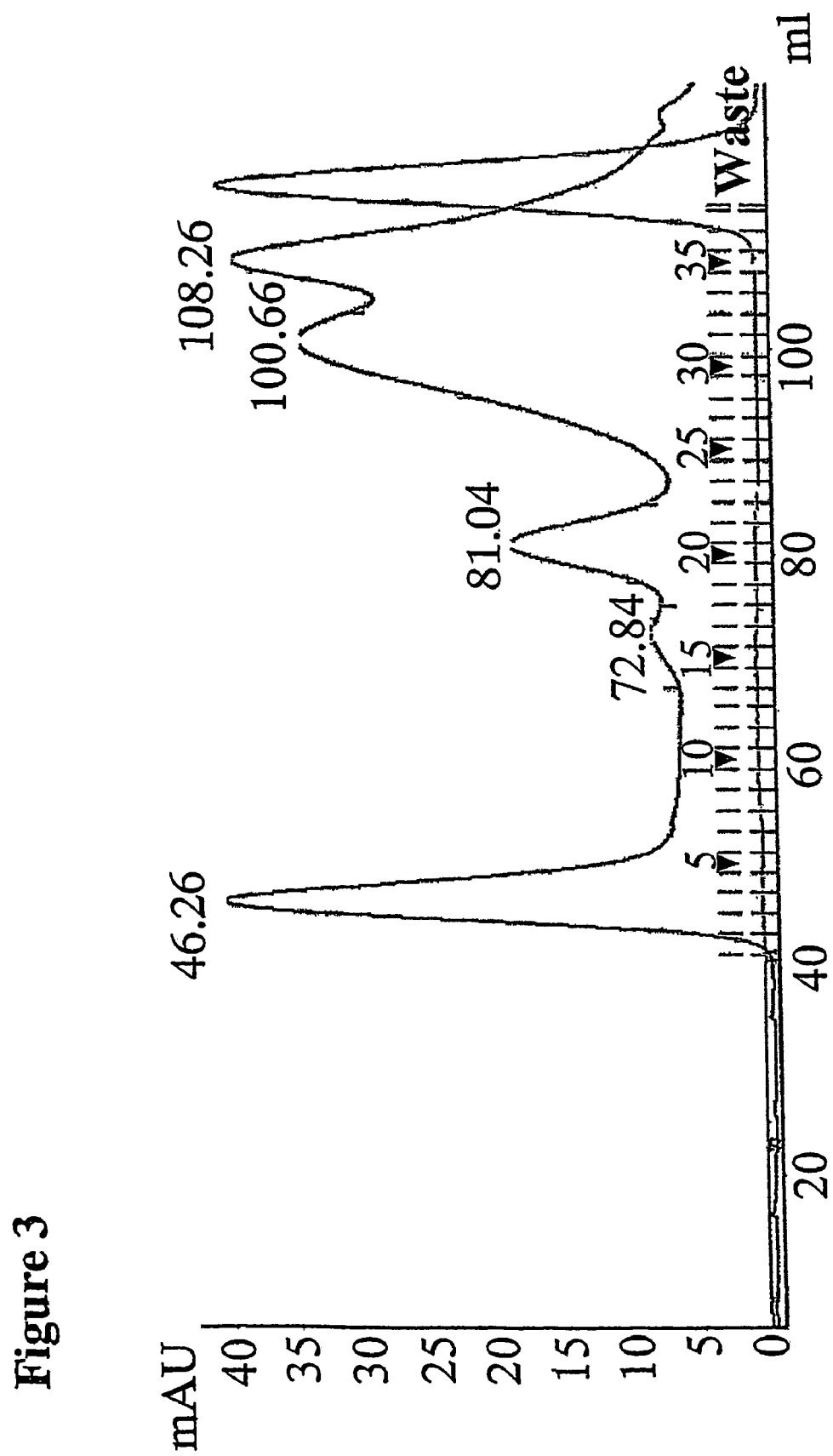

FIG. 3: Bispecific single chain antibody elution pattern from a Sephadex S200 gel filtration column at 280 nm. The protein peak at 81.04 ml retention time containing bispecific antibodies against CD3 and CD19 corresponds to a molecular weight of 52 kD. Fractions were collected from 50-110 ml retention time and were indicated with black arrows numbered from 5-35.

Figure 4:
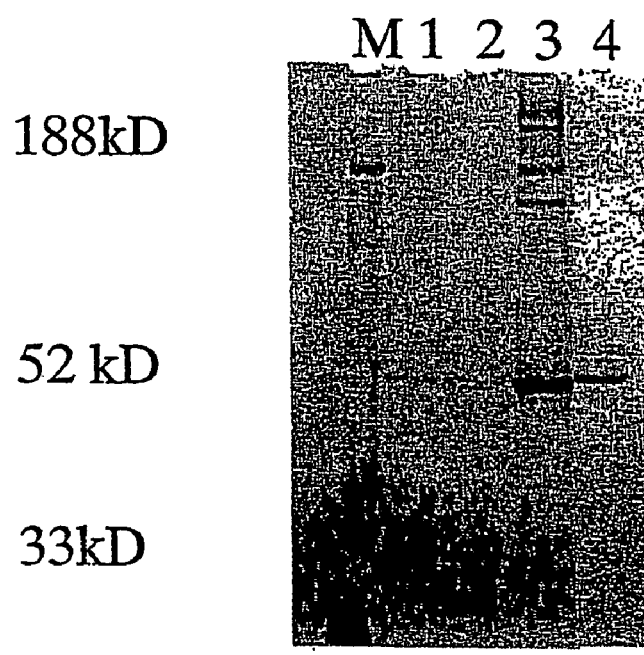

FIG. 4: Representative SDS-PAGE analysis of protein fractions of bispecific single chain antibodies. Lane M: Molecular weight marker Lane 1: cell culture supernatant; lane 2: IMAC flow-through; lane 3: IMAC eluate; lane 4: purified antibody against CD19 and CD3 obtained from gel filtration (Sephadex 200).

Figure 5:
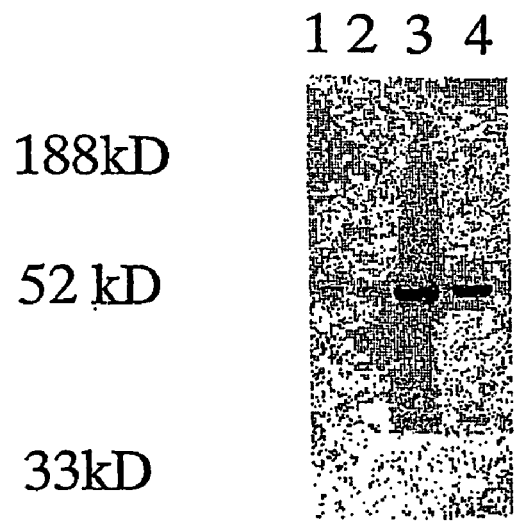

FIG. 5: Representative western blot analysis of purified bispecific single chain antibody fractions. Western blot analysis of purified bispecific protein was performed with antibodies directed against the HisTag (PentaHis, Qiagen) and goat anti mouse Ig labelled with alkaline phosphatase. Lane 1: cell culture supernatant; lane 2: IMAC flow-through; lane 3: IMAC eluate; lane 4: purified antibody against CD19 and CD3 obtained from gel filtration (Sephadex 200).

Figure 6A:
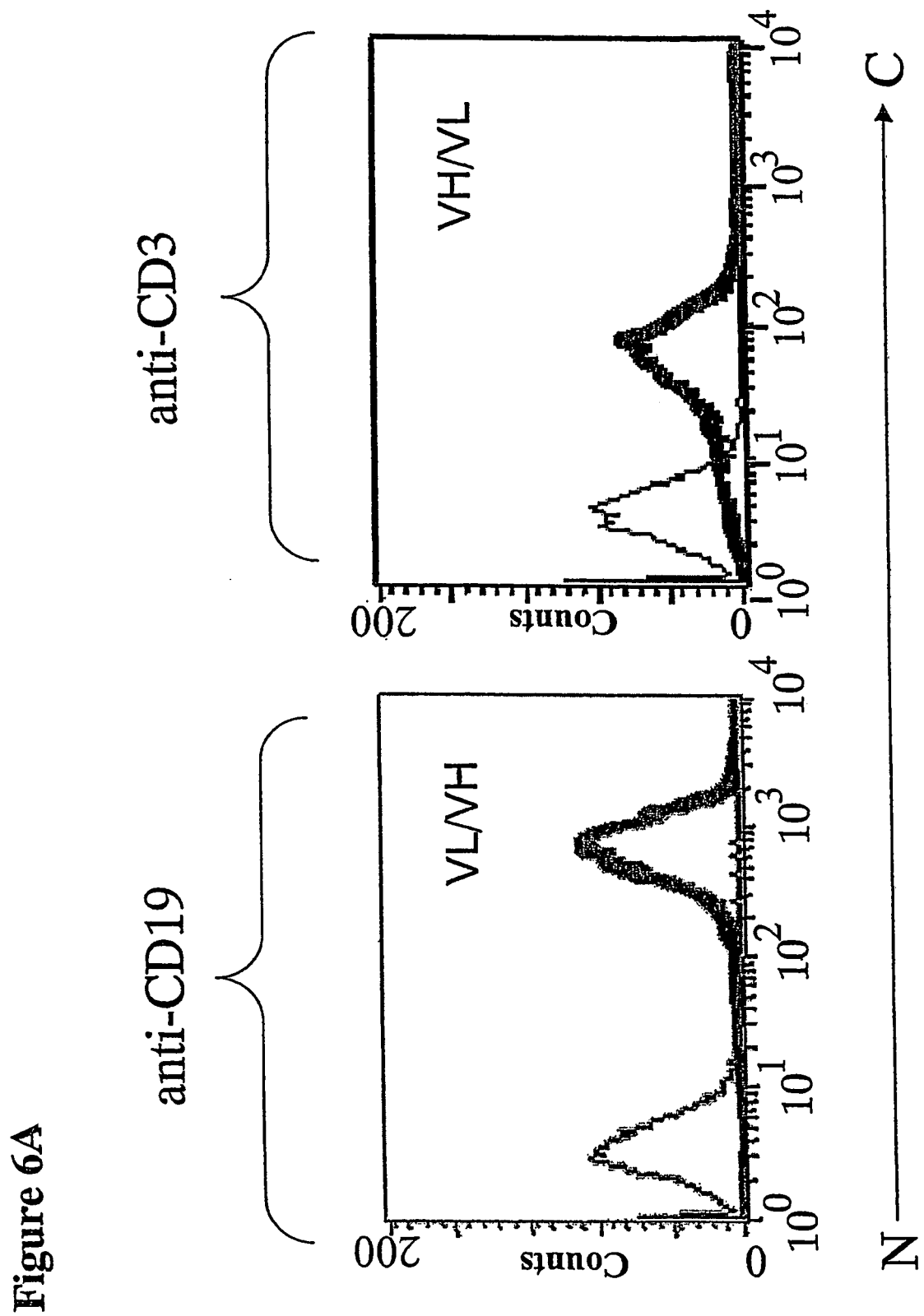

FIG. 6A: Binding data for the anti-CD19 (VL/VH)×anti-CD3 (VH/VL) construct as measured by FACS analysis on Nalm 6 (CD19+) and Jurkat (CD3+) cells. The left peak is the control; the right peak is the measurement of the fluorescence shift for the binding specificity of interest. A shift to the right indicates binding of the construct to CD19 or CD3, respectively. Arrangement of VH and VL domains is indicated from N to C terminus (N→C).

Figure 6B:
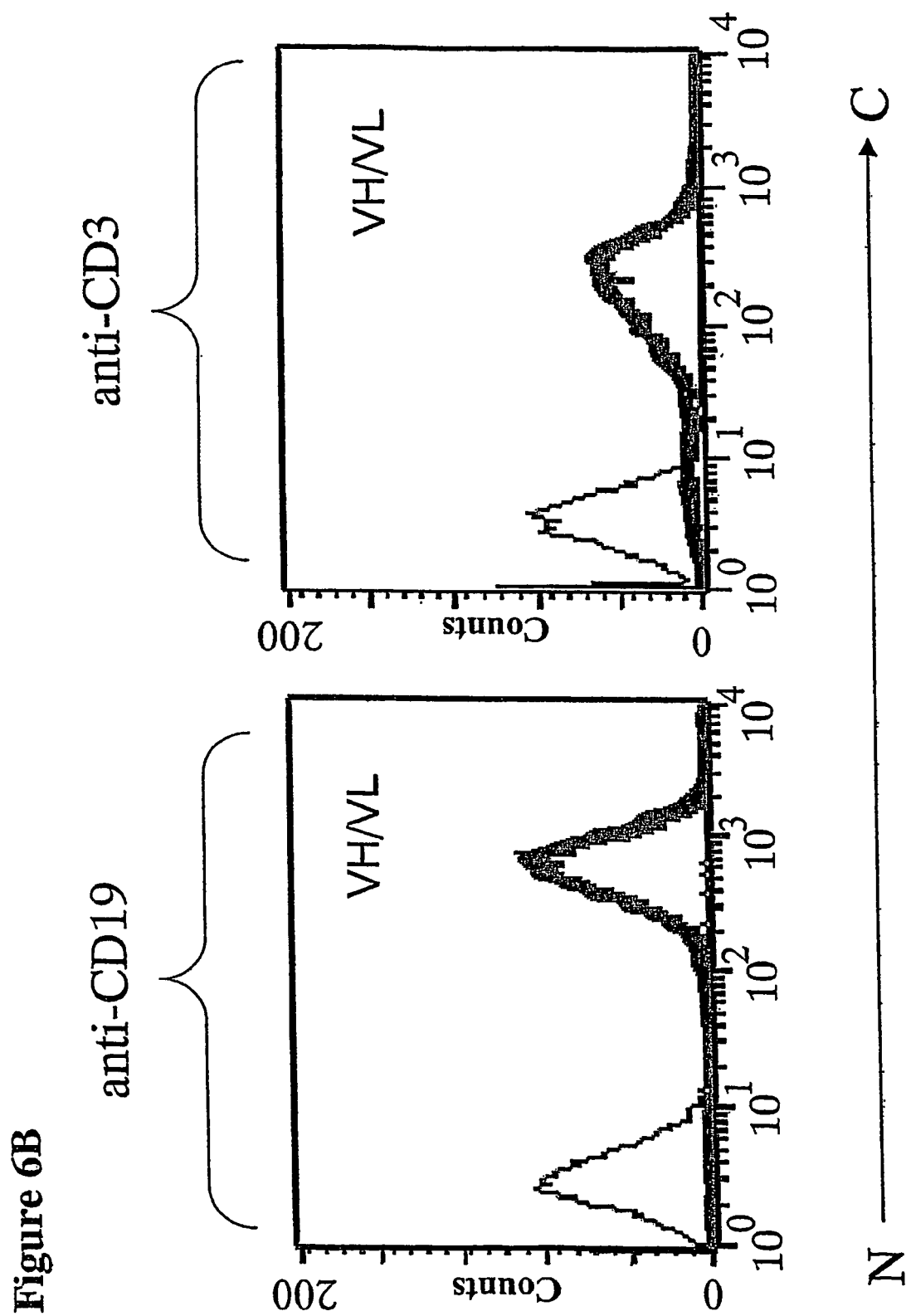

FIG. 6B: Binding data for the anti-CD19 (VH/VL)×anti-CD3 (VH/VL) construct as measured by FACS analysis on Nalm 6 (CD19+) and Jurkat (CD3+) cells. The left peak is the control; the right peak is the meacurement of the fluorescence shift for the binding specificity of interest. A shift to the right indicates binding of the construct to CD19 or CD3, respectively. Arrangement of VH and VL domains is indicated from N to C terminus (N→C).

Figure 6C:
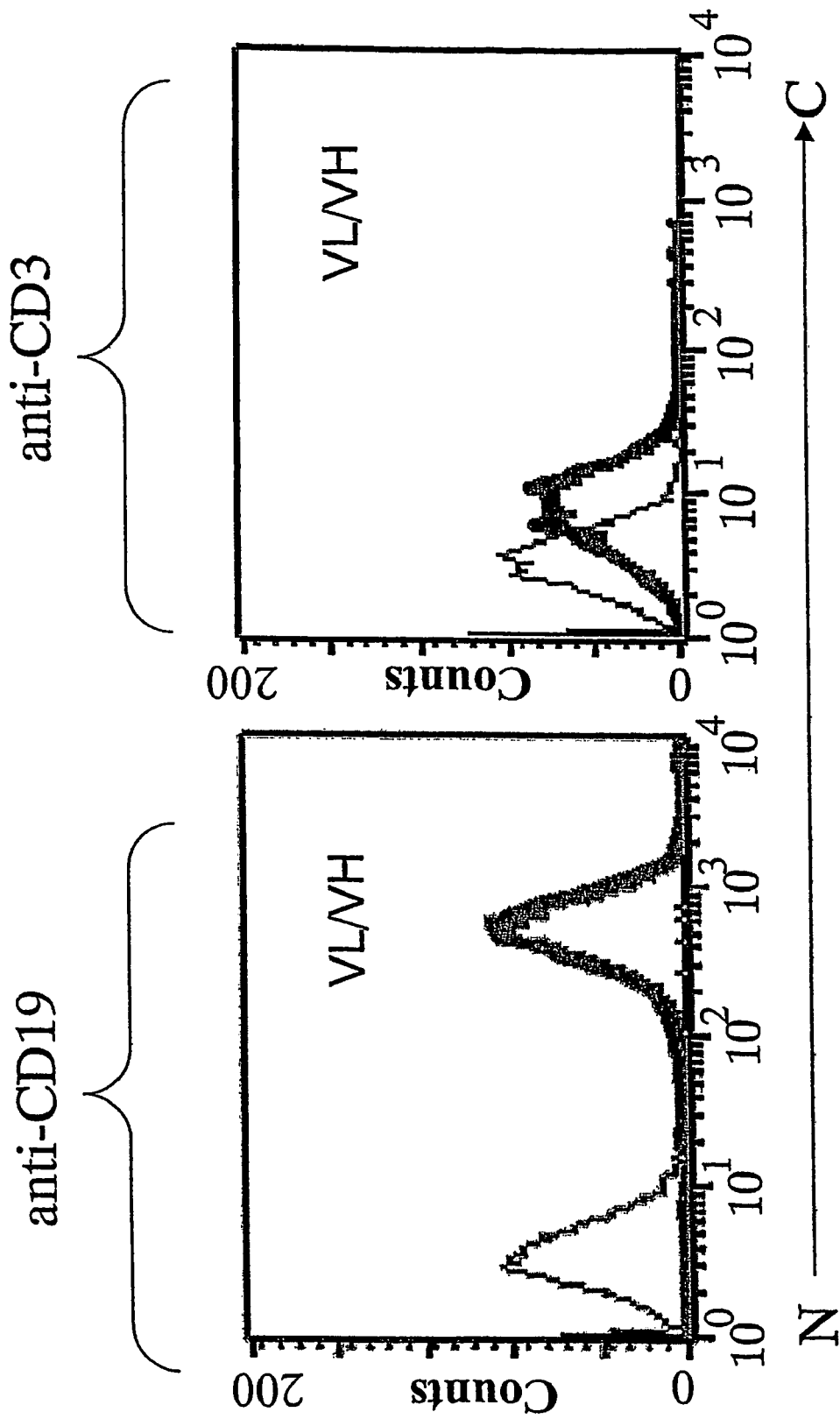

FIG. 6C: Binding data for the anti-CD19 (VL/VH)×anti-CD3 (VL/VH) construct as measured by FACS analysis on Nalm 6 (CD19+) and Jurkat (CD3+) cells. The left peak is the control; the right peak is the meacurement of the fluorescence shift for the binding specificity of interest. A shift to the right indicates binding of the construct to CD19 or CD3, respectively. Arrangement of VH and VL domains is indicated from N to C terminus (N→C).

Figure 6D:
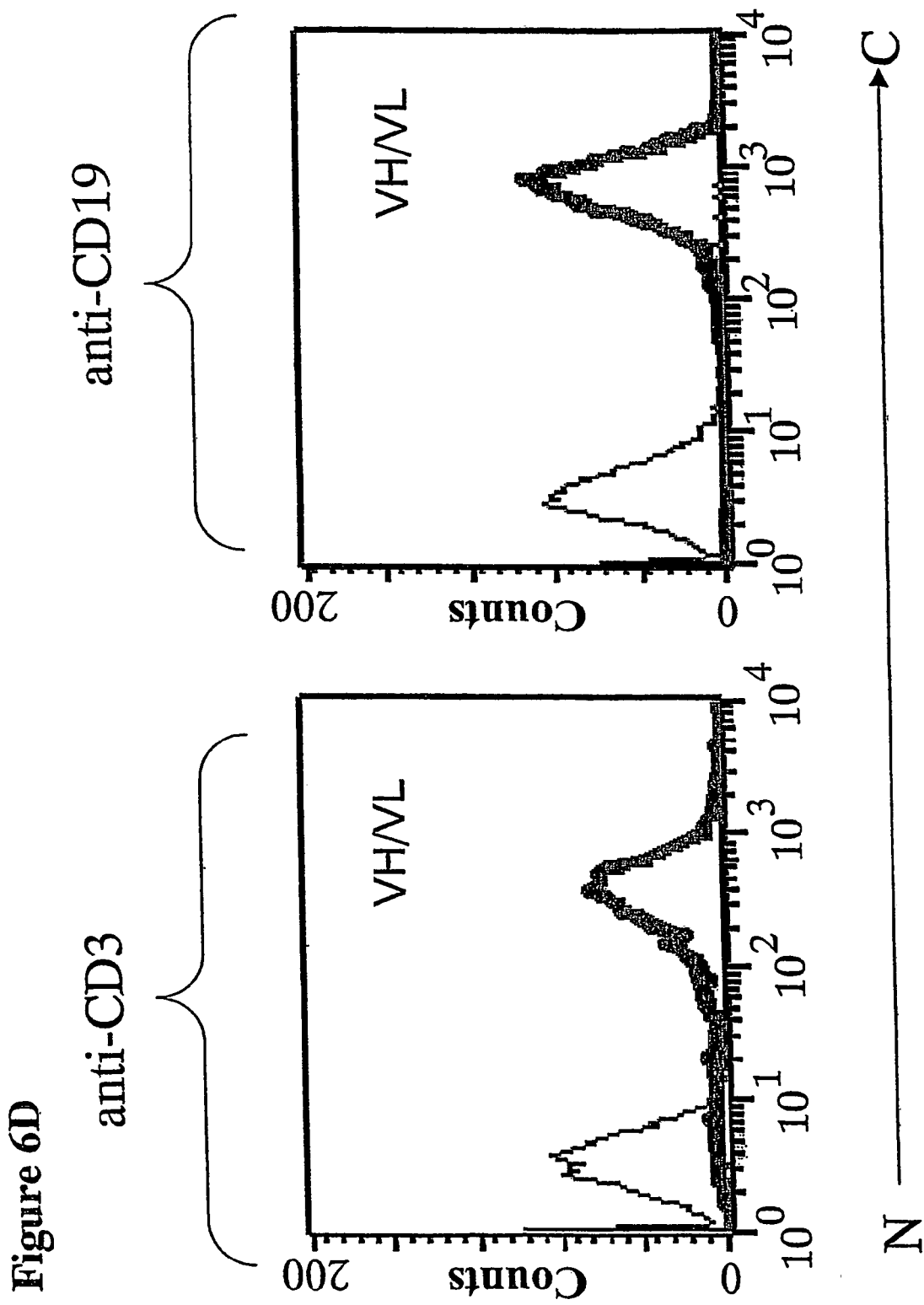

FIG. 6D: Binding data for the anti-CD3 (VH/VL)×anti-CD19 (VH/VL) construct as measured by FACS analysis on Nalm 6 (CD19+) and Jurkat (CD3+) cells. The left peak is the control; the right peak is the meacurement of the fluorescence shift for the binding specificity of interest. A shift to the right indicates binding of the construct to CD19 or CD3, respectively. Arrangement of VH and VL domains is indicated from N to C terminus (N→C).

Figure 6E:
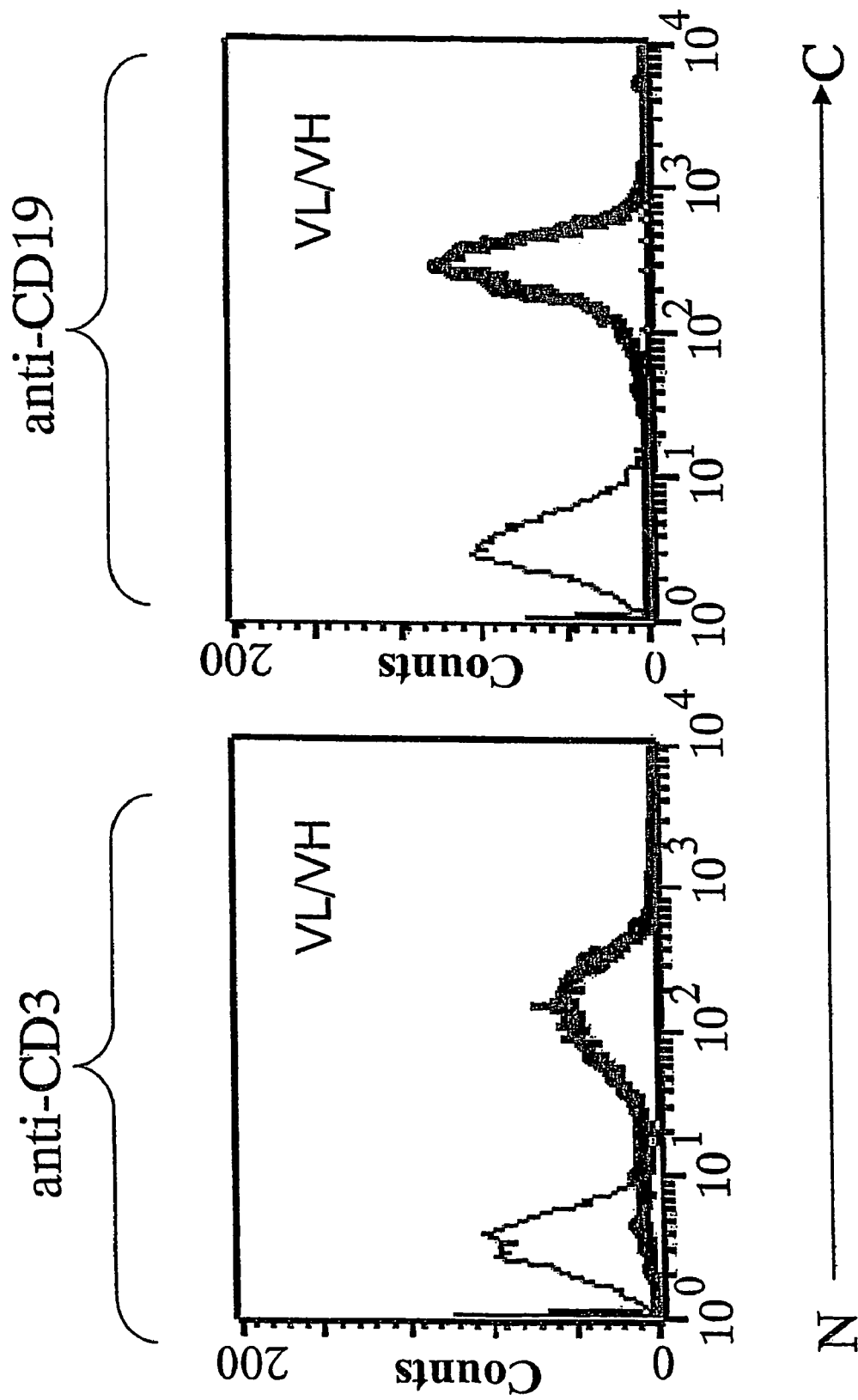

FIG. 6E: Binding data for the anti-CD3 (VL/VH)×anti-CD19 (VL/VH) construct as measured by FACS analysis on Nalm 6 (CD19+) and Jurkat (CD3+) cells. The left peak is the control; the right peak is the meacurement of the fluorescence shift for the binding specificity of interest. A shift to the right indicates binding of the construct to CD19 or CD3, respectively. Arrangement of VH and VL domains is indicated from N to C terminus (N→C).

Figure 6F:
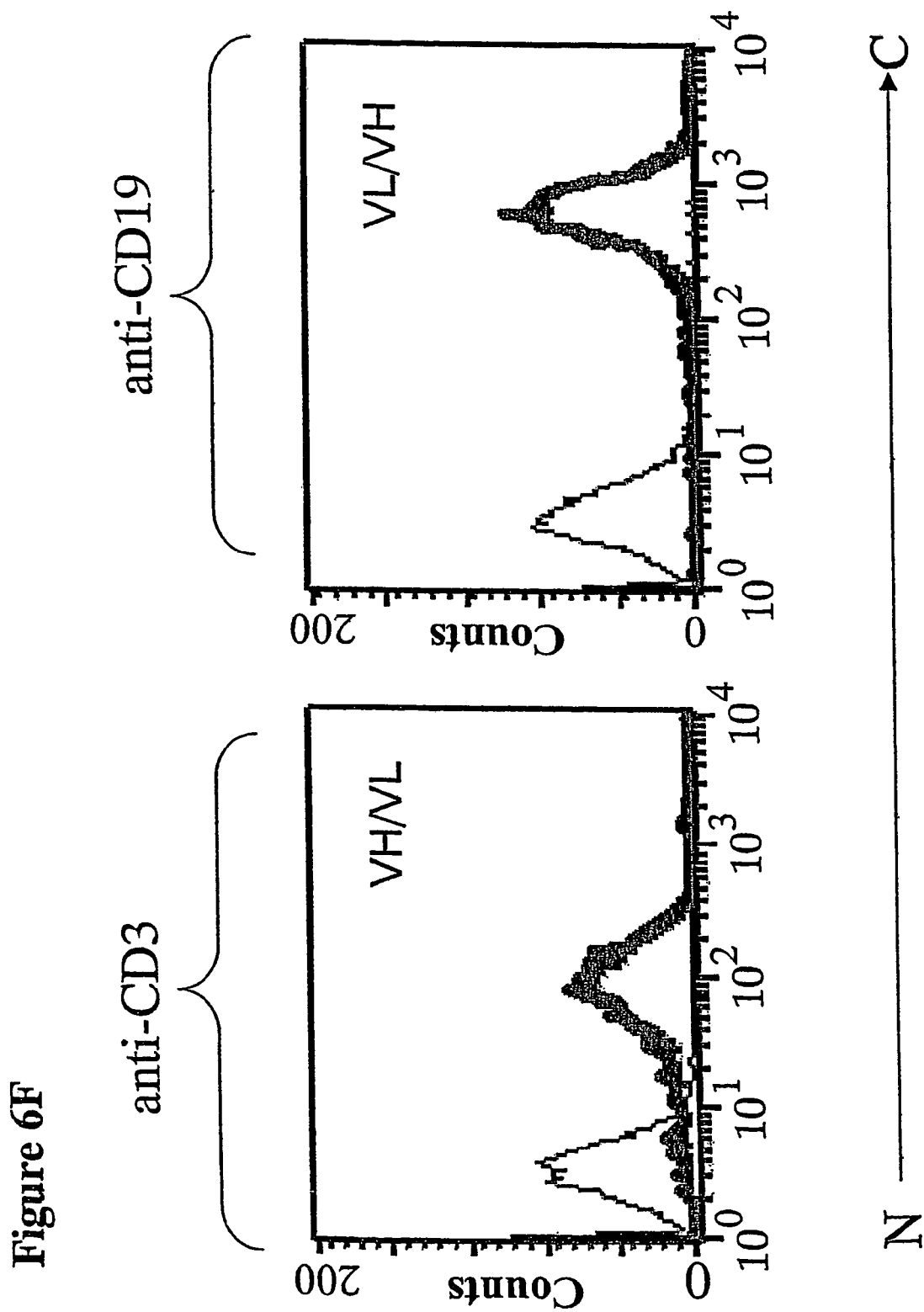

FIG. 6F: Binding data for the anti-CD3 (VH/VL)×anti-CD19 (VL/VH) construct as measured by FACS analysis on Nalm 6 (CD19+) and Jurkat (CD3+) cells. The left peak is the control; the right peak is the meacurement of the fluorescence shift for the binding specificity of interest. A shift to the right indicates binding of the construct to CD19 or CD3, respectively. Arrangement of VH and VL domains is indicated from N to C terminus (N→C).

Figure 7:
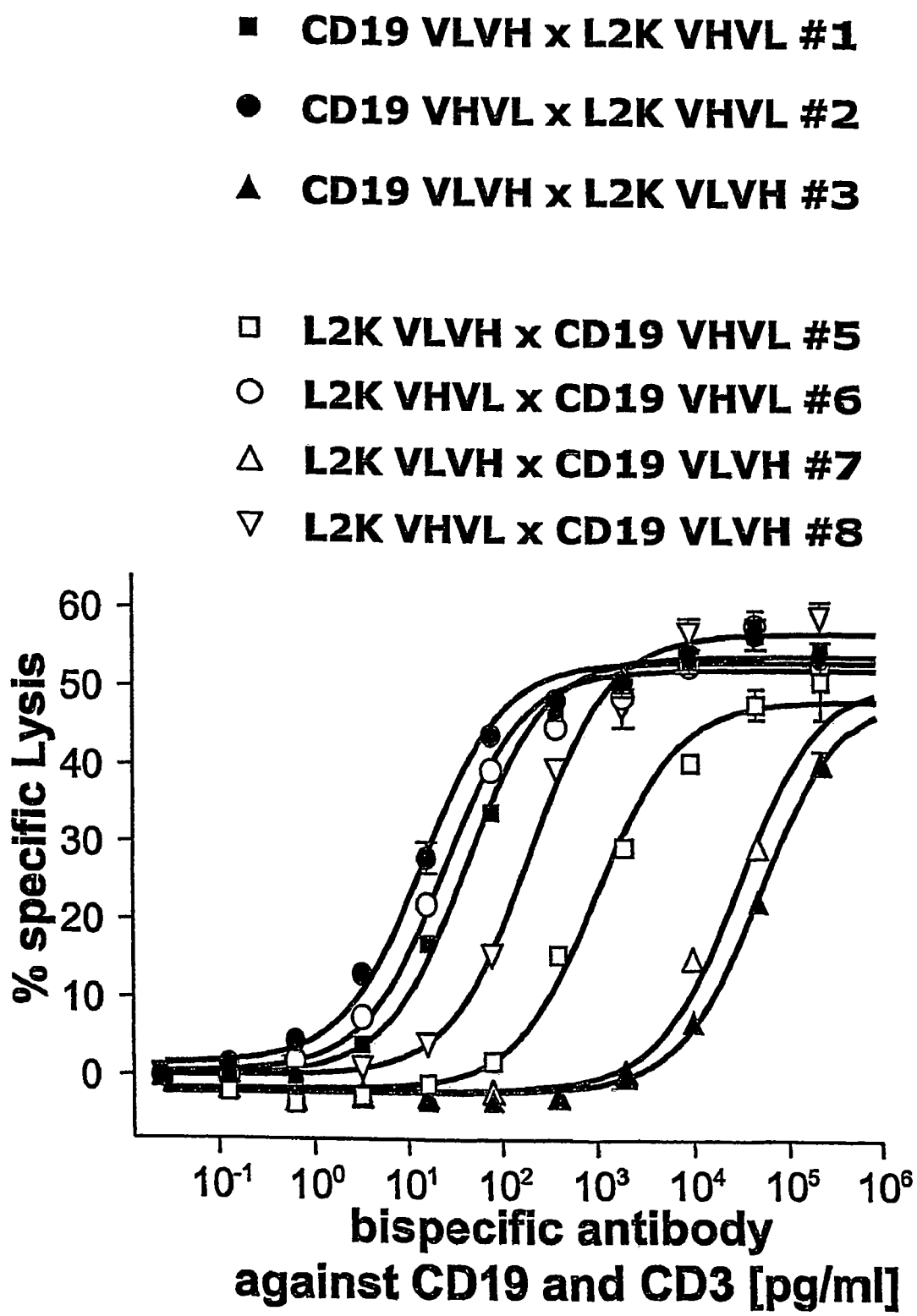

FIG. 7: Cytotoxicity data for selected domain-rearranged anti-CD3/anti-CD19 constructs. CB15 T cell clone and NALM6 cells were used in an E:T ratio of 1:10. NALM6 target cells were labelled with calcein. Calcein release after cell lysis was determined by FACS analysis.

Figure 8:
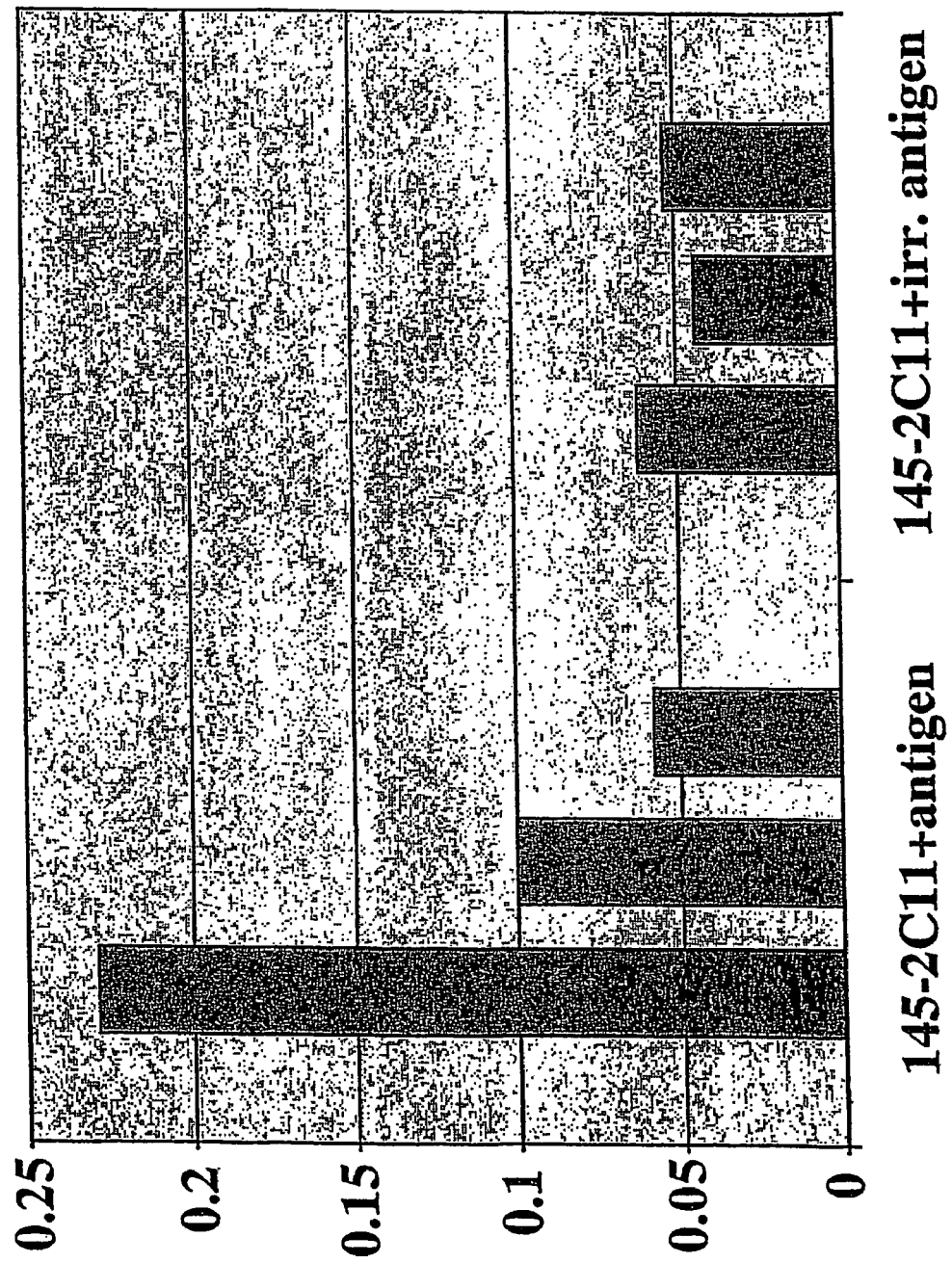

FIG. 8: Binding of the 145-2C11 antibody to the recombinant, purified extracellular domain of the murine CD3 epsilon chain in ELISA. The ELISA was performed as described in Example 5, paragraph 1. The graph depicts absorption values for antigen preparation or an irrelevant antigen binding to the coated 145-2C11 antibody. Samples were done in 1:5, 1:25 and 1:125 dilution.

Figure 9:
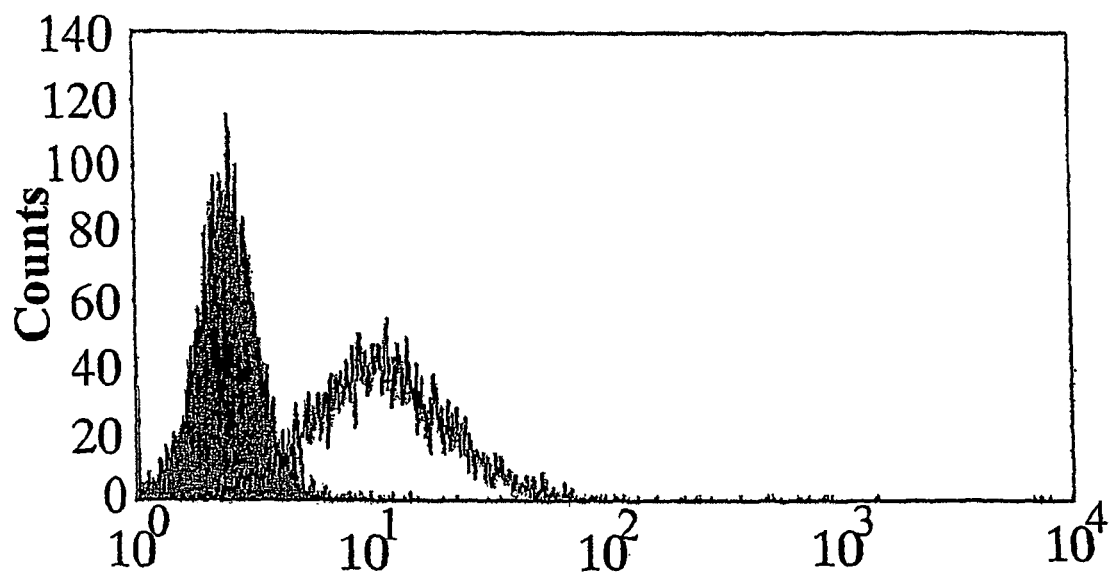

FIG. 9: FACS binding-analysis of the 145-2C11 antibody on Jurkat cells transfected with the murine CD3 epsilon chain surface antigen. The FACS staining was performed as described in Example 5, paragraph 2. The filled histogram represents cells incubated with the isotype control. The open histogram shows cells incubated with the 145-2C11 antibody.

Figure 10:
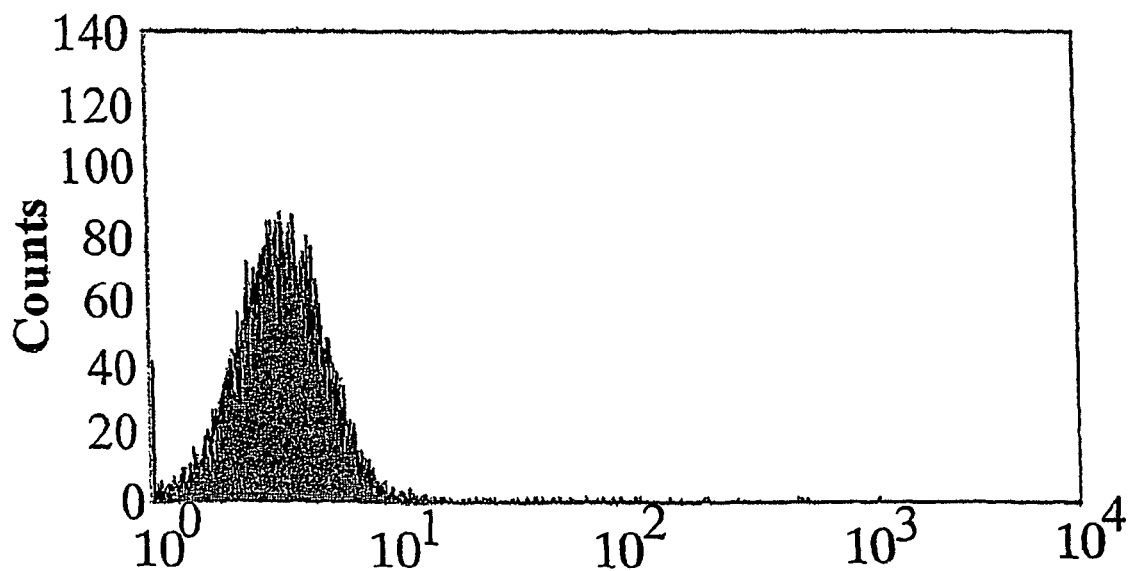

FIG. 10: FACS binding-analysis of the 145-2C11 antibody on untransfected Jurkat cells. The FACS staining was performed as described in Example 5, paragraph 2. The filled histogram represents cells incubated with the isotype control. The open histogram, superimposed on the filled histogram, represents cells incubated with the 145-2C11 antibody. 145-2C11 did not bind to Jurkat cells.

Figure 11:
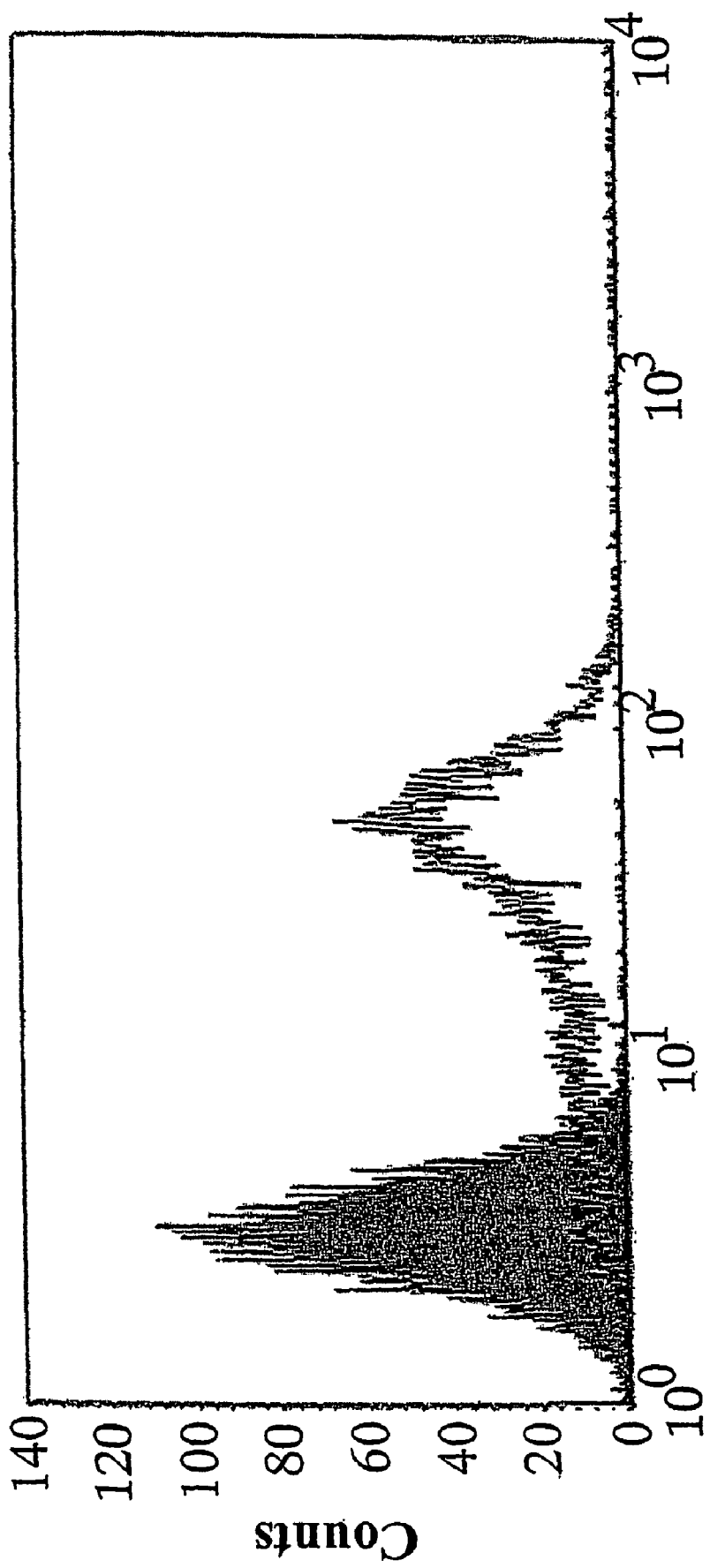

FIG. 11: FACS binding-analysis of the 145-2C11 antibody on CTLL2 cells. The FACS staining was performed as described in Example 5, paragraph 3. The filled histogram represents cells incubated with the isotype control. The open histogram indicates that the 145-2C11 antibody bound to CTLL2 cells.

The invention will now be described by reference to the following examples which are merely illustrative and are not to be construed as a limitation of the invention's scope.

EXAMPLE 1

Construction of CD19×CD3 and CD3×CD19 Single Chain Bispecific Antibodies Comprising Various Domain Rearrangements Generally, bispecific single antibody chain molecules, each comprising a domain with binding specificity for the human CD3 antigen as well as a domain with binding specificity for the human CD19 antigen, were designed as set out in the following Table 1:

TABLE 1

Formats of bispecific single antibody chain molecules comprising anti-CD3 and anti-CD19 specificities

| Construct Number | SEQ ID Nos (nuc/prot) | Formats of protein constructs (N → C) |
|---|---|---|
| 1 | 29/30 | VL(CD19)-VH(CD19)-VH(CD3)-VL(CD3) |
| 2 | 1/2 | VH(CD19)-VL(CD19)-VH(CD3)-VL(CD3) |
| 3 | 3/4 | VL(CD19)-VH(CD19)-VL(CD3)-VH(CD3) |
| 4 | 5/6 | VH(CD19)-VL(CD19)-VL(CD3)-VH(CD3) |
| 5 | 7/8 | VL(CD3)-VH(CD3)-VH(CD19)-VL(CD19) |
| 6 | 9/10 | VH(CD3)-VL(CD3)-VH(CD19)-VL(CP19) |
| 7 | 11/12 | VL(CD3)-VH(CD3)-VL(CD19)-VH(CD19) |
| 8 | 13/14 | VH(CD3)-VL(CD3)-VL(CD19)-VH(CD19) |

The variable light-chain (VL) and variable heavy-chain (VH) domains from the HD37 hybridoma (Pezzutto, J. Immunol. 138 (1997), 2793-9) were cloned according to standard PCR methods (Orlandi, Proc. Natl. Acad. Sci. USA 86 (1989), 3833-7). cDNA synthesis was carried out with oligo dT primers and Taq polymerase. For the amplification of the anti-CD19 V domains via PCR, the primers 5' L1 (SEQ ID NO: 37) and 3' K (SEQ ID NO: 38), flanking the VL domain, and 5'H1 (SEQ ID NO: 39) and 3'G (SEQ ID NO: 40) for the heavy chain were used, based on primers described by Dübel, J. Immunol. Methods 175 (1994), 89-95. The cDNA of the anti-CD3 scFv fragment was kindly provided by Traunecker (Traunecker, EMBO J. 10 (1991) 3655-9).

Construct 1 as set out in Table 1 was constructed as follows. To obtain an anti-CD19 scFv-fragment, the corresponding VL- and VH-regions cloned into separate plasmid vectors, served as templates for a VL- and VH-specific PCR using the oligonucleotide primer pairs 5'VLB5RRV (SEQ ID NO: 41)/3'VLGS15 (SEQ ID NO: 42) and 5'VHGS15 (SEQ ID NO: 43)/3'VHBspEI (SEQ ID NO: 28), respectively. Overlapping complementary sequences were introduced into the PCR-products that combined to form the coding sequence of 15-amino acid (Gly$_4$Ser$_1$)$_3$-linker during the subsequent fusion-PCR. This amplification step was performed with the primer pair 5'VLB5RRV (SEQ ID NO: 41)/3'VHBspE1 (SEQ ID NO: 28) and the resulting fusion product (or rather anti-CD19 scFv-fragment) was cleaved with the restriction enzymes. EcoRV and BspE1 and thus cloned into the bluescript KS-vector (Statagene), containing the (EcoR1/Sal1-cloned) coding sequence of the anti-17-1A/anti-CD3 bispecific single-chain antibody (actually the version without the Flag-tag) (Kufer, Cancer Immunol. Immunother. 45 (1997) 193). Thereby the anti-17-1A-specificity was replaced by the anti-CD19-scFV-fragment, preserving the 5-amino acid Gly$_4$Ser-linker that connects the C-terminal anti-CD3 scFv-fragment. Subsequently, the DNA-fragment encoding the anti-CD19/anti-CD3 bispecific single-chain antibody with the domain arrangement VL$_{CD19}$-VH$_{CD19}$-VH$_{CD3}$-VL$_{CD3}$ was subcloned into the EcoR1/Sal1 sites of the described expression vector pEF-DHFR (Mack, Proc. Natl. Acad. Sci. USA 92 (1995), 7021-5). The resulting plasmid-DNA was transfected into DHFR-deficient CHO-cells by electroporation. The selection, gene amplification and protein production were performed as previously described (Mack, Proc. Natl. Acad. Sci. USA 92 (1995), 7021-5). The DNA sequence corresponding to construct 1 is as set out above in Table 1 is as represented in SEQ ID NO: 29. The protein translation of this DNA sequence (without leader but including the stop codon) is as represented in SEQ ID NO: 30.

The remaining constructs as set out above in Table 1 were constructed as follows. The DNA sequence corresponding to SEQ ID NO: 29, the protein translation of which (without leader but including the stop codon) is represented by SEQ ID NO: 30 was used as PCR template in designing the various anti-CD3/anti-CD19 single chain bispecific antibodies set out above in Table 1.

To generate a VH-VL arrangement of CD19 in position A1 and A2 (as defined in FIGS. 1A and 1B), PCR with the respective primer combination 5'VHCD19BsrGI (SEQ ID NO: 24) and 3'VHCD19GS15 (SEQ ID NO: 25) or 5'VLCD19GS15 (SEQ ID NO: 26) and 3'VLCD19BspEI (SEQ ID NO: 27) was used. During these PCR cycles overlapping complementary sequences were introduced into the PCR-products forming the coding sequence of a 15 amino acid linker during the subsequent fusion PCR. The amplified VL and VH domains were fused in a second PCR reaction (fusion PCR) in which only the outer primers, namely 5'VHCD19BsrGI (SEQ ID NO: 24) and 3'VLCD19BspEI (SEQ ID NO: 27), and both amplicants were required.

A similar procedure employing other combinations of primers was used to construct other domain arrangements. A set of appropriate primers was designed to perform multiple PCR-based cloning steps, finally resulting in the various VL-VH domain arrangements. The primer combinations used are listed in the following table:

TABLE 2

Overview of PCR-based cloning steps used for construction of positions A1 and A2 of constructs 2, 3, 4, 5, 6, 7 and 8 as shown in Table 1

| PCR step | Primers Used | | PCR step | Used Primers | Resulting N-terminal Domain order |
|---|---|---|---|---|---|
| PCR A1 | 5'VHCD19BsrGI (SEQ ID NO: 24) | 3'VHCD19GS15 (SEQ ID NO: 25) | Fusion PCR | 5'VHCD19BsrGI (SEQ ID NO: 24) | CD 19 VH-VL |
| PCR A2 | 5'VLCD19GS15 (SEQ ID NO: 26) | 3'VLCD19BspEI (SEQ ID NO: 27) | A1 + A2 | 3'VLCD19BspEI (SEQ ID NO: 27) | |

TABLE 2-continued

Overview of PCR-based cloning steps used for construction of positions
A1 and A2 of constructs 2, 3, 4, 5, 6, 7 and 8 as shown in Table 1

| PCR step | Primers Used | | PCR step | Used Primers | Resulting N-terminal Domain order |
|---|---|---|---|---|---|
| PCR A1 | 5'VHL2KBsrGI (SEQ ID NO: 20) | 3'VHL2KGS15 (SEQ ID NO: 21) | Fusion PCR | 5'VHL2KBsrGI (SEQ ID NO: 20) | Anti-CD3 VH-VL |
| PCR A2 | 5' VLL2KGS15 (SEQ ID NO: 22) | 3'VLL2KBspEI (SEQ ID NO: 23) | A1 + A2 | 3'VLL2KBspEI (SEQ ID NO: 23) | |
| PCR A1 | 5'VLL2KBsrGI (SEQ ID NO: 31) | 3'VLL2KGS15 (SEQ ID NO: 32) | Fusion PCR | 5'VLL2KBsrGI (SEQ ID NO: 31) | Anti-CD3 VL-VH |
| PCR A2 | 5'VHL2KGS15 (SEQ ID NO: 33) | 3'VHL2KBspEI (SEQ ID NO: 34) | A1 + A2 | 3'VHL2KBspEI (SEQ ID NO: 34) | |

In order to change the VH-VL domain arrangement in the C-terminal position, namely positions B1 and B2 as defined in FIGS. 1A and 1B, the following primers comprising the designated restriction enzyme recognition sites were designed to perform the PCR-based cloning steps.

TABLE 3

Overview of PCR-based cloning steps used for construction
of positions B1 and B2 of constructs 2, 3, 4,
5, 6, 7 and 8 as shown in Table 1

| PCR step | Primers used | | Resulting C-terminal domain order |
|---|---|---|---|
| PCR B1 + B2 | 5' VLCD19BspEIGS (SEQ ID NO: 19) | 3' VHCD19BspEI (SEQ ID NO: 35) | CD 19 VL-VH |
| | 5' VHCD19BspEIGS (SEQ ID NO: 17) | 3'VLCD19BspEI (SEQ ID NO: 18) | CD19 VH-VL |
| | 5' VLL2KBspEIGS (SEQ ID NO: 15) | 3'VHL2KBspEI (SEQ ID NO: 16) | Anti-CD3 VL-VH |

The corresponding PCR product, which was flanked by two BspEI sites, was cloned into a plasmid designated BS-CTI, which was digested with BspEI and XmaI restriction enzymes. A polylinker designated CTI (SEQ ID NO: 36) was inserted before into the Bluescript KS vector (GenBank accession number X52327) using the restriction enzyme cleavage sites XbaI and SalI in order to provide additional cleavage sites as well as the sequence encoding a $G_4S$ linker, six consecutive histidine residues and a stop codon. During this cloning step the BspEI site of the VH domain was fused with the XmaI site of the plasmid thereby destroying both sites. The correct orientation of the variable domain was verified by sequencing according to standard protocols.

All molecular biological procedures indicated above were carried out according to standard protocols described in Sambrook, Molecular Cloning (A Laboratory Manual, 3rd edition, Cold Spring Harbor Laboratory Press, Cold Spring Harbor, N.Y. (2001).

DNA encoding the single chain bispecific antibodies in Table 1 (SEQ ID NOs: 29, 1, 3, 5, 7, 9, 11, 13) were transfected into DHFR deficient CHO cells for eukaryotic protein expression in DHFR deficient CHO cells as described in Mack et al. (Mack, Proc Natl Acad Sci USA 92 (1995), 7021-25). Gene amplification of the construct was induced by increasing concentrations of methotrexate (MTX) up to a final concentration of 20 nM MTX. The transfected cells were then expanded and 1 liter of supernatant produced.

EXAMPLE 2

Expression and Purification of the Single Chain Bispecific Antibodies Directed Against CD3 and CD19

The protein was expressed in chinese hamster ovary cells (CHO). Transfection of the expression vector was performed following calcium phosphate treatment of the cells ("Molecular Cloning", Sambrook et. al. 1989). The cells were grown in roller bottles with CHO modified DMEM medium (HiQ®, HiClone) for 7 days before harvest. The cells were removed by centrifugation and the supernatant containing the expressed protein was stored at −20° C.

Äkta® FPLC System (Pharmacia) and Unicorn™ Software were used for chromatography. All chemicals were of research grade and purchased from Sigma D (Deisenhofen) or Merck (Darmstadt). Immobilized metal affinity chromatography ("IMAC") was performed using a Fractogel® column (Merck) which was loaded with $ZnCl_2$ according to the protocol provided by the manufacturer. The column was equilibrated with buffer A2 (20 mM sodium phosphate buffer pH 7.5, 0.4 M NaCl) and the cell culture supernatant (500 ml) was applied to the column (10 ml) at a flow rate of 3 ml/min. The column was washed with buffer A2 to remove unbound sample. Bound protein was eluted using a 2 step gradient of buffer B2 (20 mM sodium phosphate buffer pH 7.5, 0.4 M NaCl, 0.5 M Imidazol) according to the following:
Step 1: 20% buffer B2 in 6 column volumes;
Step 2: 100% buffer B2 in 6 column volumes.

Eluted protein fractions from step 2 were pooled for further purification.

Gel filtration chromatography was performed on a Sephadex S200 HiPrep column (Pharmacia) equilibrated with PBS (Gibco). Eluted protein samples (flow rate 1 ml/min) were subjected to standard SDS-PAGE and Western Blot for detection (see FIGS. 4 and 5). Prior to purification, the column was calibrated for molecular weight determination (molecular weight marker kit,. Sigma MW GF-200). Protein concentrations were determined using protein assay dye (MicroBCA, Pierce) and IgG (Biorad) as standard protein.

The single chain bispecific antibodies were isolated in a two step purification process of IMAC (FIG. 2) and gel filtration (FIG. 3). The main product had a molecular weight of ca. 52 kDa under native conditions as determined by gel filtration in PBS. This molecular weight corresponds to the single chain bispecific antibody. All constructs were purified according to this method. Construct #4 could not be purified from cell culture supernatants due to extremely low levels of specific protein expressed and secreted into the supernatant.

Purified bispecific protein was analyzed in SDS PAGE under reducing conditions performed with pre-cast 4-12% Bis Tris gels (Invitrogen). Sample preparation and application were performed according to the protocol provided by the manufacturer. The molecular weight was determined with MultiMark protein standard (Invitrogen). The gel was stained with colloidal Coomassie (Invitrogen protocol). The purity of the isolated protein was >95% as determined by SDS-PAGE (FIG. 4; protein band at 52 kD).

Western Blot was performed using an Optitran® BA-S83 membrane and the Invitrogen Blot Module according to the protocol provided by the manufacturer. The antibodies used were directed against the His Tag (Penta His, Qiagen) and Goat-anti-mouse Ig labeled with alkaline phosphatase (AP) (Sigma), and BCIP/NBT (Sigma) as substrate. The single chain bispecific antibody could be specifically detected by Western Blot (FIG. 5). A single band was detected at 52 kD corresponding to the purified bispecific molecule.

EXAMPLE 3

Flow Cytometric Binding Analysis of CD19×CD3 Specific Polypetides

In order to test the functionality of the construct with regard to binding capability to CD19 and CD3, a FACS analysis was performed. For this purpose CD19 positive Nalm 6 cells (human B cell precursor leukemia) and CD3 positive Jurkat cells (human T cell leukemia) were used. 200,000 Nalm 6 cells and 200,000 Jurkat cells were respectively incubated for 30 min on ice with 50 µl of the pure cell supernatant of CHO cell cultures each expressing bispecific antibodies with different arrangements of VH and VL domains of CD19 and CD3 (as described in Example 2). The cells were washed twice in PBS and binding of the construct was detected as follows. The cells treated as described above were contacted with an unlabeled murine Penta His antibody (diluted 1:20 in 50 µl PBS with 2% FCS; Qiagen; Order No. 34660), which specifically binds to cell-bound construct via the construct's C-terminal histidine tag. A washing step followed to remove unbound murine Penta His antibody. Bound anti His antibodies were detected with an Fc gamma-specific antibody (Dianova, order no. 115-116-071) conjugated to phycoerythrin, diluted 1:100 in 50 µl PBS with 2% FCS (thick grey line in FIGS. 6A-6F). As a negative control (thin black line in FIGS. 6A-6F) fresh culture medium was used in place of culture supernatant.

Cells were analyzed by flow cytometry on a FACS-Calibur apparatus (Becton Dickinson, Heidelberg). FACS staining and measuring of the fluorescence intensity were performed as described in Current Protocols in Immunology (Coligan, Kruisbeek, Margulies, Shevach and Strober, Wiley-Interscience, 2002). The binding ability of several domain arrangements were clearly detectable as shown for example in FIGS. 6B, 6D and 6F. In FACS analysis all constructs with different arrangement of VH and VL domains specific for CD19 and CD3 showed binding to CD3 compared to the negative control using culture medium and 1. and 2. detection antibody. Strong binding activity resulting in a shift in fluorescence intensity >$5\times10^1$ was observed for the constructs shown in FIG. 6A (#1), B (#2), D(#6), E (#7), F (#8). Weaker binding to CD3 was observed for construct # 3 (FIG. 6C). Strong binding to CD19 was observed for all constructs.

EXAMPLE 4

Bioactivity of Bispecific Antibodies Specific for CD19 and CD3

Cytotoxic activity of the bispecific antibodies with rearranged VH and VL domains was determined in a fluorochrome release based cytotoxicity assay.

CD19 positive NALM6 cells were used as target cells ($1.5\times10^7$) labeled with 10 µM calcein AM (Molecular Probes, Leiden, Netherland, no. C-1430) for 30 min at 37° C. in cell culture medium. After two washes in cell culture medium, cells were counted and mixed with the CD4-positive T cell clone CB15 cells (kindly provided by Dr. Fickenscher, University of Erlangen/Nuernberg, Germany). $2\times10^6$ CB15 cells and $2\times10^5$ Nalm6 cells were mixed per ml (E:T ratio of 1:10) and 50 µl of this suspension was used per well in a 96 well round bottom plate. Antibodies were diluted in RPMI/10% FCS to the required concentration and 50 µl of this solution was added to the cell suspension. A standard reaction was incubated at 37° C./5% $CO_2$ for 2 hours. After the cytotoxic reaction, the released dye in the incubation medium can be quantitated in a fluorescence reader (Tecan, Crailsheim, Germany) and compared with the fluorescence signal from a control reaction (without bispecific antibody), and the fluorescence signal obtained for totally lysed cells (for 10 min in 1% saponin). On the basis of these readings, the specific cytotoxicity was calculated according to the following formula: [Fluorescence (Sample)–Fluorescence (Control)]: [Fluorescence (Total Lysis)–Fluorescence (Control)]×100.

Sigmoidal dose response curves typically had $R^2$ values >0.97 as determined by Prism Software (GraphPad Software Inc., San Diego, USA). $EC_{50}$ values calculated by the analysis program were used for comparison of bioactivity.

As shown in FIG. 7 all constructs revealed cytotoxic activity against CD19 expressing NALM 6 cells. Strongest bioactivity was observed for constructs #2, 6, 8 and 1. Strong cytotoxic activity with EC 50 values<500 pg/ml was detected for constructs #2, 6, 8 and 1. In addition to their high bioactivity, constructs #2 and #6 are also especially amenable to inclusion in pharmaceutical compositions. Constructs #3 and #7 showed EC 50 values of 52 ng/ml and 31 ng/ml respectively.

EXAMPLE 5

The 145-2C11 Antibody

The monoclonal antibody 145-2C11 directed against murine CD3 was analysed in different assays in order to characterize this antibody as group I or II anti-CD3 antibody. 145-2C11 was used by Brissinck, 1991, J. Immunol. 147-4019 for constructing a bispecific antibody directed against BCL-1 and murine CD3 and also by de Jonge, 1997, Cancer Immunol. Immunother. 45-162.

5.1. Binding of 145-2C11 to the Recombinant, Purified Extracellular Domain of the Murine CD3 Epsilon Chain in ELISA The anti-murine CD3 epsilon antibody (145-2C11 BD biosciences, Heidelberg, FRG) was coated (50 µl at 5 µg/ml in PBS) on a Maxisorp ELISA plate (Nunc GmbH, Wiesbaden, FRG). After overnight incubation unspecific binding was blocked with 1,5% BSA in PBS for 1 hour. After washing three times with 200 µl PBS, different dilutions of the recombinant C-terminally His6-tagged CD3 protein (obtained by a procedure analogous to that described in Example 6 for obtaining recombinant human CD3epsilon) and an irrelevant antigen (BSA) were incubated for 1 hour in the prepared cavities of the plate. Binding of recombinant CD3 was detected with horseradish peroxidase conjugated anti-His antibody (Roche Diagnostics GmbH, Mannheim, FRG; diluted 1:500 in 1.5% BSA in PBS) binding to a polyhistidine tag. ABTS (2,2'-Azino-di[3-ethylbenzthiazoline sulfonate (6)] diammonium salt, Roche Diagnostics GmbH, Mannheim, FRG) was used as substrate according to the specifications of the manufacturer. The absorbance values were measured on a SPECTRAFluor Plus photometer (Tecan Deutschland GmbH, Crailsheim). The measurement wavelength was 405 nm, the reference wavelength was 620 nm. XFLUOR4 Version: V 4.40 for Windows was used as analysis software. Specific binding of the recombinant, purified extracellular domain of the murine CD3 epsilon chain to the 145-2C11 antibody was detected for antibody dilutions of 1:5 and 1:25. (FIG. 8).

5.2. Binding of 145-2C11 to a Human T Cell Line Transfected with the Murine CD3 Epsilon Chain in FACS Binding of 145-2C11 antibody to Jurkat cells (obtained from ATCC) transfected with the murine CD3 epsilon chain surface antigen was tested using an FACS assay. To this end, $2.5 \times 10^5$ cells were incubated with a 1:50 dilution of the PE-conjugated 145-2C11 antibody (BD biosciences, Heidelberg, FRG) in 50 µl PBS with 2% FCS. As a control another sample of cells was incubated with a 1:50 dilution of a PE-conjugated hamster IgG group1 Kappa isotype control. (BD biosciences, Heidelberg, FRG) in 50 µl PBS with 2% FCS. Untransfected cells were also assayed under the described conditions. The samples were measured on a FACSscan (BD biosciences, Heidelberg, FRG). Specific binding of the 145-2C11 antibody as compared to the isotype control was clearly detectable on the transfected but not on the untransfected cells (FIGS. 9 and 10) inducing a shift in fluorescence intensity.

5.3. Binding of 145-2C11 to a Murine T Cell Line in FACS

Binding of 145-2C11 antibody to CTLL2 cells (obtained from ATCC) was tested using an FACS assay. $2.5 \times 10^5$ cells were incubated with a 1:50 dilution of the PE-conjugated 145-2C11 antibody (BD biosciences, Heidelberg, FRG) in 50 µl PBS with 2% FCS. As a control another aliquot of cells was incubated with a 1:50 dilution of a PE-conjugated hamster IgG group1 Kappa isotype control (BD biosciences, Heidelberg, FRG) in 50 µl PBS with 2% FCS. The samples were measured on a FACSscan (BD biosciences, Heidelberg, FRG). Specific binding of the 145-2C11 antibody as compared to the isotype control was clearly detectable (FIG. 11).

In summary, these data clearly showed that murine anti CD3 antibody 145-2C11 recognized purified recombinant CD3 epsilon as well as murine CD3 epsilon expressed in eukaryotic cells. 145-2C11 bound to Jurkat cells transfected with murine CD3 epsilon as well as to a murine T cell line expressing the CD3 epsilon chain in its native murine TCR receptor complex. Both cell lines express CD3 epsilon on the cell surface in the context of other TCR subunits. These two criteria—binding to purified recombinant CD3 epsilon as well as binding to cells expressing CD3 epsilon in the TCR complex—were described as the essential features of anti CD3 antibodies belonging to "group I" according to the classification described by Tunnacliffe et al. (Tunnacliffe, 1989, Int. Immunol., 1, 546-550). In contrast, "group II" antibodies specifically bind to epitopes the conformations of which are dependent on the whole T cell receptor complex. According to these definitions 145-2C11 could clearly be classified as an anti CD3 antibody belonging to "group I". This confirms the observations of Leo, Proc. Natl. Acad. Sci USA (1987), 1374, who found that 145-2C11 could still bind to CD3 epsilon when it was dissociated by detergent treatment from the other chains of the CD3- and T cell receptor-complex, thus revealing a "group I" CD3 binding pattern.

EXAMPLE 6

Assignment of CD3-reactive Bispecific Single-chain Antibodies to Different CD3-binding Patterns CD3-reactive bispecific single-chain antibodies may be assigned to different CD3-binding patterns according to the classification of Tunnacliffe, International Immunology 1 (1989), 546. In order to assign a CD3-reactive bispecific single-chain antibody to the "group I" CD3-binding pattern an ELISA may be carried out with purified recombinant human CD3-epsilon. Recombinant human CD3-epsilon may be e.g. obtained as C-kappa-fusion construct as described by Tunnacliffe, Immunol. Lett. 21 (1989) 243 or as truncated soluble CD3-epsilon available according to the following procedure:

cDNA was isolated from human peripheral blood mononuclear cells. Preparation of the cells was performed according to standard protocols (Current Protocols in Immunology (Coligan, Kruisbeek, Margulies, Shevach and Strober, John Wiley & Sons, Inc., USA, 2002)). The isolation of total RNA and cDNA synthesis by random-primed reverse transcription was performed according to standard protocols (Sambrock, Molecular Cloning; Laboratory Manual, 2nd edition, Cold Spring Harbor laboratory Press, Cold Spring Harbor, N.Y. (1989)). PCR was used to amplify the coding sequence of the extracellular domain of the human CD3 epsilon chain. The primers used in the PCR were designed so as to introduce restriction sites at the beginning and the end of the cDNA coding for the extracellular portion of the human CD3 epsilon chain (SEQ ID NO: 80 and SEQ ID NO:81). The introduced restriction sites, BsrGI and BspEI, were utilised in the following cloning procedures. The PCR product was then cloned via BsrGI and BspEI into a plasmid designated BS-Fss-Lsp derived from the Bluescript KS⁺ cloning vector (Stratagene Europe, Amsterdam-Zuiddoost, the Netherlands) following standard protocols. (The vector was generated by cloning a DNA fragment (SEQ ID NO: 82) via EcoRI and SalI into Bluescript KS⁺.) The sequence of different clones was determined by sequencing according to standard protocols. By cloning into BS-Fss-Lsp the coding sequence of a murine immunoglobulin heavy chain leader peptide was fused in-frame to the 5' end of the coding sequence for the extracellular portion of the human CD3 epsilon chain. The cDNA was then cloned via EcoRI and BspEI into another plasmid designated as BSCTI to attach a sequence to the C-terminus, coding for a polyhistidine tag of six consecutive histidine residues followed by a stop codon (BSCTI is described in Kufer, Cancer Immunity 1 (2001), 10). In this step the BspEI site of the cDNA was fused into an XmaI site of the plasmid thereby destroying both sites. All cloning steps were designed so as to generate an intact reading frame for the construct. The plasmid now contained a sequence coding for a protein comprising a murine immunoglobulin heavy chain leader peptide, to allow for secreted expression, followed by the extracellular domain of the human CD3 epsilon chain followed by a polyhistidine tag of six consecutive histidine residues, to allow for purification and detection via the polyhistidine tag (SEQ ID NO: 78 and SEQ ID NO: 79). This sequence was then cloned into the plasmid pFastBac1™ (Invitrogen GmbH, Karlsruhe, FRG) via EcoRI and SalI.

Expression of the extracellular domain of the human CD3 epsilon chain in High Five™ cells was performed using the Bac-to-Bac® Baculovirus Expression System (Invitrogen GmbH, Karlsruhe, FRG) according to the specifications of the manufacturer. 10 liters of supernatant in batches of 500 ml were produced. The construct was then purified out of the culture supernatant. Purification was performed as a two-step purification. First the diluted supernatants were loaded on ion exchange columns. The fractionated eluate was tested in an ELISA assay. To this end, an anti-human CD3 epsilon antibody (UCHT1 BD biosciences, Heidelberg, FRG) was coated (50 µl at 5 µg/ml in PBS) on a Maxisorp ELISA plate (Nunc GmbH, Wiesbaden, FRG) overnight. Unspecific binding was blocked with 1.5% BSA in PBS for 1 hour. All prior and subsequent washing steps were performed three times with 200 µl PBS. Afterwards, eluate fractions were incubated for 1 hour in the prepared cavities of the plate. Detection of the recombinant protein was performed with a horseradish peroxidase conjugated anti-His antibody (Roche Diagnostics GmbH, Mannheim, FRG; 50 µl of antibody diluted 1:500 in 1.5% BSA in PBS). Development of the ELISA was performed with ABTS (2,2'-Azino-bis(3-Ethylbenz-Thiazolin)-6-Sulfonic acid) Roche Diagnostics GmbH, Mannheim, FRG) according to the specifications of the manufacturer. Positive fractions were further purified over a cobalt-chelate column which preferentially binds histidine-tagged proteins. Eluate fractions were tested using the described ELISA assay. Positive fractions were pooled and concentrated.

For assignment of CD3-reactive bispecific single-chain antibodies to the "group I" CD3-binding pattern, purified recombinant human CD3-epsilon may be coated (50 µl at 10 µg/ml in PBS) on a Maxisorp ELISA plate (Nunc GmbH, Wiesbaden, FRG) overnight and unspecific binding subsequently blocked with 1.5% BSA in PBS for 1 hour. Next the ELISA wells are washed three times with 200 µl PBS. Then purified CD3-reactive bispecific single-chain antibody (50 µl at 10 µg/ml in 1.5% BSA in PBS) in a version, that (i) contains an N-terminal FLAG-tag with the amino acid sequence: dykddddk (obtainable e.g. as described in Mack, PNAS 92 (1995) 7021) but (ii) avoids a polyhistidine tag can be incubated for 1 hour on immobilized CD3-epsilon. As negative control 50 µl 1.5% BSA in PBS without bispecific single-chain antibody may be used. As positive control the "group I" anti-CD3 antibody UCHT1 (BD biosciences, Heidelberg, FRG; 50 µl of antibody diluted to 5 µg/ml in 1.5% BSA in PBS) may be incubated on immobilized CD3-epsilon. After another washing step carried out as above, bispecific single-chain antibody specifically bound to human CD3-epsilon can be detected with an unconjugated anti-FLAG antibody (ANTI-FLAG M2 obtained from Sigma-Aldrich Chemie GmbH, Taufkirchen FRG; 50 µl of antibody diluted to 5 µg/ml in 1.5% BSA in PBS) followed by a horseradish peroxidase-conjugated, goat anti-mouse IgG, Fc-gamma fragment specific antibody (obtained from Dianova, Hamburg, FRG; diluted 1:1000 in 50 µl PBS with 1.5% BSA), which directly detects the control antibody bound to immobilized CD3-epsilon. Development of the ELISA was carried out with ABTS (Roche Diagnostics GmbH, Mannheim, FRG) for 90 minutes in accordance with the specifications of the manufacturer. In contrast to the control antibody UCHT-1 none of the bispecific single-chain antibodies based on the CD3-binding specificity described by Traunecker, EMBO J. 10 (1991) 3655 showed specific interaction with purified recombinant human CD3-epsilon, thus excluding assignment to the "group I" CD3-binding pattern. Differentiation between the "group II" and the "group III" CD3-binding patterns may be carried out by flowcytometric binding analysis of CD3-reactive bispecific single-chain antibodies on human T cells and human CD3-epsilon-transgenic murine T cells as described e.g. in Tunnacliffe, International Immunology 1(1989) 546. Flowcytometry may be carried out as described in Example 3 of the present invention if the bispecific single-chain antibody to be analyzed carries a polyhistidine-tag or according to the same protocol, except that the detection antibody is replaced by a fluorescence-labeled anti-Flag antibody if the bispecific single-chain antibody is Flag-tagged.

The invention claimed is:

1. A pharmaceutical composition comprising a bispecific single chain antibody construct, said bispecific single chain antibody construct comprising binding domains specific for human CD3 and human CD19, wherein the corresponding variable heavy chain regions ($V_H$) and the corresponding variable light chain regions ($V_L$) regions are arranged, from N-terminus to C- terminus, in the order, $V_H$(CD19)-$V_L$(CD19)-$V_H$(CD3)-$V_L$(CD3), or
$V_H$(CD3)-$V_L$(CD3)-$V_H$(CD19)-$V_L$(CD19).

2. The pharmaceutical composition of claim 1, wherein said $V_H$ and $V_L$ regions of said CD3 specific domain are derived from an CD3 specific antibody consisting of: OKT-3.

3. The pharmaceutical composition of claim 1, wherein said $V_H$ region comprises at least one CDR3 region comprising the amino acid sequence: SEQ ID NO: 54; at least one CDR2 region comprising the amino acid sequence: SEQ ID NO: 53; and at least one CDR1 region comprising the amino acid sequence: SEQ ID NO: 52; and wherein said $V_L$ region comprises at least one CDR3 region comprising the amino acid sequence: SEQ ID NO: 57; at least one CDR2 region comprising the amino acid sequence: SEQ ID NO: 56; and at least one CDR1 region comprising the amino acid sequence: SEQ ID NO: 55.

4. The pharmaceutical composition of claim 1, wherein said bispecific single chain antibody construct comprises an amino acid sequence selected from the group consisting of
   (a) an amino acid sequence as depicted in SEQ ID NO: 2;
   (b) an amino acid sequence encoded by a nucleic acid sequence as shown in SEQ ID NOs: 1, 9 or 13; and
   (c) an amino acid sequence encoded by a nucleic acid sequence which is degenerate as a result of the genetic code to a nucleotide sequence of (b).

5. The pharmaceutical composition of claim 1, wherein said variable domains are connected by additional linker sequences.

6. A pharmaceutical composition claim 1 further comprising a proteinaceous compound capable of providing an activation signal for immune effector cells, wherein the proteinaceous compound is selected from the group consisting of scFv fragments specific for 4-1BB, OX 40, CD27, CD70, the receptors for B7-RP1, B7-H3 and scFv fragments specific for the T cell receptor or superantigens.

7. A process for the production of a pharmaceutical composition of claim 1, said process comprising culturing a host cell under conditions allowing the expression of a bispecific single chain antibody construct comprising binding domains specific for human CD3 and human CD 19, wherein the corresponding variable heavy chain regions ($V_H$) and the corresponding variable light chain regions ($V_L$) are arranged, from N-terminus to C- terminus, in the order $V_H$(CD19)-$V_L$(CD19)-$V_H$(CD3)-$V_L$(CD3) or $V_H$(CD3)-$V_L$(CD3)-$V_H$(CD19)-$V_L$(CD19), recovering the produced bispecific single chain antibody construct from the culture, and producing the pharmaceutical composition.

8. A kit comprising a bispecific single chain antibody construct as defined in claim 1.

* * * * *

UNITED STATES PATENT AND TRADEMARK OFFICE
CERTIFICATE OF CORRECTION

PATENT NO. : 7,635,472 B2　　　　　　　　　　　　　　　　　　　　　　　　　　Page 1 of 1
APPLICATION NO. : 10/554852
DATED : December 22, 2009
INVENTOR(S) : Kufer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this

Ninth Day of November, 2010

David J. Kappos
*Director of the United States Patent and Trademark Office*